(12) United States Patent
Rives et al.

(10) Patent No.: US 9,290,568 B2
(45) Date of Patent: *Mar. 22, 2016

(54) METHODS TO CONTROL PROTEIN HETEROGENEITY

(71) Applicant: ABBVIE INC., North Chicago, IL (US)

(72) Inventors: Lisa M. Rives, Natick, MA (US); Cornelia Bengea, Auburn, MA (US); Xiaobei Zeng, Carolina, PR (US)

(73) Assignee: AbbVie, Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,572

(22) Filed: Feb. 26, 2015

(65) Prior Publication Data

US 2015/0183866 A1    Jul. 2, 2015

Related U.S. Application Data

(63) Continuation of application No. 14/194,305, filed on Feb. 28, 2014, which is a continuation of application No. 13/804,220, filed on Mar. 14, 2013.

(60) Provisional application No. 61/696,219, filed on Sep. 2, 2012.

(51) Int. Cl.
   *A61K 39/00* (2006.01)
   *C07K 16/00* (2006.01)
   *C07K 16/24* (2006.01)

(52) U.S. Cl.
   CPC ............ *C07K 16/241* (2013.01); *C07K 2317/14* (2013.01); *C07K 2317/21* (2013.01); *C07K 2317/41* (2013.01); *C12N 2510/02* (2013.01)

(58) Field of Classification Search
   CPC ....... C12N 5/00; C12N 5/0018; C12N 5/1002
   See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |

(Continued)

FOREIGN PATENT DOCUMENTS

| | | |
|---|---|---|
| CN | 1299370 A | 6/2001 |
| CN | 1563090 A | 1/2005 |

(Continued)

OTHER PUBLICATIONS

Burteau et al., (In Vitro Cell Dev Biol—Animal. Jul./Aug. 2003. 39:291-296).*

(Continued)

*Primary Examiner* — Cherie M Stanfield
(74) *Attorney, Agent, or Firm* — McCarter & English, LLP; Maria Laccotripe Zacharakis; Maneesh Gulati

(57) ABSTRACT

The instant invention relates to the field of protein production and in particular to controlled protein heterogeneity compositions and processes for controlling the heterogeneity of proteins expressed in host cells.

30 Claims, 46 Drawing Sheets

(56) References Cited

U.S. PATENT DOCUMENTS

| | | | |
|---|---|---|---|
| 4,816,397 | A | 3/1989 | Boss et al. |
| 4,877,608 | A | 10/1989 | Lee et al. |
| 4,927,762 | A | 5/1990 | Darfler |
| 4,933,435 | A | 6/1990 | Ngo |
| 4,968,615 | A | 11/1990 | Koszinowski et al. |
| 5,045,468 | A | 9/1991 | Darfler |
| 5,096,816 | A | 3/1992 | Maiorella |
| 5,110,913 | A | 5/1992 | Coan et al. |
| 5,118,796 | A | 6/1992 | Prior et al. |
| 5,122,469 | A | 6/1992 | Mather et al. |
| 5,126,250 | A | 6/1992 | McDonough et al. |
| 5,168,062 | A | 12/1992 | Stinski |
| 5,179,017 | A | 1/1993 | Axel et al. |
| 5,231,024 | A | 7/1993 | Moeller et al. |
| 5,328,985 | A | 7/1994 | Sano et al. |
| 5,378,612 | A | 1/1995 | Nakashima et al. |
| 5,429,746 | A | 7/1995 | Shadle et al. |
| 5,530,101 | A | 6/1996 | Queen et al. |
| 5,545,403 | A | 8/1996 | Page |
| 5,545,806 | A | 8/1996 | Lonberg et al. |
| 5,545,807 | A | 8/1996 | Surani et al. |
| 5,561,053 | A | 10/1996 | Crowley |
| 5,569,825 | A | 10/1996 | Lonberg et al. |
| 5,625,126 | A | 4/1997 | Lonberg et al. |
| 5,633,162 | A | 5/1997 | Keen et al. |
| 5,633,425 | A | 5/1997 | Lonberg et al. |
| 5,644,036 | A | 7/1997 | Ramage et al. |
| 5,654,407 | A | 8/1997 | Boyle et al. |
| 5,656,272 | A | 8/1997 | Le et al. |
| 5,661,016 | A | 8/1997 | Lonberg et al. |
| 5,672,347 | A | 9/1997 | Aggarwal et al. |
| 5,672,502 | A | 9/1997 | Birch et al. |
| 5,698,195 | A | 12/1997 | Le et al. |
| 5,705,364 | A | 1/1998 | Etcheverry et al. |
| 5,721,121 | A | 2/1998 | Etcheverry et al. |
| 5,770,429 | A | 6/1998 | Lonberg et al. |
| 5,789,650 | A | 8/1998 | Lonberg et al. |
| 5,795,967 | A | 8/1998 | Aggarwal et al. |
| 5,811,299 | A | 9/1998 | Renner et al. |
| 5,859,205 | A | 1/1999 | Adair et al. |
| 5,876,961 | A | 3/1999 | Crowe et al. |
| 5,877,293 | A | 3/1999 | Adair et al. |
| 5,929,212 | A | 7/1999 | Jolliffe et al. |
| 5,945,098 | A | 8/1999 | Sarno et al. |
| 5,976,833 | A | 11/1999 | Furukawa et al. |
| 5,994,510 | A | 11/1999 | Adair et al. |
| 6,024,938 | A | 2/2000 | Corbo et al. |
| 6,036,978 | A | 3/2000 | Gombotz et al. |
| 6,048,728 | A | 4/2000 | Inlow et al. |
| 6,066,719 | A | 5/2000 | Zapata |
| 6,075,181 | A | 6/2000 | Kucherlapati et al. |
| 6,090,382 | A * | 7/2000 | Salfeld et al. ............ 424/133.1 |
| 6,093,324 | A | 7/2000 | Bertolini et al. |
| 6,113,898 | A | 9/2000 | Anderson et al. |
| 6,150,584 | A | 11/2000 | Kucherlapati et al. |
| 6,171,586 | B1 | 1/2001 | Lam et al. |
| 6,255,458 | B1 | 7/2001 | Lonberg et al. |
| 6,258,562 | B1 | 7/2001 | Salfeld et al. |
| 6,270,766 | B1 | 8/2001 | Feldman et al. |
| 6,300,129 | B1 | 10/2001 | Lonberg et al. |
| 6,339,142 | B1 | 1/2002 | Basey et al. |
| 6,399,381 | B1 | 6/2002 | Blum et al. |
| 6,406,909 | B1 | 6/2002 | Shibuya et al. |
| 6,410,270 | B1 | 6/2002 | Strittmatter et al. |
| 6,413,746 | B1 | 7/2002 | Field |
| 6,436,397 | B1 | 8/2002 | Baker et al. |
| 6,448,380 | B2 | 9/2002 | Rathjen et al. |
| 6,451,983 | B2 | 9/2002 | Rathjen et al. |
| 6,489,447 | B1 | 12/2002 | Basey et al. |
| 6,498,237 | B2 | 12/2002 | Rathjen et al. |
| 6,509,015 | B1 | 1/2003 | Salfeld et al. |
| 6,528,286 | B1 | 3/2003 | Ryll |
| 6,593,458 | B1 | 7/2003 | Rathjen et al. |
| 6,673,575 | B1 | 1/2004 | Franze et al. |
| 6,673,986 | B1 | 1/2004 | Kucherlapati et al. |
| 6,680,181 | B2 | 1/2004 | Castan |
| 6,870,034 | B2 | 3/2005 | Breece et al. |
| 6,872,549 | B2 | 3/2005 | Van Ness et al. |
| 6,890,736 | B1 | 5/2005 | Reddy et al. |
| 6,900,056 | B2 | 5/2005 | Lee et al. |
| 6,914,128 | B1 | 7/2005 | Salfeld et al. |
| 6,924,124 | B1 | 8/2005 | Singh |
| 6,974,681 | B1 | 12/2005 | McGrew |
| 7,070,775 | B2 | 7/2006 | Le et al. |
| 7,084,260 | B1 | 8/2006 | Lonberg et al. |
| 7,122,641 | B2 | 10/2006 | Vedantham et al. |
| 7,189,820 | B2 | 3/2007 | Ruben |
| 7,192,584 | B2 | 3/2007 | Le et al. |
| 7,223,394 | B2 | 5/2007 | Salfeld et al. |
| 7,250,165 | B2 | 7/2007 | Heavner et al. |
| 7,276,239 | B2 | 10/2007 | Le et al. |
| 7,323,553 | B2 | 1/2008 | Fahrner et al. |
| 7,332,303 | B2 * | 2/2008 | Schilling et al. ............ 435/69.7 |
| 7,390,660 | B2 | 6/2008 | Behrendt et al. |
| 7,429,491 | B2 | 9/2008 | Luan et al. |
| 7,504,485 | B2 | 3/2009 | Salfeld et al. |
| 7,521,206 | B2 | 4/2009 | Heavner et al. |
| 7,521,210 | B2 | 4/2009 | Knudsen |
| 7,541,031 | B2 | 6/2009 | Salfeld et al. |
| 7,588,761 | B2 | 9/2009 | Salfeld et al. |
| 7,645,609 | B2 | 1/2010 | Follstad |
| 7,714,112 | B2 | 5/2010 | Engstrand et al. |
| 7,750,129 | B2 | 7/2010 | Johansson et al. |
| 7,767,207 | B2 | 8/2010 | Ghayer et al. |
| 7,863,426 | B2 | 1/2011 | Wan et al. |
| 7,883,704 | B2 | 2/2011 | Salfeld et al. |
| 7,919,264 | B2 | 4/2011 | Maksymowych et al. |
| 7,947,471 | B2 | 5/2011 | Knudsen |
| 7,972,810 | B2 | 7/2011 | Crowell et al. |
| 8,034,906 | B2 | 10/2011 | Borhani et al. |
| 8,067,182 | B2 | 11/2011 | Kelley et al. |
| 8,093,045 | B2 | 1/2012 | Pla et al. |
| 8,192,951 | B2 | 6/2012 | Wang et al. |
| 8,197,813 | B2 | 6/2012 | Salfeld et al. |
| 8,206,714 | B2 | 6/2012 | Salfeld et al. |
| 8,209,132 | B2 | 6/2012 | Bosques et al. |
| 8,216,583 | B2 | 7/2012 | Kruase et al. |
| 8,231,876 | B2 | 7/2012 | Wan et al. |
| 8,361,797 | B2 | 1/2013 | Osborne et al. |
| 8,372,400 | B2 | 2/2013 | Salfeld et al. |
| 8,372,401 | B2 | 2/2013 | Salfeld et al. |
| 8,414,894 | B2 | 4/2013 | Salfeld et al. |
| 8,420,081 | B2 | 4/2013 | Fraunhofer et al. |
| 8,436,149 | B2 | 5/2013 | Borhani et al. |
| 8,470,552 | B2 | 6/2013 | Croughan et al. |
| 8,512,983 | B2 | 8/2013 | Gawlitzek et al. |
| 8,663,945 | B2 | 3/2014 | Pla et al. |
| 8,753,633 | B2 | 6/2014 | Salfeld et al. |
| 8,821,865 | B2 | 9/2014 | Neu et al. |
| 8,852,889 | B2 | 10/2014 | Prentice |
| 8,883,146 | B2 | 11/2014 | Fraunhofer et al. |
| 8,883,156 | B2 | 11/2014 | Wan et al. |
| 8,895,009 | B2 | 11/2014 | Wan et al. |
| 8,895,709 | B2 | 11/2014 | Hickman et al. |
| 8,906,372 | B2 | 12/2014 | Wan et al. |
| 8,906,646 | B2 | 12/2014 | Pla et al. |
| 8,911,964 | B2 | 12/2014 | Pla et al. |
| 8,916,153 | B2 | 12/2014 | Wan et al. |
| 8,921,526 | B2 | 12/2014 | Chumsae et al. |
| 8,946,395 | B1 | 2/2015 | Herigstad et al. |
| 9,017,687 | B1 | 4/2015 | Wang et al. |
| 9,062,106 | B2 | 6/2015 | Bengea et al. |
| 9,067,990 | B2 | 6/2015 | Wang at al. |
| 9,085,618 | B2 | 7/2015 | Ramasubramanyan et al. |
| 9,085,619 | B2 | 7/2015 | Fraunhofer et al. |
| 9,090,688 | B2 | 7/2015 | Bengea et al. |
| 9,096,879 | B2 | 8/2015 | Khetan et al. |
| 9,150,645 | B2 | 10/2015 | Subramanian at al. |
| 9,181,337 | B2 | 11/2015 | Subramanian et al. |
| 9,181,572 | B2 | 11/2015 | Subramanian et al. |
| 9,200,069 | B2 | 12/2015 | Ramasubramanyan et al. |
| 9,200,070 | B2 | 12/2015 | Ramasubramanyan et al. |
| 9,206,390 | B2 | 12/2015 | Rives et al. |
| 2002/0045207 | A1 | 4/2002 | Krummen et al. |

(56) References Cited

U.S. PATENT DOCUMENTS

| | | |
|---|---|---|
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0134256 A1 | 6/2007 | Lai et al. |
| 2007/0161084 A1* | 7/2007 | Crowell et al. ............ 435/69.1 |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1* | 9/2008 | Pla et al. ............ 435/29 |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0151023 A1 | 6/2009 | Kuvshinov et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0253174 A1 | 10/2009 | Serber et al. |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0172911 A1* | 7/2010 | Naso et al. ............ 424/141.1 |
| 2010/0189717 A1 | 7/2010 | Kim et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2011/0318340 A1 | 12/2011 | Collin et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0093810 A1 | 4/2012 | Takada et al. |
| 2012/0107783 A1 | 5/2012 | Julian et al. |
| 2012/0123688 A1 | 5/2012 | Ramasubramanyan et al. |

(56) References Cited

U.S. PATENT DOCUMENTS

| | | |
|---|---|---|
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0244280 A1 | 9/2013 | Parikh et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |
| 2014/0288278 A1 | 9/2014 | Nti-gyabaah et al. |
| 2014/0301977 A1 | 10/2014 | Nadarajah et al. |
| 2014/0314745 A1* | 10/2014 | Rives et al. ............... 424/133.1 |
| 2014/0363845 A1 | 12/2014 | Sinacore et al. |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0132320 A1 | 5/2015 | Chumsae et al. |
| 2015/0132801 A1 | 5/2015 | Ramasubramanyan et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1* | 7/2015 | Rives et al. ............... 424/133.1 |
| 2015/0183866 A1 | 7/2015 | Rives et al. |
| 2015/0259410 A1 | 9/2015 | Ramasubramanyan et al. |
| 2015/0299249 A1 | 10/2015 | Herigstad et al. |

FOREIGN PATENT DOCUMENTS

| | | |
|---|---|---|
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2305712 A1 | 4/2011 |
| EP | 2357250 A2 | 8/2011 |
| EP | 2495307 A1 | 9/2012 |
| EP | 2528002 A2 | 11/2012 |
| EP | 2574677 A1 | 4/2013 |
| GB | 2160530 A | 12/1985 |
| GB | 2279077 A | 12/1994 |
| IN | 2285/MUM/2013 | 10/2014 |
| JP | 6-292592 | 10/1994 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-97/04801 A1 | 2/1997 |
| WO | WO-97/13852 A1 | 4/1997 |
| WO | WO-97/29131 A1 | 8/1997 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-98/50433 A2 | 11/1998 |
| WO | WO-98/56418 A1 | 12/1998 |

(56) References Cited

FOREIGN PATENT DOCUMENTS

| WO | WO-99/32605 A1 | 7/1999 |
|---|---|---|
| WO | WO-99/57134 A1 | 11/1999 |
| WO | WO-99/57246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-2003/046162 | 6/2003 |
| WO | WO-03045995 A2 | 6/2003 |
| WO | WO-03/059935 A2 | 7/2003 |
| WO | WO-03/066662 A2 | 8/2003 |
| WO | WO-2004008100 A2 | 1/2004 |
| WO | WO-2004/058944 A2 | 7/2004 |
| WO | WO-2004058800 A2 | 7/2004 |
| WO | WO-2004/097006 A1 | 11/2004 |
| WO | WO-2005042569 A1 | 5/2005 |
| WO | WO-2005-062967 A2 | 7/2005 |
| WO | WO-2005/082483 A1 | 9/2005 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007/070315 A2 | 6/2007 |
| WO | WO-2007/087384 A2 | 8/2007 |
| WO | WO-2007/117490 A2 | 10/2007 |
| WO | WO-2008/033517 A2 | 3/2008 |
| WO | WO-2008-057240 A2 | 5/2008 |
| WO | WO-2008068879 A1 | 6/2008 |
| WO | WO-2008087184 A2 | 7/2008 |
| WO | WO-2008121616 A2 | 10/2008 |
| WO | WO-2008/135498 A2 | 11/2008 |
| WO | WO-2009/027041 A1 | 1/2009 |
| WO | WO-2009/017491 A1 | 2/2009 |
| WO | WO-2009023562 A2 | 2/2009 |
| WO | WO-2009058769 A1 | 5/2009 |
| WO | WO-2009/073569 A2 | 6/2009 |
| WO | WO-2009135656 A1 | 11/2009 |
| WO | WO-2010-048183 A1 | 4/2010 |
| WO | WO-2010036443 A1 | 4/2010 |
| WO | WO-2010/043703 A1 | 4/2010 |
| WO | WO-2010122460 A1 | 10/2010 |
| WO | WO-2010/129469 A1 | 11/2010 |
| WO | WO-2010127069 A1 | 11/2010 |
| WO | WO-2010/136209 A1 | 12/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012/046255 A2 | 4/2012 |
| WO | WO-2012050175 A1 | 4/2012 |
| WO | WO-2012051147 A1 | 4/2012 |
| WO | WO-2012/065072 A2 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013-011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-066707 A1 | 5/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-164837 A1 | 11/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |
| WO | WO-2013-186230 A1 | 12/2013 |
| WO | WO-2014/039903 A2 | 3/2014 |
| WO | WO-2014/099636 A1 | 6/2014 |
| WO | WO-2014/151878 A2 | 9/2014 |
| WO | WO-2014/207763 A1 | 12/2014 |
| WO | WO-2015/004679 A1 | 1/2015 |
| WO | WO-2015/007912 A1 | 1/2015 |

OTHER PUBLICATIONS

Raju (BioProcess International. Apr. 2003: 44-53).*
Andersen et al. (Curr Opin Biotech 1994 5:546-549).*
Goochee et al., (Biotechnology, Dec. 1991 9:1346-1355).*
Parekh et al., (TIBTECH, May 1989 7:117-122).*
Chung et al. "Cetuximab-induced anaphylaxis and IgE specific for galactose-a-1,3-galactose" NEJM 358:11, 1109-1117 (2008).
Fahrner et al., "Industrial purification of pharmaceutical antibodies: development, operation, and validation of chromatography processes" Biotechnology and Genetic Engineering Reviews, 18, 2001, pp. 301-327.
International Preliminary Report on Patentability for Application No. PCT/US2013/031365, dated Mar. 3, 2015, 9 pages.
Kazuaki F et al "Enhancement of productivity of recombinant a-amidating enzyme by low temperature culture" Cytotechnology 31:85-94, 1999.
Liu et al. "Recovery and purification process development for monoclonal antibody production" mabs, 2(5), pp. 480-499 (2010).
Pete Gagnon "Polishing methods for monoclonal IgG purification" Chapter 17, Taylor & Francis Group, LLC, pp. 491-505, 2007.
Shubert et al. "Comparison of ceramic hydroxy- and fluoroapatite versus Protein A/G—based resins in the isolation of a recombinant human antibody from cell culture supernatant" J. Chromatography A, 114 (2007) 106-113.
DIONEX Application Note 125 (Monitoring Protein Deamidation by Cation-Exchange Chromatography. 2009; pp. 1-7).
"Genentech unveils production capacity hikes," in-Pharma Technologist.com Jun. 28, 2005, pp. 1-2.
"Memorandum in Support of Centocor's Motion for Summary Judgment No. 1 that All Asserted Claims are Invalid for Lack of Written Description", dated Aug. 1, 2013 and submitted by defendant in Civil Action No. 09-40089-FDS, 28 pages.
"Memorandum in Support of Centocor's Motion for Summary Judgment No. 2 that All Asserted Claims are Invalid for Lack of Enablement", dated Aug. 1, 2013 and submitted by defendant in Civil Action No. 09-40089-FDS, 22 pages.
"Memorandum in Support of Centocor's Motion for Summary Judgment No. 4 that Claims Encompassing Non-recombinant Human Antibodies are Invalid for Failing to Meet the Requirements of 35 U.S.C. §112", dated Aug. 1, 2013 and submitted by defendant in Civil Action No. 09-40089-FDS, 21 pages.
"Memorandum in Support of Centocor's Motion No. 3 for Summary Judgment that the 394 and 031 Patents are Invalid for Under 35 U.S.C. §102(f) for Failing to Name the Proper Inventors", dated Aug. 1, 2013 and submitted by defendant in Civil Action No. 09-40089-FDS, 13 pages.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.

(56) References Cited

OTHER PUBLICATIONS

"Plaintiffs' Memorandum in Support of Their Motion for Partial Summary Judgment", dated Aug. 1, 2013 and submitted by plaintiff in Civil Action No. 09-40089-FDS, 49 pages.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.
Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.
Abraham, E., et al., "Efficacy and Safety of Monoclonal Antibody to Human Tumor Necrosis Factor α in Patients with Sepsis Syndrome," *JAMA*, vol. 273(12):934-941 (1995).
Adams. et al., "Aggressive cutaneous T-cell lymphomas after TNFα blockade," J. Am. Acad. Dermatol 2004;51 :660-2.
Ahmed, M. U.et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Altamirano, C., et al., "Strategies for fed batch cultivation of t-PA producing CHO cells: substitution of glucose and glutamine and rational design of culture medium", *J. Biotechn* 110:171-179, 2004.
Andersen DC, Goochee CF. The effect of cell-culture conditions on the oligosaccharide structures of secreted glycoproteins. Curr Opin Biotechnol. Oct. 1994;5(5):546-9.
Anonymous, "SACHEM Displacement Chromatography," Aug. 29, 2012, Retrieved from the internet //www.displacementchromatography.com>, retrieved on Jul. 30, 2014.
Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.
Averginos, Gab '04 Abstracts—GE Healthcare Life Sciences, "HUMIRA manufacturing: challenges and the path taken", France, Oct. 3-5, 2004, published 2005, pp. 14-16.
Avgerinos et al. (GAb '04 Abstracts—GE Healthcare Life Sciences, France Oct. 3-5, 2004, pp. 15-16 published 2005).
Awdeh, Z.L., A.R. Williamson, and B.A. Askonas, One cell-one immunoglobulin. Origin of limited heterogeneity of myeloma proteins. Biochem J. 1970. 116(2): p. 241-8.
Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.
Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.
Barbuto, J. et al. "Production of Neutralizing Antibodies to Tumor Necrosis Factor by Human Tumor-Infiltrating B Lymphocytes" *Proc. Am. Assoc. Cancer Res,.* 34:487, Abstr. 2904 (1993).
Barnes et al., "Stability of Protein Production from Recombinant Mammalian Cells," Biotechnology and Bioengineering, 81:6, Mar. 20, 2003, pp. 631-639.

BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf//www.bdbiosciences.com/external_files/Doc_Recon_2.0/ab/others/Phytone_Soytone.pdf>), (last accessed Jan. 8, 2015), 4 pages.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Biblia, T.A. et al., "In Pursuit of the Optimal Fed-Batch Process for Monoclonal Antibody Production", Biotechnol. Prog 11(1):1-13, Jan.-Feb. 1995.
Birch, Jr. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Biastoff, S.; et al.; Colorimetric Activity Measurement of a Recombinant Putrescine N-Methyltransferase from *Datura stramonium*; Planta Med. 2006, 72, 1136.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. *;455-458 (1997).
Bruggemann, M., Neuberger, M.S., "Strategies for expressing human antibody repertoires in transgenic mice," *Immunol. Today* 17:391-397 (1996).
Burteau et al. (In Vitro Cell Dev Biol—Animal, Jul. / Aug. 2003. 39-291-296).
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Carter et al., "Humanization of an anti-p185HER2 antibody for human cancer therapy," *Proc. Nat. Acad. Sci*89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Chang, T. & Wu, L., Methylglyoxal, oxidative street, and hypertension, Can. J. Physiol.Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.

(56) References Cited

OTHER PUBLICATIONS

Chaplen, F.W.R., Incidence and potential implications of the toxic metabolite methylglyoxal in cell culture: A review, Cytotechnology 26: 173-183, 1998.
Chaplen, FWR; A dissertation entitled Analysis of Methylglyoxal Metabolism in Mammalian Cell Culture; Univ. of Wisconsin-Madison 1996, 218 pages.
Charter, Edward A., "A New Process for the Separation and Purification of Egg Yolk; Antibodies," BASc., The University of British Columbia; A Thesis; Apr. 1993, 163 pages.
Chelius, D. et al.; Identification and Characterization of Deamidation Sites in the Conserved Regions of Human Immunoglobulin Gamma Antibodies, Anal. Chem. 2005, 77,6004-6011.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TND MAb) on TNFα, IL-1β, and IL-6 levels in patients with sepsis syndrome" Clinical Research, 42:2 299A (1994).
Chua, FKF et al., "Hyper-stimulation of monoclonal antibody production by high osmolarity stress in eRDF medium", J. Biotechnology 37(3);265-275, Nov. 15, 1994.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.
Chung et al., "Cetuximab-Induced Anaphylaxis and IgE Specific for Galactose-α-1, 3-Galactose", N. Engl. J. Med., 358:11, pp. 1109-1117 (2008).
Chung et al., "Utilization of Lysozyme Charge Ladders to Examine the Effects of Protein Surface; Charqe Distribution on Bindinq Affinity in Ion Exchanqe Systems," Lanqmuir 26(2): 759-768 (2010).
Cleland, J. et al., "A Specific Molar Ratio of Stabilizer to Protein is Required for Storage Stability of a Lyophilized Monoclonal Antibody," Journal of Pharmaceutical Sciences, vol. 90(3):310-321 (2001).
Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.
Cohen, J., et al., "Intersept: An international, multicenter, placebo-controlled trial of monoclonal anitbody to human tumor necrosis factor-α in patients with sepsis," Crit Care Med, vol. 24(9):1431-1440 (1996).
Cordoba, A.J., et al., Non-enzymatic hinge region fragmentation of antibodies in solution. Journal of Chromatography B, 2005. 818(2): p. 115-121.
Cox, J. et al. "A directory of human germ-line Vκ segments reveals a strong bias in their usage" Eur. J. Immunol., 24(2):827-36 (1994).
Cromwell (GAB'04 Abstracts—GE Healthcare Life Sciences, Franc Oct. 3-5, 2004, pp. 17-18 published 2005).
Crowell, C.K., et al., Amino acid and manganese supplementation modulates the glycosylation state of erythropoietin in a CHO culture system. Biotechnology and bioengineering, Feb. 15, 2007; 96(3):538-549.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
Daugherty, et al. Formulation and Delivery Issues for Monoclonal Antibody Therapeutics. Advanced Drug Delivery Reviews, 2006. vol. 58, pp. 686-706.

Davies et al., "Antibody VH domains as small recognition units." Biotechnology, 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
deZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Dolezal, et al., "Escherichia coli Expression of a Bifunctional Fab-peptide Epitope Reagent for the Rapid Diagnosis of HIV-1 and HIV-2", Immunotechnology, 1:197-209 (1995).
Doring, E., "Identification and Characterization of a TNFa Antagonist Derived from a Monoclonal Antibody" (1994) Mol. Immunol .31(14): 1059-1067.
Du et al., "Chromatographic analysis of the acidic and basic species of recombinant monoclonal antibodies" MAbs, Sep.-Oct. 2012; 4(5):578-85.
Elliot et al., "Repeated therapy with monoclonal antibody to tumour necrosis factor α (cA2) in patients with rheumatoid arthritis" (1994) Lancet, 344:1125-1127.
Elliot, "Treatment of rheumatoid arthritis with chimeric monoclonal antibodies to tumor necrosis factor α" (1993) Arthritis & Rheumatism, 36(12):1681-1690.
Ellison, Jay W. et al., "The Nucleotide Sequence of a Human Immunoglobulin Cγ1 Gene," Nucleic Acids Research, vol. 10, No. 13 (1982), 9 pages.
Emery, P. "Adalimumab therapy: Clinical findings and implications for integration into clinical guidelines for rheumatoid arthritis." Drugs of Today, 41(3): p. 155-153. (2005).
Erbitux (cetuximab) label, Revised Aug. 2013, 8 pages.
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Ewert et al., "Biophysical Properties of Human Antibody Variable Domains," J. Mol. Biol. 324: 531-553 (2003).
Exhibit dated Aug. 1, 2013 and cited by defendant in Civil Action No. 09-40089-FDS providing the Jun. 23, 2009 trial transcript of the PM session in the matter of Centocor, et al. v. Abbott Laboratories, 50 pages.
Exhibit dated Aug. 1, 2013 and cited by defendant in Civil Action No. 09-40089-FDS providing the trial transcript in the matter of Abbott Laboratories, et al. v. The Mathilda and Terrance Kennedy Institute, S.D.N.Y., 90 pages.
Exhibit dated Aug. 1, 2013 and cited by plaintiff in Civil Action No. 09-40089-FDS providing excerpts from the File History of U.S. Appl. No. 12/578,487, 5 pages.
Exhibit dated Aug. 1, 2013 and cited by defendant in Civil Action No. 09-40089-FDS providing the Jun. 24, 2009 trial transcript of the AM session in the matter of Centocor, et al. v. Abbott Laboratories, E.D. TX., 42 pages.
Exhibit dated Aug. 1, 2013 and cited by defendant in Civil Action No. 09-40089-FDS providing the Sep. 20, 2012 Day 8 trial transcript in the matter of Abbott v. Centocor Ortho Biotech Inc., D. MA., 71 pages.
Exhibit dated Aug. 1, 2013 and cited by plaintiff in Civil Action No. 09-40089-FDS providing Declaration by Jochen Salfeld, dated Jan. 17, 2013, 40 pages.
FDA Package insert for Adalimumab, Sep. 26, 2003, pp. 1-16.
Feldmann, "Anti-TNF-alpha Therapy of Rheumatoid Arthritis: What Have We Learned?" (2001) Annu. Rev. Immunol., 19:163-196.

(56) References Cited

OTHER PUBLICATIONS

Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Fleisher B., Mechanism of glycosylation in the Golgi apparatus. J Histochem Cytochem, Aug. 1983; 31(8):1033-1040.
Folk et al., "Carboxypeptidase B, Purification and Characterization of the Porcine Enzyme," J. Biological Chem, 1960, 235:2272-2277.
Fomsgaard, "Auto-antibodies to Tumor Necrosis Factor a in Healthy Humans and Patients with Inflammatory Diseases and Gram-Negative Bacterial Infections" (1989) *Scand. J. Immunol.* 30:219-23.
Foote, J., "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," *LC-GC* 11 (1):26-34 (1993).
Gatto, B. "Biologics targeted at TNF: design, production and challenges", Reumatismo 58(2):94-103, 2006.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).
Gonzalez et al. "Purification of Lactic Acid from Fermentation Broths by Ion-Exchange Resins" Ind. Eng. Chem. Res. 45:3243 (2006).
Goochee CF The Oligosaccharides of Glycoproteins: Bioprocess Factors Affecting Oligosaccharide Structure and their Effect on Glycoprotein Properties. Nature Biotechnology Dec. 1991 1346-1355.
Goswami et al., "Developments and Challenges for mAb-Based Therapeutics," *Antibodies*, 2:452-500, 2013.
Graf et al., "Ion exchange resins for the purification of monoclonal antibodies from animal cell culture" Bioseparation 4 (1) :7-20 (Feb. 1994). ;4 (1) :7-20.
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Gramer M J et al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.
Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grunberg, J. et al., "High-Yield Production of Recombinant Antibody Fragments in HEK-293 Cells Using Sodium Butyrate", BioTechniques 34(5):968-972, May 2003.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Harding et al., "Class switching in human immunoglobulin transgenic mice" (1995) *Ann. NY Acad. Sci.*, 764:536-547.
Harlow and Lane, Antibodies a Laboratory Manual, Purification of Antibodies by using a; Deae-matrix (Batch), Storing and Purifying Antibodies; Chapter 8: 302-303 (1988).
Harlow et al., Eds ("Antibodies: A Laboratory Manual" 1988. Cold Spring Harbor Laboratory Press, Chapter 7, pp. 245, 247,and 253).
Harris, "Processing of C-terminal lysine and arginine residues of proteins isolated from mammalian cell culture" Journal of Chromatography, (1995) 705; 129-134.
Harris, R.J., et al., Identification of multiple sources of charge heterogeneity in a recombinant antibody. Journal of Chromatography B: Biomedical Sciences and Applications, 2001. 752(2): p. 233-245.
Harris, Reed J. et al., "Structural Characterization of a Recombinant CD4-IgG Hybrid Molecule," Eur. J. Biochem. 194:611-620 (1990).
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hills, A.E. et al., Metabolic control of recombinant monoclonal antibody N-glycosylation in GS-NS0 cells, Biotechnology and Bioengineering, Oct. 20, 2001; 75(2):239-251.
Hipkiss, A.; Can the beneficial effects of methionine restriction in rats be explained in part by decreased methylglyoxal generation resulting from suppressed carbohydrate metabolism?; Biogerontology 2012, 13, 633-636.
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor -alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(1 1):484-490 (2003).
Hoogenboom et al., "By-passing immunisation : Human antibodies from synthetic repertoires of germline VH gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler et al., "Optimal and consistent protein glycosylation in mammalian cell culture", Glycobiology; (2009), 19(9):936-949.

(56) References Cited

OTHER PUBLICATIONS

Hossler et al.; "Improvement of mammalian cell culture performance through surfactant enabled concentrated feed media"; Biotechnology Progress; 29(4):1023-1033 (2013).
http://www.cygnustechnologies.com/product_detail/host-cell-protein-antibodies/anti-cho-h . . . CYGNUS Technologies, Anti-CHO HCP (Apr. 18, 2012), 1 page.
Huang et al. "Effects of anti-TNF monoclonal antibody infusion in patients with hairy cell leukaemia" (1992) *Br. J. Haematol.*, 81(2):231-234.
Huang, L., et al., In Vivo Deamidation Characterization of Monoclonal Antibody by LC/MS/MS. Analytical Chemistry, 2005. 77(5): p. 1432-1439.
Humira (adalimumab) label, Revised Sep. 2013, 87 pages.
Humira (adalimumab) prescribing information, Dec. 20, 2002, pp. 1-16.
Huse, "Generation of a large combinatorial library of the immunoglobulin repertoire in phage lambda" (1989) *Science*, 246:1275-81.
HyClone™ CDM4CHO Catalog listing (last accessed Nov. 17, 2014).
ICH Topic Q6B "Specifications:Test Procedures and Acceptance Criteria for Biotechnological/Biological Products," Sep. 1999, pp. 1-17.
International Preliminary Report on Patentability for Application No. PCT/US07/08359, dated Dec. 12, 2011, 5 pages.
International Preliminary Report on Patentability for Application No. PCT/US2011/060388, dated May 30, 2012, 9 pages.
International Preliminary Report on Patentability for Application No. PCT/US2013/031352 dated Nov. 25, 2014, pp. 1-10.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for Application No. PCT/US2013/031380, dated Feb. 5, 2014, 162 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report for Application No. PCT/US2014/026606, Dated Dec. 8, 2014, 8 pages.
International Search Report for Application No. PCT/US2014/026636, Dated Jul. 29, 2014, 5 pages.
International Search Report from PCT/US2014/024256 dated Jul. 30, 2014, pp. 1-15.
Invitation to Pay Additional Fees for International Application No. PCT/US2013/031380, Dated Nov. 28, 2013, 5 pages.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jack, M.; Wright, D.; The Role of Advanced Glycation Endproducts and Glyoxalase I in Diabetic Peripheral Sensory Neuropathy; Transl. Res. 2012, 159, 355-365.
Jakobovits, A., "Production of fully human antibodies by transgenic mice" (1995) *Curr. Op. Biotechnol.*, 6:561-566.
Jakubowski, H., Protein N-homocysteinylation: implications for atherosclerosis. Biomedicine; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Jefferis, R., Glycosylation of Recombinant Antibody Therapeutics. Biotechnology Progress, 2005.21(1): p. 11-16.
Jespers, "Guiding the Selection of Human Antibodies from Phage Display Repertoires to a Single Epitope of an Antigen" (1994) *Bio/Technology*, 12:899-903.
Johnson et al., "Characterization of cathepsin L secreted by Sf21 insect cells", Archives of Biochemistry and Biophysics (2005), 444:7-14.
Johnson, K.A., et al., Cation exchange HPLC and mass spectrometry reveal C-terminal amidation of an IgG1 heavy chain. Analytical Biochemistry, 2007. 360(1): p. 75-83.
Kalyanpur, M., "Downstream Processing in the Biotechnology Industry" Molecular Biotechnology, vol. 22:87-98 (2002).
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Karampetsou et al., "Tnf-α antagonists beyond approved indications: stories of success and prospects for the future", Q J Med (2010) 103:917-928.
Kaschak et al: "Characterization of the basic charge variants of a human IgGl: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor -alpha monoclonal antibody" (2000) *Ann. Rheum. Dis.*, 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGl: Isolation, characterization, in vitro binding properties and pharmacokinetics in rats", MABS, vol. 2, No. 6, Nov. 1, 2010, pp. 613-624.
Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.

(56) References Cited

OTHER PUBLICATIONS

Kim, Ns. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.

Kingkeohoi, S. & Chaplen, F.W.R., Analysis of methylglyoxal metabolism in CHO cells grown in culture, Cytotechnology (2005) 48:1-13.

Knight et al., "Construction and initial characterization of a mouse-human chimeric anti-TNF antibody" (1993) *Mol. Immunol.*, 30(16):1443-1453.

Kopaciewicz et al., "Retention Model for High-Performance Ion-Exchange Chromatography,"; Journal of Chromatography, 266:3-21 (1983).

Kwon et al., "Production of lactic acid by *Lactobacillus rhamnosus* with vitamin-suppremented soybean hydrolysate", Enzyme Microb Technol. (2000), 26:209-215.

Lerner, "Antibodies without immunization" (1992) *Science*, 258:1313-1314.

Leusch, "Failure to demonstrate TNFα-specific autoantibodies in human sera by ELISA and Western blot" (1991) *J. Immunol. Methods*, 139:145-47.

Lewis, "Use of alanine scanning mutagenesis to improve the affinity of an anti gp120 (HIV) antibody" (1994) *J. Cell. Biochem.*, 18D:215.

Li et al., "Cell Culture Processes for Monoclonal Antibody Production," mAbs, 2:5, 466-477, Sep./Oct. 2010.

Li, F. et al., "Current Therapeutic Antibody Production and Process Optimization" BioProcessing Journal, vol. 4(5):23-30 (2005).

Li, Feng, et al., "Cell Culture Processes for Monoclonal Antibody Production," mAbs 2:5, 466-479 (Sep.-Oct. 2010).

Lifely et al., "Glycosylation and Biological Activity of CAMPATH-1H Expressed in Different Cell Lines and Grown Under Different Culture Conditions", *Glycobiology*, 5(8):813-822 (1995).

Liu et al., "Recovery and purification process development for monoclonal antibody production," MABS (2010) 2(5):480-499.

Liu, H., et al., Heterogeneity of monoclonal antibodies. Journal of Pharmaceutical Sciences, 2008. 97(7): p. 2426-2447.

Liu, H., Gaza-Bulseco, G., & Lundell, E., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.

Liu, M, et al.; Discovery of Undefined Protein Cross-Linking Chemistry: A Comprehensive Methodology Utilizing 18O-Labeling and Mass Spectrometry; Anal. Chem. 2013, 5900-5908.

Liu, M.et al.; Protein Isoaspartate Methyltransferase-Mediated 18O-Labeling of Isoaspartic Acid for Mass Spectrometry Analysis; Anal. Chem. 2011, 84, 1056-1062.

Lo, T.W. et al., Binding and modification of proteins by methylglyoxal under physiological conditions. A kinetic and mechanistic study with N alpha-acetylarginine, N alpha-acetyilysine, and N alpha-acetyllysine, and bovine serum albumin, Dec. 23, 1994, The Journal of Biological Chemistry, 269, 32299-32305.

Logan, John S. "Transgenic Animals: Beyond 'Funny Milk'", *Current Opinion in Biotechnology*, 4:591-595 (1993).

Lonberg et al., "Antigen-specific human antibodies from mice comprising four distinct genetic modifications" (1994) *Nature*, 368:856-859.

Lonberg et al., "Human Antibodies from Transgenic Mice" (1995) *Int. Rev. Immunol.*, 13:65-93.

Low et al., "Mimicking Somatic Hypermutation: Affinity Maturation of Antibodies Displayed on Bacteriophage Using a Bacterial Mutator Strain" (1996) *J. Mol. Biol.*, 260:359-368.

Low, Nigel: thesis extract (1996) *Cambridge University*.

Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.

Luo et al., "Understanding of C-terminal lysine variants in antibody production using mammalian cells" Abstract of papers, ACS, Anaheim, CA, US, Mar. 2011, 1 page.

Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.

Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.

Ma, et al., "Generation and Assembly of Secretory Antibodies in Plants", *Science*, 268:716-719 (1995).

Maeda, et al., "Analysis of Nonhuman N-Glycans as the Minor Constituents in Recombinant Monoclonal Antibody Pharmaceuticals", *Anal. Chem.*, 84:2373-2379 (2012).

Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".

Manning, M., et al., *Stability of Protein Pharmaceuticals: An Update*. Pharmaceutical Research, 2010.27(4): p. 544-575.

Marks et al., "Human antibody fragments specific for human blood group antigens from a phage display library" (1993) *Bio/Technology*, 11:1145-1150.

Marks et al., "Molecular evolution of proteins on filamentous phage. Mimicking the strategy of the immune system" (1992) *J. Biol. Chem.* 267:16007-16010.

Marks, "By-passing immunization: Human antibodies from V-gene libraries displayed on phage" (1991) *J. Mol. Biol.*, 222:581-597.

Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.

Marks, JD., "By-Passing Immunization: Building High Affinity Human Antibodies by Chain Shuffling" (1992) *Biotechnology*, 10:779-783.

Martin, A.C.R. "Accessing the Kabat antibody sequence database by computer" (1996)*PROTEINS: Structure, Function and Genetics*, 25:130-133.

Martinelle, K. et al., "Effect of different cell culture medium surfactants on cell growth and viability", Cells and Culture, Proceedings of the 20th ESACT Meeting v4 819-822, Jun. 17-20, 2007.

Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.

McAtee et al., "Isolation of monoclonal antibody charge variants by displacement chromatography," Current Protocols in Protein Science, 8.10-8.10.13, 2012.

Medynski, "Phage Display: All Dressed Up and Ready to Role" (1994) *Bio/Technology*, 12:1134-1136.

Mendez et al., "Functional transplant of megabase human immunoglobulin loci recapitulates human antibody response in mice" (1997) *Nature Genetics*, 15:146-156.

Meuwly, F. et al., "Conversion of a CHO cell culture process from perfusion to fed-batch technology without altering product quality", J.Biotechn. 123:106-116, 2006.

Miller et al. "Characterization of site-specific glycation during process development of a human therapeutic monoclonal antibody" Journal of Pharmaceutical Sciences, vol. 100, No. 7, Jul. 2011, 2543-2550.

Millipore, "Pellicon 2 Filters and Holders," 2003, pp. 1-8.

Mizuochi, T., et al., Structural and numerical variations of the carbohydrate moiety of immunoglobulin G. J Immunol, 1982. 129(5): p. 2016-20.

Moore, A., et al., "Effects of temperature shift on cell cycle, apoptosis and nucleotide pools in CHO cell batch cultures", Cytotechnology, 23:47-54, 1997.

Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.

Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.

(56) References Cited

OTHER PUBLICATIONS

Möller, Monoclonal antibodies to human tumor necrosis factor α: in vitro and vivo application (1990) *Cytokine*, 2(3):162-69.
Neuberger M. et al., "Mice perform a human repertoire" (1997) *Nature*, 386:25-26.
Ngo et al., "Kosmotropes enhance the yield of antibody purified by affinity chromatography using immobilized bacterial immunoglobulin binding proteins," Journal of Immunoassay & Immunochemistry, (2008) 29(1):105-115.
Ni, W.; Analysis of Isoaspartic Acid by Selective Proteolysis with Asp-N and Electron Transfer Dissociation Mass Spectrometry; Anal. Chem. 2010, 82,7485-7491.
Nilsson, "Antibody engineering" (1995) *Current Opinion in Structural Biology*, 5:450-456.
Nogal, B., Chhiba, K. and Emery, J. C. (2012), Select host cell proteins coelute with monoclonal antibodies in protein a chromatography. Biotechnol Progress, 28: 454-458.
Noguchi et al., "Failure of Human Immunoresponse to N-Glycolylneuraminic Acid Epitope Contained in Recombinant Human Erythropoietin", *Nephron*, 72:599-603 (1996).
Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).
Oh et al., "Effect of N-Acetylcystein on Butyrate-Treated Chinese Hamster Ovary Cells to Improve the Production of Recombinant Human Interferon-β-1α", Biotechnol. Prog. 21(4):1154-1164, 2005.
Oh, D-K. et al., "Increased erythritol production in fed-batch cultures of *Torula* sp. by controlling glucose concentration", J. Industrial Microb. & Biotechn. 26(4): 248-252, 2001.
Oh, SKW, et al., "Substantial Overproduction of Antibodies by Applying Osmotic Pressure and Sodium Butyrate", Biotechn. Bioengin. 42(5):601-610, 1993.
Osbourn, "From rodent reagents to human therapeutics using antibody guided selection" (2005) *Methods*, 36(1):61-68.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation-what affect high mannose 5 glycoform", Biotechnology and Bioengineering vol. 108, No. Oct. 10, 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trands in Biotechnology.
Parekh, R.B., et al., Association of rheumatoid arthritis and primary osteoarthritis with changes in the glycosylation pattern of total serum IgG. Nature, 1985. 316(6027): p. 452-7.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
PCT/US2013/069702 International Search Report & Written Opinion mailed Jan. 31, 2014, 13 pages.
Perchiacca et al., "Aggregation-resistance domain antibodies engineered with charged mutations; near the edges of the complementarity-determining regions," Protein Engineering Design & Selection, 25: 10 (591-601) 2012.
Perkins, M.; et. al. Determination of the Origin of Charge Heterogeneity in a Murine Monoclonal Antibody; M. Pharm. Res. 2000, 17, 1110-1117.
Pietersz et al., "In vitro and in vivo Antitumor Activity of a Chimeric anti-CD19 Antibody", *Cancer Immunol. Immunother.*, 41:53-60 (1995).

Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.
Potter et al., "Antibody Production in the Baculovirus Expression System", *Intern. Rev. Immunol.*, 10:103-112 (1993).
Poul et al., "Design of Cassette Baculovirus Vectors for the Production of Therapeutic Antibodies in Insect Cells", *Immunotechnology*, 1:189-196 (1995).
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Queen, C., "A humanized antibody that binds to the interleukin 2 receptor" (1989) *Proc. Natl. Acad. Sci. USA*, 86(24):10029-10033.
Rabbani, N.; Thornalley, P. J.; Glyoxalase in diabetes, obesity and related disorders; Semin. Cell Dev. Biol. 2011, 22, 309-317.
Rader et al. "A phage display approach to rapid antibody humanization: Designed combinatorial V gene libraries" (1998) *Proc Natl Acad Sci USA*, 95:8910-8915.
Raju, TS. "Glycosylation Variations with Expression Systems and Their Impact on Biological Activity of Therapeutic Immunoglobulins", *BioProcess International.*, 44-53 (2003).
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Reichert JM., et al., "Monoclonal antibody successes in the clinic", Nature Biotech. 23(9):1073-1078, 2005.
Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Rheinwald JG, et al., "Growth of Cultured Mammalian Cells on Secondary Glucose Sources", Cell, 287-293, 1974.
Ridder et al., "Generation of Rabbit Monoclonal Antibody Fragments from a Combinatorial Phage Display Library and Their Production in Yeast *Pichia pastoris*", Biotechnology, 13:255-260 (1995).
Riechmann, "Phage display and selection of a site-directed randomized single-chain antibody Fv fragment for its affinity improvement" (1993) *Biochemistry*, 32(34):8848-8855.
Routier, F. H. et al.: "The glycosylation pattern of a humanized IgGl antibody(D1.3) expressed in CHO cells", Glycoconjugate Journal, Chapman & Hall, GB, vol. 14, No. 2, Jan. 1, 1997, pp. 201-207.
Roy, B.M., et al., Toxic concentrations of exogenously supplied methy!glyoxal in hybridoma cell culture, Cytotechnology (2004) 46:97-107.
Rube et al., "Ewing's sarcoma and peripheral primitive neuroectodermal tumor cells produce large quantities of bioactive tumor necrosis factor-α (TNF-α) after radiation exposure", Int. J. Radiation Oncology Biol. Phys., (2003), vol. 56, No. 5, pp. 1414-1425.
Rudikoff et al., "Single amino acid substitution altering antigen-binding specificity" (1982) *Proc. Natl. Acad. Sci. USA*, 70:1979-1983.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.

(56) References Cited

OTHER PUBLICATIONS

Sandhu, J. "Protein engineering of antibodies" (1992) *Critical Reviews in Biotechnology*, 12:437-462.
Santora et aL, "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.
Sato et al, "Stimulation of monoclonal antibody production by human-human hybridoma cells with an elevated concentration of potassium or sodium phosphate in serum-free medium," Cytotechnology 2:63-67, 1989.
Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Saxena, R. K. et al.; Microbial production and applications of 1,2-propanediol; Indian J. Microbiol. 2010,50,2-11.
Schiestl et al. "Acceptable changes in quality attributes of glycosylated biopharmaceuticals" Nature Biotechnology, 29(4), 310-312 (2011).
Schwieterman, "Immunosuppression in Combination with Monoclonal Antibodies" in Biologic Agents in Autoimmune Disease (Mar. 2-4, 1995), 9 pages.
Senczuk et al. "Hydrophobic interaction chromatography in dual salt system increases protein binding capacity" Biotechnology and Bioengieering, 103(5), 930-935 (2009).
Seresht et al., "The impact of phosphate scarcity on pharmaceutical protein production in *S. cerevisiae*: linking transcriptomic insights to phenotypic responses" Microbial Cell Factories. 2011, 10: 104.
Sheeley et al., "Characterization of Monoclonal Antibody Glycosylation: Comparison of Expression Systems and Identification of Terminal α-Linked Galactose", *Anal. Biochem.*, 247(1):102-110 (1997).
Sheikh et al., "Studies of the digestion of bradykinin, lysyl bradykinin, and kinin-degradation products by carboxypeptidases A, B, and N;". Biochemical Pharmacology. 1986, 35: 1957-1963.
Shen, Amy Y. et al., "Recombinant DNA Technology and Cell Line Development," from "Cell Culture Technology for Pharmaceutical and Cell-Based Therapies," CRC Press, 1995, 15-40.
Shih, "Effects of Anions on the Deamidation of Soy Protein". Journal of Food Science. 1991, 56: 452-454.
Shukla et al., "Host cell protein clearance during protein A chromatography: development of an improved column wash step," Biotechnology Progress, (2008) 24(5):1115-1121.
Shukla et al., "Recent advances in large-scale production of monoclonal antibodies and related proteins," Trends in Biotechnology, (2010) 28(5):253-261.
Sigma Catalog "RPMI1640" (last accessed Jan. 22, 2015), 3 pages.
Sigma MSDS for RMPI1640 (last accessed Jan. 22, 2015), 6 pages.
Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.
Sundaram et al., "An innovative approach for the characterization of the isoforms of a monoclonal antibody product," Mabs, 3(6):505-512, 2011.
Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.
Takagi, M. et al., "The effect of osmolarity on metabolism and morphology in adhesion and suspension chinese hamster ovary cells producing tissue plasminogen activator", Cytochnology 32:171-179, 2000.
Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.
Tan et al., "Expression and purification of a secreted functional mouse/human chimaeric antibody against bacterial endotoxin in baculovirus-infected insect cells", Biotechnol. Appl. Biochem. (1999), 30:59-64.
Taylor et al.,"Human immunoglobulin transgenes undergo rearrangement, somatic mutation and class switching in mice that lack endogenous IgM" (1994) *Int. Immunol.*, 6:579-591.
Teichmann, S. Declaration dated Dec. 17, 2010 from opposition proceedings in EP 0929578, 6 pages.
Tess database "HYCLONE" Trademark #76244963. Filing date Apr. 23, 2001. Live mark. Last accessed Jan. 21, 2015.
Tess database "HYCLONE" Trademark #85769283. Filing date Sep. 30, 2012. Live mark. Last accessed Jan. 21, 2015.
Tharmalingam et al.; "Pluronic Enhances the Robustness and Reduces the Cell Attachment of Mammalian Cells"; Molecular Biotechnology; 39(2):167-177 (2008).
The Kennedy Institute of Rheumatology, 1995 Annual Scientific Report, "Anti-TNF trials and studies of mechanisms of action".
The MW Calculator available at the Sequence Manipulation Suite (see bioinformatics.org/sms2/index.html), downloaded Feb. 25, 2014, 2 pages.
The pI Calculator available at the Sequence Manipulation Suite (see bioinformatics.org/sms2/index.html>), downloaded Feb. 25, 2014, p. 1).
The Statement on a Nonproprietary Name Adopted by the USAN Council for Adalimumab, p. 1, downloaded on May 19, 2011 from http://www.ama-assn.org/resources/doc/usan/adalimumab.doc. 1 page.
Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.
Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.
Tomiya et al., "Comparing N-glycan processing in mammalian cell lines to native and engineered; lepidopteran insect cell lines," Glycoconjuqate Journal 21 :343-360 (2004).
Tomlinson, "The repertoire of human germline VH sequences reveals about fifty groups of VH segments with different hypervariable loops" (1992) *J. Mol. Biol.*, 227:776-98.
Tomlinson, "The structural repertoire of the human Vk domain" (1995) *The EMBO J.*, 14(18):4628-38.
Tracey, "Tumor necrosis factor: A pleiotropic cytokine and therapeutic target" (1994) *Annu. Rev. Med.*, 45:491-503.
Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.
United States Food and Drug Administration (FDA) Biological Licensing Application File No. 125057 (Adalimumab) (Dec. 31, 2002) (Last Accessed Mar. 4, 2015 at //www.fda.gov/Drugs/DevelopmentApprovalProcess/HowDrugsareDevelopedandApproved/ApprovalApplications/TherapeuticBiologicApplications/ucm080610.htm>), 1 page.
Vallee B et al. "The role of zinc in carboxypeptidase" The Journal of Biological Chemistry, (1960) 235, 1; 64-69.
Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).
Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.

(56) References Cited

OTHER PUBLICATIONS

Van Lent PL, et al. "The impact of protein size and charge on its retention in articular cartilage" J Rheumatol. Aug. 1987;14(4):798-805.
Varasteh et al. Optimization of Anti-Rh D Immunoglobulin Stability in the Lyphiliization Process. Iranian Journal of Basic Medical Sciences, Spring 2008, vol. 11, No. 1. pp. 55-61.
Vasilli, P., Annu. Rev. Immunol. 10:411-452 (1992); and Tracey, K. J. and Cerami, A. Annu. Rev. Med. 45:491-503 (1994).
Vaughan, "Human antibodies by design" (1998) *Nature Biotechnology*, 16:535-539.
Vlasak, J. & Ionescu, R., *Heterogeneity of Monoclonal Antibodies Revealed by Charge-Sensitive Methods*. Current Pharmaceutical Biotechnology, 2008. 9(6): p. 468-481.
Wagner et al., "Antibodies generated from human immunoglobulin miniloci in transgenic mice" (1994) *Nucl. Acids Res*. 22:1389-1393.
Wagner et al., "The diversity of antigen-specific monoclonal antibodies from transgenic mice bearing human immunoglobulin gene miniloci" (1994) *Eur. J. Immunol.*, 24:2672-2681.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Ward, "Binding activities of a repertoire of single immunoglobulin variable domains secreted from *Escherichia coli*" (1989) *Nature*, 341:544-546.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Wedemayer et al., "Structural insights into the evolution of an antibody combining site" (1997) *Science*, 276:1665-1669.
Wiendl et al., "Therapeutic Approaches in Multiple Sclerosis. Lessons from failed and interrupted treatment trials", BioDrugs. (2002), 16(3):183-200.
Williams et al., "Kinetic analysis by stopped-flow radiationless energy transfer studies: effect of anions on the activity of carboxypeptidase A". Biochemistry. 1986, 25, 94-100.
Williams, A. et al., Ion-Exchange Chromatography, Oct. 1998, Supplement 44, pp. 10-10-1-10-10-30.
Winter, "Humanized antibodies" (1993) *Immunol. Today*, 14(6):243-246.
Winter, "Making antibodies by phage display technology" (1994) *Annu. Rev. Immunol.*, 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2,Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yigzaw et al., "Exploitation of the adsorptive properties of depth filters for host cell protein removal during monoclonal antibody purification," Biotechnology Progress, (2006) 22(1):288-296.
Yuk, I.H. et al., Controlling Glycation of Recombinant Antibody in Fed Batch Cell Cultures, Nov. 2011, Biotechnoloqy and Bioenqineerinq, vol. 108, No. 11 pp. 2600-2610.
Yumioka et al., "Screening of effective column rinse solvent for Protein-A chromatography," Protein Expression and Purification, (2010), 70(2): 218-223.
Zang, T.; et al.; Chemical Methods for the Detection of Protein N-Homocysteinylation via Selective Reactions with Aldehydes; Anal. Chem. 2009, 81, 9065-9071.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al., "Isolation and characterization of charge variants using cation exchange displacement chromatography," 1218(31): 5079-5086, 2011.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Zou et al., "Dominant expression of a 1.3 Mb human Ig kappa locus replacing mouse light chain production" (1996) *FASEB J.*, 10:1227-1232.
Babcock, James et al., "Partial Replacement of Chemically Defined Media with Plant-Derived Protein Hydrolysates," *BioPharm International*, vol. 23: 6. Jun. 2010, 6 pages.
Bandyopadhyay S., et al. Physicochemical and functional characterization of a biosimilar adalimumab ZRC-3197, Biosimilars, 2015;5, pp. 1-18.
Brock, Jonathan et al., "Detection and identification of arginine modifications on methylglyoxal-modified ribonuclease by mass spectrometric analysis," Journal of Mass Spectrometry, 2007; 42: 89-100.
Drew, Berry et al., "The Effects of Media Formulations on the Biochemical Profile of IgG Expressed in Sp2/0 Cells as Measured by Cation Exchange HPLC," European Society of Animal Cell Technology Meeting Jan. 2007, Poster #1115, 1 page.
Extended European Search Report for Application No. 13877986.3. Dated Aug. 4, 2014, 11 pages.
Gao et al. "Site-selective modifications of arginine residues in human hemoglobin induced by methylglyoxal." Biochemistry, 2006; pp. 15654-15660.
Grosvenor, Sally, "A New Era in Cell Culture Media Development," *BioPharm International*, Jul. 2012 vol. 25: 7, 7 pages.
Hossler, Patrick et al., "Targeted Shifting of Protein Glycosylation Profiles in Mammalian Cell Culture through Media Supplementation of Cobalt." *J. Glycobiol* vol. 3; 1.(2014). 9 pages.
International Preliminary Report on Patentability for Application No. PCT/US2013/031380, dated Sep. 15, 2015, 13 pages.
International Preliminary Report on Patentability for Application No. PCT/US2013/065720, dated Sep. 24, 2015, 8 pages.
International Preliminary Report on Patentability for Application No. PCT/US2013/065749 dated Sep. 15, 2015, 10 pages.
International Preliminary Report on Patentability for Application No. PCT/US2013/065797, dated Sep. 24, 2015, 8 pages.
International Preliminary Report on Patentability for Application No. PCT/US2013/069702, dated Sep. 15, 2015, 8 pages.
International Preliminary Report on Patentability for Application No. PCT/US2014/024151, dated Sep. 15, 2015, 9 pages.
International Preliminary Report on Patentability for Application No. PCT/US2014/024256, dated Sep. 15, 2015, pp. 1-9.
International Preliminary Report on Patentability for Application No. PCT/US2014/026606, dated Sep. 15, 2015, 13 pages.
International Preliminary Report on Patentability for Application No. PCT/US2014/026636, dated Sep. 15, 2015, 9 pages.
International Search Report for Application No. PCT/US2015/038819 Dated Sep. 2, 2015, 12 pages.

(56) References Cited

OTHER PUBLICATIONS

Mehta, et al. "Purifying therapeutic monoclonal antibodies," Chemical Engineering Progress; May 2008, 104, 5; pp. S14-S20.

Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.

Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.

Roe, S. "Separation Based on Structure" Chapter 4, § 5.2, In, Protein Purification Methods; A Practical Approach, Harries, et al. Sep. 1989, p. 203.

Sargent (pp. 1-3, Internet Archive captured Aug. 28, 2013, www.cellculturedish.com/2012/01 /cho-cells-the-top-expressionsystem-of-best-selling-biologic-drugs/).

Scientific Discussion. Retrieved from the Internet: www.ema.europa.eu/dics/en_GB/document_library/EPAR_Sceintific_Discussion/human/00481/WC500050867.pdf [retrieved on Jun. 29, 2015], EMEA, 2004, 25 pages.

Shirato, Ken et al., "Hypoxic regulation of glycosylation via the N-acetylglucosamine cycle." *J. Clin. Biochem. Nutr.* vol. 48; 1 (2011). 20-25.

Wang, Tina et al., "Exploring Post-translational Arginine Modification Using Chemically Synthesized Methylglyoxal Hydroimidazolones," *J. Am. Chem. Soc.*, 2012, 134, pp. 8958-8967.

Zhang, Y. et al., "Specificity and Mechanism of Metal Ion Activation in UDP-galactose: $\beta$-Galactoside-$\alpha$-1,3-galactosyltransferase." *J. Biological Chemistry* vol. 276; 15 (2001). 11567-11574.

Goochee, C.F. "Bioprocess Factors Affecting Glycoprotein Oligosaccharide Structure." *Develop. Biol. Standard*, vol. 76 (1992). 95-104.

Indian Patent Office—IPAIRS application status for 2285/MUM/2013—Application not yet published. Document found on internet at ipindiaonline.gov/in/patentsearch/search/index.aspx. Last accessed Apr. 13, 2015.

International Search Report and Written Opinion from PCT/US2015/039773 dated Sep. 25, 2015, pp. 1-14.

Roy, Samar N. et al., "Secretion of Biologically Active Recombinant Fibrinogen by Yeast." *The Journal of Biological Chemistry*, vol. 270; 40 (1995). 23761-23767.

Seo, Jin Seok, et al., "Effect of culture pH on recombinant antibody production by a new human cell line, F2N78, grown in suspension at 33.0 °C and 37.0° C," *Appl. Microbiol Biotechnol.*, vol. 97 (2013). 5283-5291.

\* cited by examiner

| Condition (no. of runs) | %NGA2F+ (NGA2F-GlcNAc) | % NA1F+NA2F | %Man5+Man6 |
|---|---|---|---|
| Control: Y/P =1.55 (n=5) | 75.87 ± 1.04 | 17.54 ± 0.91 | 6.59 ± 0.39 |
| Y/P = 0.67 (n=5) | 74.31 ± 0.73 | 18.32 ± 0.41 | 7.35 ± 0.63 |
| Y/P = 0.25 (n=5) | 72.75 ± 0.91 | 19.07 ± 0.54 | 8.29 ± 0.94 |

Fig. 11

| Condition (no. of runs) | %NGA2F+ (NGA2F-GlcNAc) | % NA1F+NA2F | %Man5+Man6 |
|---|---|---|---|
| Control: Y/P =1.55 (n=6) | 77.49 ± 0.34 | 15.55 ± 0.62 | 6.95 ± 0.30 |
| Y/P = 0.67 (n=6) | 75.40 ± 0.14 | 17.97 ± 0.18 | 6.64 ± 0.13 |

| Experiment Block # | Hydrolysate Name | Hydrolysate Vendor / Catalog Number | Concentration in adaptation media (g/kg) | Concentration in production media (g/kg) |
|---|---|---|---|---|
| I | Bacto TC Yeastolate | BD Biosciences / 255772 | 2 | 2, 5, 11 |
| | BBL Phytone Peptone | BD Biosciences / 211096 | 2 | 2, 4, 7, 10, 15 |
| | Wheat Peptone E1 | Organotechnie / 19559 | 2 | 2, 4, 7, 10, 15 |
| II | BBL Phytone Peptone | BD Biosciences / 211096 | 2 | 10, 15 |
| | Wheat Peptone E1 | Organotechnie / 19559 | 2 | 10, 15 |

Fig. 40

| Media/Vendor/Catalog Number | Hydrolysates/Vendor/Catalog Number | Concentration in adaptation media (g/kg) | Concentration in production media (g/kg) |
|---|---|---|---|
| OptiCHO / Life Sciences Gibco/12681-011 GIA-1 / Life Sciences Gibco / Custom formulation CDM4CHO / HyClone / SH30558.02 IS CHO-CD / Irvine Scientific / 91119 | Bacto TC Yeastolate / BD Biosciences / 255772 BBL Phytone Peptone / BD Biosciences / 211096 | 4.0 (TC Yeastolate) 2.6 (Phytone Peptone) | 10.7 (TC Yeastolate) 6.9 (Phytone Peptone) |

Fig. 41

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 5, 11 |
| HyPep Yeast Extract | Sheffield/Kerry Biosciences | 2 | 5, 11 |
| UF Yeast Hydrolysate | Irvine Scientific / 292804 | 2 | 5, 11 |
| BBL Phytone Peptone | BD Biosciences / 211096 | 2 | 4, 7 |
| HyPep 1510 | Sheffield/Kerry Biosciences / 5x59053 | 2 | 4, 7 |
| SE50 MAF-UF | DMV International / SE50 MAF-UF | 2 | 4, 7 |
| UF Soy Hydrolysate | Irvine Scientific / 96857 | 2 | 4, 7 |
| Wheat Peptone E1 | Organotechnie / 19559 | 2 | 4, 7 |
| HyPep 4601 | Sheffield/Kerry Biosciences / 5z10419 | 2 | 4, 7 |
| Proyield WGE80M Wheat | DMV International / WGE80M | 2 | 4, 7 |

Fig. 42

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5 |
| BBL Phytone Peptone | BD Biosciences / 211096 | 2 | 4, 7 |
| Wheat Peptone E1 | Organotechnie / 19559 | 2 | 4, 7 |

Fig. 43

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 4, 7, 15 |
| Wheat Peptone E1 | Organotechnie / 19559 | 2 | 4, 7, 10 |

Fig. 44

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 4, 7, 15 |
| Wheat Peptone E1 | Organotechnie / 19559 | 2 | 4, 7, 15 |

Fig. 45

| Hydrolysate Name | Hydrolysate Vendor and Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 2, 4, 7 |
| Wheat Peptone E1 | Organotechnie / 19559 | 2 | 2, 4, 7 |

Fig. 46

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 2, 4, 7 |
| Wheat Peptone E1 | Organotechnie / 19559 | 2 | 2, 4, 7 |

Fig. 47

| Experimental ID | Bacto TC Yeastolate (BD Biosciences / 255772) (g/L) | BBL Phytone Peptone (BD Biosciences / 211096) (g/L) | Wheat Peptone E1 (Organotechnie / 19559) (g/L) |
|---|---|---|---|
| 1 (control) | 0 | 0 | 0 |
| 2 | 2 | 0 | 0 |
| 3 | 0 | 2 | 0 |
| 4 | 0 | 0 | 2 |
| 5 | 2 | 2 | 0 |
| 6 | 2 | 0 | 2 |
| 7 | 0 | 2 | 2 |
| 8 | 2 | 2 | 2 |

Fig. 48

| Experimental ID | Bacto TC Yeastolate (BD Biosciences / 255772) (g/L) | BBL Phytone Peptone (BD Biosciences / 211096) (g/L) | Wheat Peptone E1 (Organotechnie / 19559) (g/L) |
|---|---|---|---|
| 1 (control) | 0 | 0 | 0 |
| 2 | 5 | 0 | 0 |
| 3 | 0 | 4 | 0 |
| 4 | 0 | 0 | 4 |
| 5 | 5 | 4 | 0 |
| 6 | 5 | 0 | 4 |
| 7 | 0 | 4 | 4 |
| 8 | 5 | 4 | 4 |

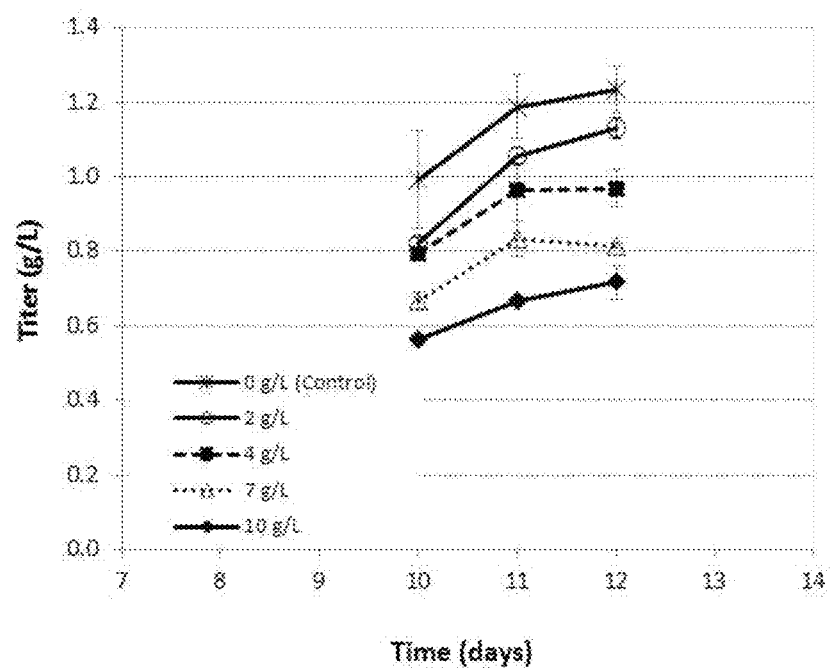

US 9,290,568 B2

METHODS TO CONTROL PROTEIN HETEROGENEITY

CROSS REFERENCE TO RELATED APPLICATIONS

The present application claims priority to U.S. application Ser. No. 14/194,305, filed Feb. 28, 2014, which claims priority to U.S. application Ser. No. 13/804,220, filed Mar. 14, 2013, which claims priority to U.S. Provisional Application No. 61/696,219, filed Sep. 2, 2012, the disclosures of each of which are incorporated by reference herein in their entireties.

FIELD OF THE INVENTION

The instant invention relates to the field of protein production and in particular to processes for controlling and limiting the heterogeneity of proteins expressed in host cells.

BACKGROUND OF THE INVENTION

The production of proteins for biopharmaceutical applications typically involves the use of cell cultures that are known to produce proteins exhibiting varying levels of heterogeneity. The basis for such heterogeneity includes, but is not limited to, the presence of distinct glycosylation substitution patterns. For example, such heterogeneity can be observed in variations in the fraction of proteins substituted with agalactosyl fucosylated biantennary oligosaccharides NGA2F and NGA2F-GlcNAc and in the fraction of proteins substituted with galactose-containing fucosylated biantennary oligosaccharides NA1F and NA2F.

Technological advances in recombinant protein production analysis have provided unique opportunities for identifying the extent of heterogeneity exhibited by a particular protein population, particularly in the context of large-scale production of recombinant proteins. Although such advances have allowed for the robust characterization of protein heterogeneity, challenges continue to exist to identify methods for producing proteins with desirable heterogeneity. Control of protein heterogeneity is particularly advantageous in the context of cell culture processes used for commercially produced recombinant bio-therapeutics as such heterogeneity has the potential to impact therapeutic utility. The instant invention addresses this need by providing compositions and processes to control protein heterogeneity.

SUMMARY OF THE INVENTION

The present invention is directed to methods for controlling oligosaccharide distribution in a recombinantly-expressed protein sample and to recombinantly-expressed proteins having defined oligosaccharide distribution.

In one aspect, the invention is directed to a method for controlling the oligosaccharide distribution of a recombinantly-expressed protein sample including supplementing a cell culture medium used in the recombinant expression of said protein with a yeast hydrolysate and/or a plant hydrolysate. In a related embodiment, the recombinantly-expressed protein is an antibody or an antigen binding portion thereof. For example, the antibody may be an anti-TNFα antibody, such as adalimumab.

In related embodiments, the yeast hydrolysate is selected from the group consisting of Bacto TC Yeastolate, HyPep Yeast Extract and UF Yeast Hydrolysate. In certain embodiments the plant hydrolysate is selected from the group consisting of a soy hydrolysate, a wheat hydrolysate, a rice hydrolysate, a cotton seed hydrolysate, a pea hydrolysate, a corn hydrolysate and a potato hydrolysate. For example, the plant hydrolysate may be selected from the group consisting of BBL Phytone Peptone, HyPep 1510, SE50 MAF-UF, UF Soy Hydrolysate, Wheat Peptone E1, HyPep 4601 and Proyield WGE80M Wheat.

In certain embodiments, the cell culture medium is supplemented with yeast hydrolysate to achieve a yeast hydrolysate concentration from about 2 g/L to about 11 g/L. Alternatively, the cell culture medium is supplemented with yeast hydrolysate to achieve a yeast hydrolysate concentration of about 2 g/L, 5 g/L or 11 g/L. Alternatively or in combination, the cell culture medium is supplemented with plant hydrolysate to achieve a plant hydrolysate concentration from about 2 g/L to about 15 g/L. In further related embodiments, the cell culture medium is supplemented with plant hydrolysate to achieve a plant hydrolysate concentration of about 2 g/L, 4 g/L, 7 g/L, 10 g/L or 15 g/L.

In certain embodiments of the invention, the cell culture medium is supplemented with yeast hydrolysate and plant hydrolysate to achieve a yeast hydrolysate to plant hydrolysate ratio of about 0.1 to about 4.0. For example, the cell culture medium is supplemented with yeast hydrolysate and plant hydrolysate to achieve a yeast hydrolysate to plant hydrolysate ratio of about 0.25 to about 1.55.

In one embodiment, the recombinantly-expressed protein sample is produced by a CHO cell line.

In certain embodiments, supplementing the cell culture medium with yeast hydrolysate and/or plant hydrolysate decreases the percentage of oligosaccharides NGA2F and (NGA2F-GlcNAc) present in the protein sample. For example, supplementing the cell culture medium with yeast hydrolysate and/or plant hydrolysate decreases the percentage of oligosaccharides NGA2F and (NGA2F-GlcNAc) by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30%. Alternatively or in combination, supplementing the cell culture medium with yeast hydrolysate and/or plant hydrolysate decreases the percentage of oligosaccharides NGA2F and (NGA2F-GlcNAc) by about 1%-30%, 2%-25%, 5%-20% or 5%-15%. Alternatively or in combination, supplementing the cell culture medium with yeast hydrolysate and/or plant hydrolysate decreases the percentage of oligosaccharides NGA2F and (NGA2F-GlcNAc) in the protein sample to about 64%-88%, 70%-88% or 75%-85%.

In certain embodiments, supplementing the cell culture medium with yeast hydrolysate and/or plant hydrolysate increases the percentage of oligosaccharides NA1F and NA2F present in the protein sample. For example, supplementing the cell culture medium with yeast hydrolysate and/or plant hydrolysate increases the percentage of oligosaccharides NA1F and NA2F by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30%.

Alternatively or in combination, supplementing the cell culture medium with yeast hydrolysate and/or plant hydrolysate increases the percentage of oligosaccharides NA1F and NA2F by about 1%-30%, 2%-25%, 5%-20% or 5%-15%. In certain embodiments, supplementing the cell culture medium with yeast hydrolysate and/or plant hydrolysate increases the percentage of oligosaccharides NA1F and NA2F in the protein sample to about 8%-31%, 10%-25% or 10%-20%.

In certain embodiments, the cell culture medium comprises yeast and/or plant hydrolysate prior to supplementing the medium with the yeast hydrolysate and/or plant hydrolysate. In other embodiments, the cell culture medium is substantially free of yeast and/or plant hydrolysate prior to supplementing the medium with the yeast hydrolysate and/or plant hydrolysate.

In another aspect, the present invention is directed to a method for controlling the oligosaccharide distribution of a recombinantly-expressed protein sample including modulating the asparagine and/or glutamine concentration of the cell culture medium used in the recombinant expression of said protein. In a particular embodiment, the recombinantly-expressed protein sample is an antibody or an antigen binding portion thereof, for example, an anti-TNFα antibody such as adalimumab.

In various embodiments, the recombinantly-expressed protein is produced in a CHO cell line.

In certain embodiments, the method includes modulating the concentration of glutamine and asparagine. For example, the method may include increasing the concentration of asparagine. Alternatively or in combination, the method includes increasing the concentration of glutamine. In a particular embodiment, the concentration of asparagine and/or glutamine in the cell culture medium is modulated to a level of greater than about 0.2 g/L. Alternatively, the concentration of asparagine and/or glutamine in the cell culture medium is modulated to a level of greater than about 0.4 g/L, 0.6 g/L, 0.8 g/L, 1.0 g/L, 1.2 g/L, 1.4 g/L, 1.6 g/L, 1.8 g/L or 2 g/L. In related embodiments, the concentration of asparagine and/or glutamine in the cell culture medium is modulated to a level between about 0.4 g/L-1.4 g/L.

In certain embodiments, the cell culture medium includes a hydrolysate, for example, a yeast hydrolysate and/or a plant hydrolysate. In a particular embodiment, the yeast hydrolysate is selected from the group consisting of Bacto TC Yeastolate, HyPep Yeast Extract and UF Yeast Hydrolysate. In a particular embodiment, the plant hydrolysate is selected from the group consisting of a soy hydrolysate, a wheat hydrolysate, a rice hydrolysate, a cotton seed hydrolysate, a pea hydrolysate, a corn hydrolysate and a potato hydrolysate. For example, the plant hydrolysate may be selected from the group consisting of BBL Phytone Peptone, HyPep 1510, SE50 MAF-UF, UF Soy Hydrolysate, Wheat Peptone E1, HyPep 4601 and Proyield WGE80M Wheat.

In certain embodiments, an increase in the concentration of asparagine and/or glutamine in the cell culture medium increases the percentage of oligosaccharides NGA2F and (NGA2F-GlcNAc) present in the protein sample. For example, an increase in the concentration of asparagine and/or glutamine in the cell culture medium increases the percentage of oligosaccharides NGA2F and (NGA2F-GlcNAc) by at least about 0.1%, 0.2%, 0.3%. 0.4%, 0.5%, 0.6%, 0.7%, 0.8%, 0.9%, 1%, 1.5%, 2%, 2.5%, 3.0%, 3.5%, 4.0%, 4.5%, 5%, 6%, 7%, 8%, 9%, 10%, 15% or 20%. Alternatively or in combination, an increase in the concentration of asparagine and/or glutamine in the cell culture medium increases the percentage of oligosaccharides NGA2F and (NGA2F-GlcNAc) by about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 11%, 12%, 13%, 14% or 15%. Alternatively or in combination, an increase in the concentration of asparagine and/or glutamine in the cell culture medium increases the percentage of oligosaccharides NGA2F and (NGA2F-GlcNAc) by about 0.5%-15%, by about 0.5%-10% or by about 4-6%.

In certain embodiments, an increase in the concentration of asparagine and/or glutamine in the cell culture medium decreases the percentage of oligosaccharides NA1F and NA2F present in the protein sample generated by the cell line. For example, an increase in the concentration of asparagine and/or glutamine in the cell culture medium decreases the percentage of oligosaccharides NA1F and NA2F by at least about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 11%, 12%, 13%, 14% or 15%. In a particular embodiment, an increase in the concentration of asparagine and/or glutamine in the cell culture medium decreases the percentage of oligosaccharides NA1F and NA2F by about 0.5%-10%, by about 0.5%-6% or by about 2-5%.

In certain embodiments, the cell culture medium includes asparagine and/or glutamine prior to modulating the concentration of asparagine and/or glutamine. In another embodiment, the cell culture medium is substantially free of asparagine and/or glutamine prior to modulating the concentration of asparagine and/or glutamine.

According to another aspect of the invention, a composition including the recombinantly-expressed protein produced by any of the foregoing methods is provided. For example, the protein may be an anti-TNFα antibody such as adalimumab, or an antigen binding portion thereof.

In one aspect, a pharmaceutical composition including the recombinantly-expressed protein produced by any of the foregoing methods is provided. For example, the protein may be an anti-TNFα antibody such as adalimumab, or an antigen binding portion thereof.

In another aspect, the present invention is directed to a composition including N-linked glycosylated adalimumab, such that the oligosaccharides NGA2F and (NGA2F-GlcNAc) are present at about 64%-88% and/or such that the oligosaccharides NA1F and NA2F are present at about 8-31%, based on the total amount of oligosaccharides present in the composition. For example, the oligosaccharides NGA2F and (NGA2F-GlcNAc) may be present at about 70%-88% or at about 75%-85%. Alternatively or in combination, the oligosaccharides NA1F and NA2F are present at about 10%-25% or at about 10%-20%.

In yet another aspect, the present invention is directed to a pharmaceutical composition including N-linked glycosylated adalimumab and a pharmaceutically acceptable excipient, such that the oligosaccharides NGA2F and (NGA2F-GlcNAc) are present at about 64%-88% and/or such that the oligosaccharides NA1F and NA2F are present at about 8-31%, based on the total amount of oligosaccharides present in the composition. For example, the oligosaccharides NGA2F and (NGA2F-GlcNAc) may be present at about 70%-88% or at about 75%-85%.

Alternatively or in combination, the oligosaccharides NA1F and NA2F are present at about 10%-25% or at about 10%-20%.

BRIEF DESCRIPTION OF THE DRAWINGS

FIG. 11 depicts the glycosylation profile in Example 4: Hydrolysate Study #1 in adalimumab-producing CHO cell line #1.

FIG. 12 depicts the glycosylation profile in Example 4: Hydrolysate Study #2 in adalimumab-producing CHO cell line #1.

FIG. 39 depicts the experimental design for Example 1.
FIG. 40 depicts the experimental design for Example 2.
FIG. 41 depicts the experimental design for Example 3.
FIG. 42 depicts the experimental design for Example 6.
FIG. 43 depicts the experimental design for Example 7.
FIG. 44 depicts the experimental design for Example 8.
FIG. 45 depicts the experimental design for Example 9.
FIG. 46 depicts the experimental design for Example 10.
FIG. 47 depicts the experimental design for Example 11 (adaptation stage).
FIG. 48 depicts the experimental design for Example 11 (production stage).

FIGS. 49A-49C depict the effect of pea hydrolysate addition to CD media GIA-1 in adalimumab-producing CHO cell line #1 on Culture growth (FIG. 49A), Culture viability (FIG. 49B) and Harvest titer (FIG. 49C), respectively.

DETAILED DESCRIPTION

Figure 1A:
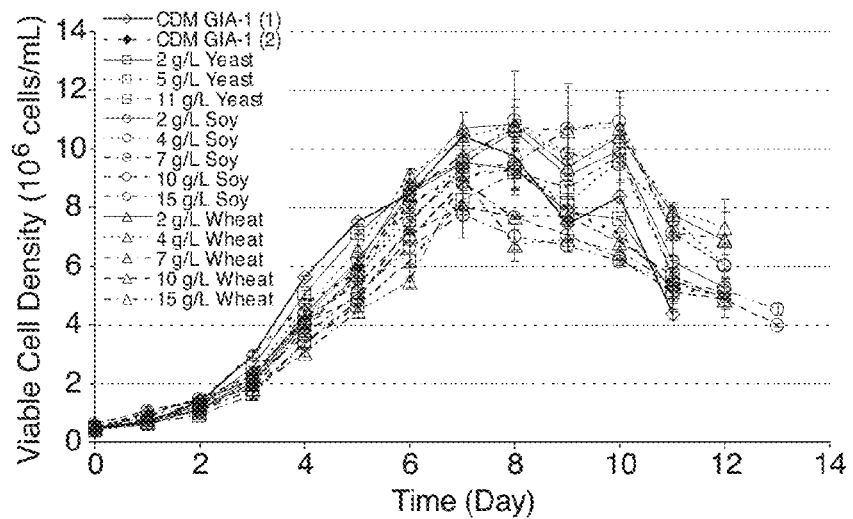
FIGS. 1A-1C depict the effect of yeast, soy or wheat hydrolysate addition to CDM GIA-1 in adalimumab-producing CHO cell line #1 on (FIG. 1A) Culture growth, (FIG. 1B) Culture viability and (FIG. 1C) Harvest titer, respectively.

The present invention is directed to compositions and methods for controlling protein heterogeneity arising in a population of recombinantly expressed proteins. The present invention is predicated, at least in part, on the discovery that controlling the concentration of hydrolysates, asparagine and/or glutamine in a cell culture medium allows for control over the oligosaccharide distribution of a recombinantly-expressed protein produced therein.

For example, in one aspect, the present invention provides a method for controlling the oligosaccharide distribution of a recombinantly-expressed protein sample by supplementing the cell culture medium with a yeast hydrolysate and/or a plant hydrolysate. In certain embodiments, supplementing the cell culture medium with yeast hydrolysate and/or plant hydrolysate decreases the percentage of oligosaccharides NGA2F and (NGA2F-GlcNAc) present in the protein sample. Alternatively or in combination, supplementing the cell culture medium with yeast hydrolysate and/or plant hydrolysate increases the percentage of oligosaccharides NA1F and NA2F present in the protein sample.

In another aspect, the method for controlling the oligosaccharide distribution of the recombinantly-expressed protein sample includes modulating the asparagine and/or glutamine concentration of the cell culture medium used in the recombinant expression of the protein. In certain embodiments, an increase in the concentration of asparagine and/or glutamine in the cell culture medium increases the percentage of oligosaccharides NGA2F and (NGA2F-GlcNAc) present in the protein sample. Alternatively or in combination, an increase in the concentration of asparagine and/or glutamine in the cell culture medium decreases the percentage of oligosaccharides NA1F and NA2F present in the protein sample generated by the cell line.

In another aspect, the present invention is directed to a protein produced by such methods and having the desired oligosaccharide distribution or pharmaceutical compositions including such protein. In particular, the present invention provides a composition comprising N-linked glycosylated adalimumab, wherein the oligosaccharides NGA2F and (NGA2F-GlcNAc) are present at about 64%-88% and/or wherein the oligosaccharides NA1F and NA2F are present at about 8-31%, based on the total amount of oligosaccharides present in the composition.

Consistency in the quality of the glycoproteins is important because glycosylation may impact protein solubility, activity and circulatory half-life. (Gawlitzek et al., Effect of Different Cell Culture Conditions on the Polypeptide Integrity and N-glycosylation of a Recombinant Model Glycoprotein. Biotechnol. Bioeng. 1995; 46:536-544; and Hayter et al., Glucose-limited Chemostat Culture of Chinese Hamster Ovary Cells Producing Recombinant Human Interferon-γ. Biotechnol. Bioeng. 1992; 39:327-335).

Definitions

Unless otherwise defined herein, scientific and technical terms used in connection with the present invention shall have the meanings that are commonly understood by those of ordinary skill in the art. The meaning and scope of the terms should be clear. However, in the event of any latent ambiguity, definitions provided herein take precedent over any dictionary or extrinsic definition. Further, unless otherwise required by context, singular terms, for example, those characterized by "a" or "an", shall include pluralities. In this application, the use of "or" means "and/or", unless stated otherwise. Furthermore, the use of the term "including," as well as other forms of the term, such as "includes" and "included", is not limiting. Also, terms such as "element" or "component" encompass both elements and components comprising one unit and elements and components that comprise more than one unit unless specifically stated otherwise.

The term "protein of interest", as used herein refers to a target protein, production and controlled glycosylation of which is desired. In various embodiments, the protein of interest is an antibody or an antigen-binding fragment thereof, a soluble protein, a membrane protein, a structural protein, a ribosomal protein, an enzyme, a zymogen, a cell surface receptor protein, a transcription regulatory protein, a translation regulatory protein, a chromatin protein, a hormone, a cell cycle regulatory protein, a G protein, a neuroactive peptide, an immunoregulatory protein, a blood component protein, an ion gate protein, a heat shock protein, an antibiotic resistance protein, a functional fragment of any of the preceding proteins, an epitope-containing fragment of any of the preceding proteins and combinations thereof. In a particular embodiment, the protein of interest is a monomer.

In a particular embodiment, the protein of interest is an antibody or an antigen binding portion thereof. The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains: CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody", as used herein, also includes alternative antibody and antibody-like structures, such as, but not limited to, dual variable domain antibodies (DVD-Ig).

The term "antigen-binding portion" of an antibody (or "antibody portion") includes fragments of an antibody that retain the ability to specifically bind to an antigen (e.g., hIL-12, hTNFα or hIL-18). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody may be part of a larger immunoadhesion molecule, formed by covalent or non-covalent association of the antibody with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The term "human antibody" includes antibodies having variable and constant regions corresponding to human germline immunoglobulin sequences as described by Kabat et al. (See Kabat et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D. et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A. et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may bind TNFα molecules from other species. Moreover, an isolated antibody may be substantially free of other cellular material and/or chemicals. A suitable anti-TNFα antibody is Adalimumab (AbbVie, Illinois USA).

As used herein, the term "adalimumab," also known by its trade name HUMIRA® (AbbVie, Illinois, USA) refers to a human IgG1 antibody that binds human tumor necrosis factor α (TNFα). In general, the heavy chain constant domain 2 (CH2) of the adalimumab IgG-Fc region is glycosylated through covalent attachment of oligosaccharide at asparagine 297 (Asn-297). The light chain variable region of adalimumab is provided herein as SEQ ID NO:1 and the heavy chain variable region of adalimumab is provided herein as SEQ ID NO:2. Adalimumab comprises a light chain variable region comprising a CDR1 of SEQ ID NO:7, a CDR2 of SEQ ID NO:5 and a CDR3 of SEQ ID NO:3. Adalimumab comprises a heavy chain variable region comprising a CDR1 of SEQ ID NO:8, a CDR2 of SEQ ID NO:6 and CDR3 of SEQ ID NO:4. The nucleic acid sequence of the light chain variable region is set forth in SEQ ID NO:9. The nucleic acid sequence of the heavy chain variable region is set forth in SEQ ID NO:10. The full length amino acid sequence of the light chain is set forth as SEQ ID NO:11 and the full length amino acid sequence of the heavy chain is set forth as SEQ ID NO:12. Adalimumab is described in U.S. Pat. Nos. 6,090,382; 6,258,562; 6,509,015; 7,223,394; 7,541,031; 7,588,761; 7,863,426; 7,919,264; 8,197,813; 8,206,714; 8,216,583; 8,420,081; 8,092,998; 8,093,045; 8,187,836; 8,372,400; 8,034,906; 8,436,149; 8,231,876; 8,414,894; 8,372,401, the entire contents of each which are expressly incorporated herein by reference in their entireties. Adalimumab is also described in the "Highlights of Prescribing Information" for HUMIRA® (adalimumab) Injection (Revised January 2008) the contents of which are hereby incorporated herein by reference.

In one embodiment, adalimumab dissociates from human TNFα with a Kd of $1 \times 10^{-8}$ M or less and a Koff rate constant of $1 \times 10^{-3}$ s$^{-1}$ or less, both determined by surface plasmon resonance and neutralizes human TNFα cytotoxicity in a standard in vitro L929 assay with an IC50 of $1 \times 10^{-7}$ M or less. In another embodiment, adalimumab dissociates from human TNFα with a Koff of $5 \times 10^{-4}$ s$^{-1}$ or less or even more preferably, with a Koff of $1 \times 10^{-4}$ s$^{-1}$ or less. In still another embodiment, adalimumab neutralizes human TNFα cytotoxicity in a standard in vitro L929 assay with an IC50 of $1 \times 10^{-8}$ M or less, an IC50 of $1 \times 10^{-9}$ M or less or an IC50 of $1 \times 10^{-10}$ M or less. The term "Koff", as used herein, is intended to refer to the off rate constant for dissociation of an antibody from the antibody/antigen complex.

As used herein, the term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. In certain embodiments, the host cell is employed in the context of a cell culture.

As used herein, the term "cell culture" refers to methods and techniques employed to generate and maintain a population of host cells capable of producing a recombinant protein of interest, as well as the methods and techniques for optimizing the production and collection of the protein of interest. For example, once an expression vector has been incorporated into an appropriate host, the host can be maintained under conditions suitable for high level expression of the relevant nucleotide coding sequences and the collection and purification of the desired recombinant protein. Mammalian cells are preferred for expression and production of the recombinant of the present invention; however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. Other, non-limiting, examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

The term "cell culture medium" as used herein refers to a combination of elements in which cells are cultured and which provide nutrients for the growth of the cells. A cell culture medium typically contains a mixture of defined nutrients dissolved in a buffered physiological saline solution. At a basic level, a cell culture medium contain salts, amino acids, sugar, vitamins and other organic nutrients. Such medium may be used as a starting point for the addition of various supplements, e.g., serum (such as fetal bovine serum) and antibiotics to generate a complete growth medium.

As used herein a "recombinant expression vector" can be any suitable recombinant expression vector and can be used to transform or transfect any suitable host. For example, one of ordinary skill in the art would appreciate that transformation or transfection is a process by which exogenous nucleic acid such as DNA is introduced into a cell wherein the transformation or transfection process involves contacting the cell with the exogenous nucleic acid such as the recombinant expression vector as described herein. Non-limiting examples of such expression vectors are the pUC series of vectors (Fermentas Life Sciences), the pBluescript series of vectors (Stratagene, LaJolla, Calif.), the pET series of vectors (Novagen, Madison, Wis.), the pGEX series of vectors (Pharmacia Biotech, Uppsala, Sweden) and the pEX series vectors (Clontech, Palo Alto, Calif.).

As used herein, the term "recombinant protein" refers to a protein produced as the result of the transcription and translation of a gene carried on a recombinant expression vector that has been introduced into a host cell. In certain embodiments the recombinant protein is an antibody or an antigen binding portion thereof.

As used herein, the term "glycosylation" refers to the addition of a carbohydrate to an amino acid. Such addition commonly, although not exclusively, occurs via a nitrogen of asparagine or arginine ("N-linked" glycosylation) or to the hydroxy oxygen of serine, threonine, tyrosine, hydroxylysine or hydroxyproline side-chains ("O-linked" glycosylation). In eukaryotes, N-linked glycosylation occurs on the asparagine of the consensus sequence Asn-Xaa-Ser/Thr, in which Xaa is any amino acid except proline (Komfeld et al., Ann Rev Biochem 54: 631-664 (1985); Kukuruzinska et al, Proc. Natl. Acad. Sci. USA 84: 2145-2149 (1987); Herscovics et al, FASEB J. 7:540-550 (1993); and Orlean, *Saccharomyces* Vol. 3 (1996)). 0-linked glycosylation also takes place at serine or threonine residues (Tanner et al., Biochim. Biophys. Acta. 906: 81-91 (1987); and Hounsell et al, Glycoconj. J. 13: 19-26 (1996)). However, other glycosylation patterns can be formed, e.g., by linking glycosylphosphatidyl-inositol to the carboxyl-terminal carboxyl group of a protein.

Figure 51:
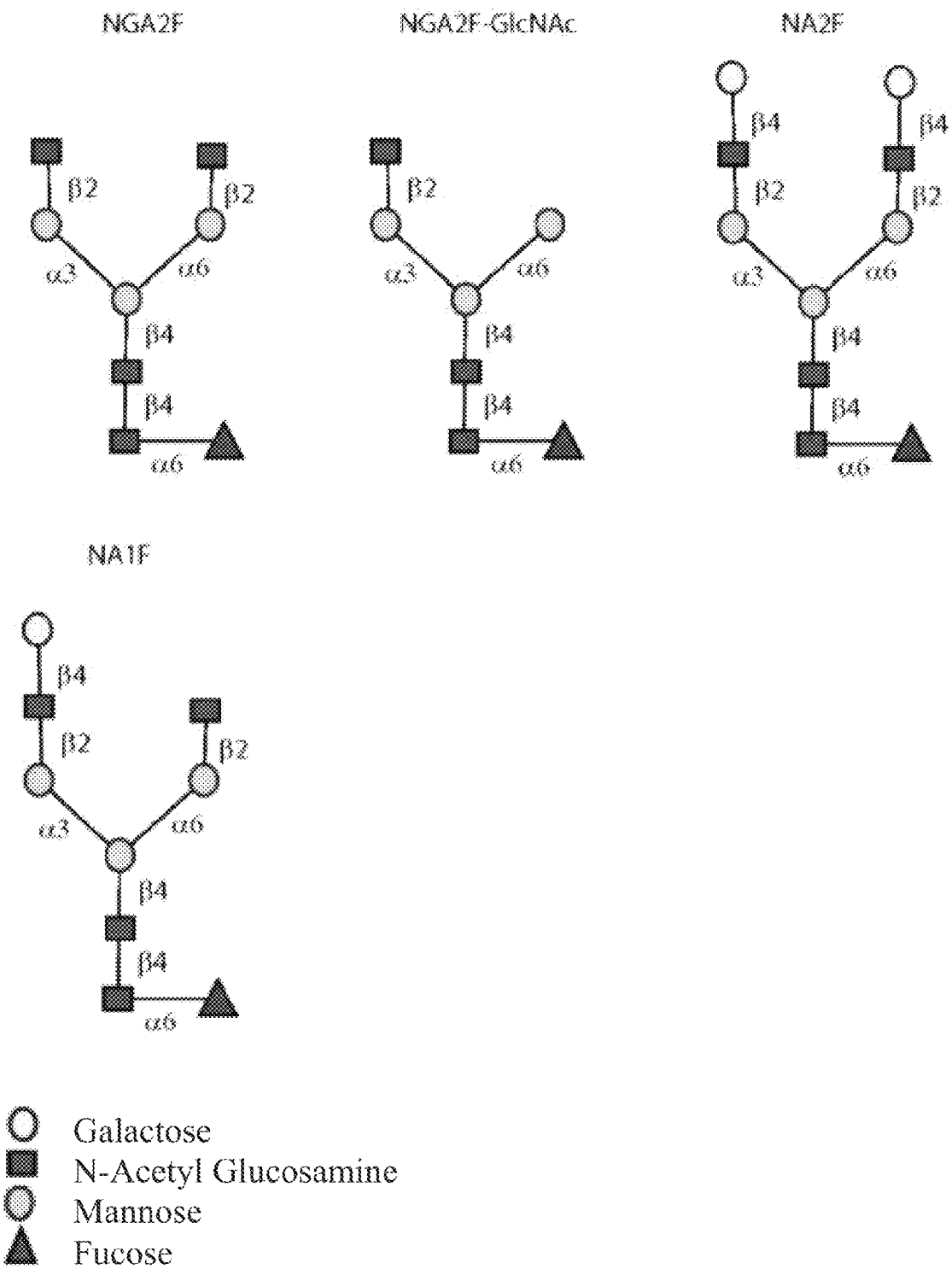
FIG. 51 depicts the structures of oligosaccharides NGA2F, (NGA2F-GlcNac), NA1F and NA2F.

In particular embodiments, proteins of the invention are glycosylated by the addition of NGA2F and (NGA2F-GlcNac) oligosaccharides. As used herein, the term "NGA2F" refers to an oligosaccharide having the N-linked glycan common core pentasaccharide Man3GlcNAc2, further containing an N-acetylglucosamine linked to each one of the two branched mannose residues of the core and also containing a fucose linked to the GlcNAc residue proximal to the asparagine residue of the N-linked glycosylated protein. The term "NGA2F-GlcNAc" as used herein is an oligosaccharide having the N-linked glycan common core pentasaccharide Man3GlcNAc2, further containing one N-acetylglucosamine linked one of the two branched mannose residues of the core and also containing a fucose linked to the GlcNAc residue proximal to the asparagine residue of the N-linked glycosylated protein. The structures of each of NGA2F and (NGA2F-GlcNac) are set forth in FIG. 51.

Alternatively or in combination, proteins of the invention are glycosylated by the addition of NA2F and NA1F oligosaccharides. The term "NA2F" as used herein is an oligosaccharide having the N-linked glycan common core pentasaccharide Man3GlcNAc2, further containing: an N-acetylglucosamine linked to each one of the two branched mannose residues of the core, a fucose linked to the GlcNAc residue proximal to the asparagine residue of the N-linked glycosylated protein and a galactose linked to each N-acetylglucosamine linked to a branched mannose. The term "NA1F" as used herein is an oligosaccharide having the N-linked glycan common core pentasaccharide Man3GlcNAc2, further containing: an N-acetylglucosamine linked to each one of the two branched mannose residue of the core, a fucose linked to the GlcNAc residue proximal to the asparagine residue of the N-linked glycosylated protein and a galactose linked to one of the two N-acetylglucosamine residues linked to a branched mannose. The structures of each of NA2F and NA1F are set forth in FIG. 51.

As used herein, the term "oligosaccharide distribution" as used herein refers to the relative amounts of oligosaccharides found in a sample of glycosylated proteins. For example, oligosaccharide distribution may refer to the relative amounts of N-linked oligosaccharides, i.e., NGA2F and NGA2F-GlcNac oligosaccharides and NA2F and NA1F oligosaccharides found in a sample. According to the methods of the present invention, the oligosaccharide distribution can be controlled, for example, by supplementing cell culture medium with hydrolysates or by modulating the asparagine and/or glutamine concentration. As used herein, the term "controlled protein heterogeneity" refers to a composition derived from the methods of the present invention having a desired oligosaccharide distribution, for example, a desired ratio of N-linked oligosaccharides NGA2F and NGA2F-GlcNac oligosaccharides as compared to NA2F and NA1F oligosaccharides.

The term "control", as used herein, is intended to refer to both limitation as well as to modulation. For example, in certain embodiments, the instant invention provides methods for controlling diversity that decrease the diversity of certain characteristics of protein populations and, in particular, glycosylation patterns. Such decreases in diversity can occur by: (1) promotion of a desired characteristic, e.g., a favorable glycosylation pattern; (2) inhibition of an unwanted characteristic, e.g., a disfavored glycosylation pattern; or (3) a combination of the foregoing. As used herein, the term "control" also embraces contexts where heterogeneity is modulated, i.e., shifted, from one diverse population to a second population of equal or even greater diversity, where the second population exhibits a distinct profile of the characteristic of interest. For example, in certain embodiments, the methods of the instant invention can be used to modulate the types of oligosaccharide substitutions present on proteins from a first population of substitutions to a second equally diverse, but distinct, population of substitutions.

In certain embodiments, the heterogeneity corresponds to the glycosylation state of individual members of a population of proteins. In certain embodiments, control is exerted over the type of glycosylation substitutions present on individual members of a population of proteins. In certain embodiments, control is exerted over the extent of glycosylation substitutions present on individual members of a population of proteins. In certain embodiments, control is exerted over both the type and extent of glycosylation substitutions present on individual members of a population of proteins. In certain embodiments, such control results in a decrease in the amount of NGA2F and NGA2F-GlcNac oligosaccharides and/or an increase in the amount of NA1F and NA2F oligosaccharides linked to the protein of interest. In certain embodiments, such control results in an increase in the amount of NGA2F and NGA2F-GlcNac oligosaccharides and/or a decrease in the amount of NA1F and NA2F oligosaccharides linked to the protein of interest.

In certain embodiments, control over protein glycosylation heterogeneity is exerted by employing specific hydrolysates during production of the protein of interest, for example, but not by way of limitation, in cell culture media supplemented with hydrolysates. In certain embodiments, control over protein glycosylation heterogeneity is exerted by maintaining certain yeastolate to phytone ratios during production of the protein of interest. In certain embodiments, control over protein glycosylation heterogeneity is exerted by the addition of asparagine and/or glutamine during the production of the protein of interest.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

Control of Protein Heterogeneity
Supplementation of CD Media with Yeast and/or Plant Hydrolysates The experiments disclosed herein demonstrate that, in certain embodiments, supplementation of CD cell culture media with yeast and/or plant hydrolysates can modulate product quality of a mAb by, in certain embodiments, decreasing the NGA2F and NGA2F-GlcNac oligosaccharides and, in certain embodiments, increasing the NA1F and NA2F oligosaccharides. These results were achieved in multiple CD media available from multiple vendors (Life Sciences Gibco, HyClone and Irvine Scientific), using yeast and/or plant hydrolysates (for example, but not by way of limitation, soy, wheat, rice, cotton seed, pea, corn and potato) from multiple vendors (BD Biosciences organotechnie, Sheffield/Kerry Biosciences, Irvine Scientific and DMV International). In experiments where yeast or plant hydrolysates were added individually, a dose-dependent effect in the extent of reduction of NGA2F and NGA2F-GlcNac oligosaccharides (and a corresponding increase in the NA1F and NA2F oligosaccharides) with increasing yeast or plant hydrolysates concentration in culture CD media was observed. For example, but not by way of limitation, yeast hydrolysates can be used to supplement a CD cell culture media at concentrations ranging from about 1 g/L to about 25 g/L, about 1 g/L to about 15 g/L or about 2 g/L to about 11 g/L to achieve the desired reduction of NGA2F and NGA2F-GlcNac oligosaccharides and a corresponding increase in the NA1F and NA2F oligosaccharides. In certain non-limiting embodiments, yeast hydrolysates can be used to supplement a CD cell culture media at concentrations of about 2 g/L, about 5 g/L or about 11 g/L. In certain non-limiting embodiments, plant hydrolysates can be used to supplement a CD cell culture media at concentrations ranging from about 1 g/L to about 30 g/L, about 1 g/L to about 20 g/L or about 2 g/L to about 15 g/L to achieve the desired reduction of NGA2F and NGA2F-GlcNac oligosaccharides and a corresponding increase in the NA1F and NA2F oligosaccharides. In certain non-limiting embodiments, plant hydrolysates can be used to supplement a CD cell culture media at concentrations of about 2 g/L, about 4 g/L, about 7 g/L, about 10 g/L or about 15 g/L.

In a particular embodiment, the plant hydrolysate may be a soy hydrolysate. In certain non-limiting embodiments, soy hydrolysates can be used to supplement a cell culture media at concentrations ranging from about 1 g/L to about 30 g/L, about 1 g/L to about 20 g/L or about 2 g/L to about 15 g/L to achieve the desired reduction of NGA2F and NGA2F-GlcNac oligosaccharides and a corresponding increase in the NA1F and NA2F oligosaccharides.

In another embodiment, the plant hydrolysate may be a pea hydrolysate. In certain non-limiting embodiments, pea hydrolysates can be used to supplement a cell culture media at concentrations ranging from about 1 g/L to about 25 g/L, about 1 g/L to about 15 g/L or about 2 g/L to about 10 g/L to achieve the desired reduction of NGA2F and NGA2F-GlcNac oligosaccharides and a corresponding increase in the NA1F and NA2F oligosaccharides.

In a particular embodiment, the plant hydrolysate may be a wheat hydrolysate. In certain non-limiting embodiments, wheat hydrolysates can be used to supplement a cell culture media at concentrations ranging from about 1 g/L to about 30 g/L, about 1 g/L to about 20 g/L or about 2 g/L to about 15 g/L to achieve the desired reduction of NGA2F and NGA2F-GlcNac oligosaccharides and a corresponding increase in the NA1F and NA2F oligosaccharides.

In certain embodiments, a combination of plant hydrolysates may be used, for example, at least two of soy, pea and wheat hydrolysates. In a particular embodiment, a combination of each of soy, pea and wheat hydrolysates may be used.

In certain embodiments, the concentration of yeast and/or plant hydrolysates is maintained in such a manner as to reduce the NGA2F and NGA2F-GlcNac sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100% and ranges within one or more of the preceding. In certain embodiments, the concentration of yeast and/or plant hydrolysates is maintained in such a manner as to increase the NA1F and NA2F sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100% and ranges within one or more of the preceding.

In particular embodiments, the cell culture medium includes yeast hydrolysate prior to supplementing the medium as set forth herein. In another embodiment, the cell culture medium is substantially free of yeast hydrolysate prior to supplementing the medium as set forth herein.

In particular embodiments, the cell culture medium includes plant hydrolysate prior to supplementing the medium as set forth herein. In another embodiment, the cell culture medium is substantially free of plant hydrolysate prior to supplementing the medium as set forth herein.

In other embodiments, the cell culture medium includes both plant and yeast hydrolysate prior to modulating the concentration of each as set forth herein. In another embodiment, the cell culture medium is substantially free of both plant and yeast hydrolysate prior to supplementing the medium as set forth herein.

In certain embodiments, control over the glycosylation distribution of proteins produced by cell culture can be exerted by maintaining the appropriate yeast hydrolysate concentration in the cell culture expressing the protein of interest as described herein. Specific culture conditions can be used in various cultivation methods including, but not limited to, batch, fed-batch, chemostat and perfusion and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads and any other configuration appropriate for optimal growth and productivity of the desired cell line.

Modulating Yeast to Plant Hydrolysate Ratio in Cell Culture Medium

According to the present invention the relative amounts of yeast and plant hydrolysates may be modulated to achieve desirable oligosaccharide distribution. For example, but not by way of limitation, by adjusting the concentration ratio of these two hydrolysates, yeast and soy (phytone), within the range of about 0.1 to about 4.0, about 0.2 to about 2.5 or about 0.25 to about 1.55, the resultant oligosaccharide distribution can be modified. As outlined in Example 1, non-limiting embodiments of the present invention include supplements comprising 100% yeast hydrolysate as well as those that are 100% plant hydrolysate. Thus, this disclosure provides a means to modulate glycosylation variations introduced by process inputs, such as raw materials and other variability inherent in dynamic manufacturing operations. Ultimately, the disclosure enables in-process control of protein glycosylation with respect to desired product specifications.

In certain embodiments, the ratio of these two hydrolysates, yeast and soy (phytone), is maintained in such a manner as to reduce the NGA2F and NGA2F-GlcNac sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100% and ranges within one or more of the preceding. In certain embodiments, the ratio of these two hydrolysates, yeast and soy (phytone), is maintained in such a manner as to increase the NA1F and NA2F sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100% and ranges within one or more of the preceding.

In particular embodiments, the cell culture medium includes yeast hydrolysate and plant hydrolysate prior to adjusting the ratio as set forth herein. In another embodiment, the cell culture medium is substantially free of yeast and/or plant hydrolysate prior to supplementing the medium to achieve the desired ratio as set forth herein.

In certain embodiments, control over the glycosylation distribution of protein produced by cell culture can be exerted by maintaining the appropriate yeast to plant hydrolysate ratio in the cell culture expressing the protein of interest as described herein. Specific culture conditions can be used in various cultivation methods including, but not limited to, batch, fed-batch, chemostat and perfusion and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads and any other configuration appropriate for optimal growth and productivity of the desired cell line Supplementation with Asparagine and/or Glutamine According to the present invention the concentration of asparagine and/or glutamine may be modified to achieve desirable oligosaccharide distribution. For example, but not by way of limitation, by adjusting the concentration of one or both of these two amino acids, the resultant oligosaccharide distribution can be modified. Thus, this disclosure provides a means to modulate glycosylation variations introduced by process inputs, such as raw materials and other variability inherent in dynamic manufacturing operations. Ultimately, the disclosure enables in-process control of protein glycosylation with respect to desired product specifications.

The experiments disclosed herein demonstrate that, in certain embodiments, supplementation of cell culture media with asparagine and/or glutamine can modulate product quality of a mAb by, in certain embodiments, increasing the NGA2F and NGA2F-GlcNac and, in certain embodiments, decreasing the NA1F and NA2F oligosaccharides. For example, but not by way of limitation, the percentage of NGA2F and NGA2F-GlcNac can be increased by 2-4% and the percentage of NA1F and NA2F was decreased by 2-5% when 0.4 to 1.6 g/L asparagine is added on either day 0 or days 6 or 7, as outlined in Example 5, below. Similarly, addition of 0.4 g/L glutamine, to the culture run described in Example 5, below, increased the percentage of NGA2F and NGA2F-GlcNac by 1% and lowered the percentage of NA1F and NA2F by 1%. Finally, adding both asparagine and glutamine (0.4 g/L of each), to the cell culture run described in Example 5, below, increased the percentage of NGA2F and NGA2F-GlcNac by 3% and decreased the percentage of NA1F and NA2F by 4%. In addition, the cell growth profile is the same when 0.8 and 1.6 g/L of asparagine was added, but a dose dependent effect on oligosaccharide distribution was observed, indicating that the effect on oligosaccharide distribution was due to the addition of asparagine and not the increased maximum viable cell density or delayed drop in viability.

In certain embodiments, about 0.1 to about 4 g/L, about 0.2 to about 3 g/L or about 0.4 to about 2 g/L of asparagine and/or glutamine is added to the cell culture medium. In a particular embodiment, about 0.1 to about 4 g/L, about 0.2 to about 3 g/L or about 0.4 to about 2 g/L of asparagine is added to the cell culture medium. In a particular embodiment, about 0.1 to about 4 g/L, about 0.2 to about 3 g/L or about 0.4 to about 2 g/L of glutamine is added to the cell culture medium.

In certain embodiments, the total amount of asparagine and/or glutamine in the cell culture media will range from about 0 mM to about 40 mM or about 0 mM to about 26 mM. In certain embodiments, for example, those embodiments where a hydrolysate media is employed, the range of asparagine in the cell culture media will range from about 1 mM to about 15 mM. In certain embodiments, for example, but not limited to, those embodiments where GIA1 media is employed, the range of asparagine in the cell culture media will range from about 12 mM to about 26 mM.

In certain embodiments, the concentration of asparagine and/or glutamine is maintained in such a manner as to reduce the NA1F and NA2F sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100% and ranges within one or more of the preceding. In certain embodiments, the concentration of asparagine and/or glutamine is maintained in such a manner as to increase the NGA2F and NGA2F-GlcNac sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100% and ranges within one or more of the preceding.

In particular embodiments, the cell culture medium includes asparagine prior to modulating the concentration thereof as set forth herein. In another embodiment, the cell culture medium is substantially free of asparagine prior to modulating the concentration thereof as set forth herein.

In particular embodiments, the cell culture medium includes glutamine prior to modulating the concentration thereof as set forth herein. In another embodiment, the cell culture medium is substantially free of glutamine prior to modulating the concentration thereof as set forth herein.

In other embodiments, the cell culture medium includes both asparagine and glutamine prior to modulating the concentration of each as set forth herein. In another embodiment, the cell culture medium is substantially free of both asparagine and glutamine prior to modulating the concentration thereof as set forth herein.

In certain embodiments, control over the glycosylation distribution of protein produced by cell culture can be exerted by maintaining the appropriate asparagine and/or glutamine concentration in the cell culture expressing the protein of interest as described herein. Specific culture conditions can be used in various cultivation methods including, but not limited to, batch, fed-batch, chemostat and perfusion and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads and any other configuration appropriate for optimal growth and productivity of the desired cell line.

Assay for Analyzing Oligosaccharide Distribution

Oligosaccharide distribution can be assayed by obtaining a profile of the various oligosaccharides present in a sample of the protein of interest. By way of example, the first step in the profiling of glycans can involve releasing the glycan from the protein using enzymatic digestion with a N-glycanase, e.g. PNGase F or PNGase A. (Varki et al. Essentials of Glycobiology, $2^{nd}$ Ed. Publisher Cold Spring Harbor, Chapter 47, 2009). N-Glycanase cleaves the GlcNAc-Asn bond, releasing the N-glycan and converting asparagine into aspartate. Upon release, the free reducing end of each glycan can be labeled by reductive amination with a fluorescent tag such as 2-aminopyridine (2-AP), 2-aminobenzamide (2-AB), 2,6-diaminopyridine (DAP), or biotinylated 2,6-diaminopyridine (BAP). The resulting labeled mixture of glycans can be separated by normal-phase HPLC (NP-HPLC) and detected by a fluorescence detector. The fluorescent tag also allows quantitation of the glycan. The chromatographic profile of the mixture is compared with that of well characterized oligosaccharides standards. Such comparison makes it possible to estimate the number, relative quantities, and types of glycans present in a glycoprotein. Individual fractions may be further analyzed by MS or NMR. Sequential treatments with specific exoglycosidases followed by labeling at the reducing end may also be used to obtain structural information of the glycans. A shift in glycan HPLC elution indicates susceptibility to the specific glycosidase. Alternatively or in combination, the oligosaccharide distribution of a protein sample can be assayed as set forth in the Examples (see, for example, the materials and methods provided in Example 1.1).

Antibody Generation

Antibodies to be recombinantly produced by the methods of the present invention can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

In certain embodiments, the animal system for preparing hybridomas is the murine system. Hybridoma production is a well-established procedure. Immunization protocols and techniques for isolation of immunized splenocytes for fusion are known in the art. Fusion partners (e.g., murine myeloma cells) and fusion procedures are also known.

An antibody can be, in certain embodiments, a human, a chimeric or a humanized antibody. Humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter and U.S. Pat. Nos. 5,530,101; 5,585,089; 5,693,762 and 6,180,370 to Queen et al.).

Human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.) and XenoMouse® (Amgen).

Moreover, alternative transchromosomic animal systems expressing human immunoglobulin genes are available in the art and can be used to raise antibodies of the disclosure. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise the antibodies of this disclosure.

In certain embodiments, the antibodies of this disclosure are recombinant human antibodies, which can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The antibodies or antigen-binding portions thereof can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173: 1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

Antibody Production

To express an antibody of the invention, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector or blunt end ligation if no restriction sites are present). Prior to insertion of the antibody or antibody-related light or heavy chain sequences, the expression vector may already carry antibody constant region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g. origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans* and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa* and *Streptomyces*. One suitable *E. coli* cloning host is *E. coli* 294 (ATCC 31,446), although other strains such as *E. coli* B, *E. coli* X1776 (ATCC 31,537) and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae* or common baker's yeast, is the most commonly used among lower eukaryotic host microorganisms. However, a number of other genera, species and strains are commonly available and useful herein, such as *Schizosaccharomyces*

*pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans* and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium* and *Aspergillus* hosts such as *A. nidulans* and *A. niger.*

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly) and *Bombyx mori* have been identified. A variety of viral strains for transfection are publicly available, e.g., the L-1 variant of *Autographa californica* NPV and the Bm-5 strain of *Bombyx mori* NPV and such viruses may be used as the virus herein according to the present invention, particularly for transfection of *Spodoptera frugiperda* cells. Plant cell cultures of cotton, corn, potato, soybean, *petunia*, tomato and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma) and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767, 704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin or epidermal growth factor), salts (such as sodium chloride, calcium, magnesium and phosphate), buffers (such as HEPES), nucleotides (such as adenosine and thymidine), antibiotics (such as gentamycin drug), trace elements (defined as inorganic compounds usually present at final concentrations in the micromolar range) and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to the antigen to which the putative antibody of interest binds. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the one to which the putative antibody of interest binds, depending on the specificity of the antibody of the invention, by crosslinking an antibody of the invention to a second antibody by standard chemical crosslinking methods.

In a suitable system for recombinant expression of an antibody of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock or enzymatic treatments. Such disruption releases the entire contents of the cell into the homogenate and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

Methods of Treatment Using the Compositions of the Invention

The compositions of the present invention including proteins with controlled oligosaccharide heterogeneity, e.g., desired NGA2F and (NGA2F-GlcNAc) and/or NA1F and NA2F distribution, may be used to treat any disorder in a subject for which the therapeutic protein of interest (e.g., an antibody or an antigen binding portion thereof) comprised in the composition is appropriate for treating.

A "disorder" is any condition that would benefit from treatment with the protein of interest. This includes chronic and acute disorders or diseases including those pathological conditions which predispose the subject to the disorder in question. In the case of an anti-TNFα antibody or antigen binding portion thereof, such as adalimumab, a therapeutically effective amount of the controlled protein heterogeneity composition may be administered to treat a disorder in which TNFα activity is detrimental.

A disorder in which TNFα activity is detrimental includes a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody.

TNFα has been implicated in the pathophysiology of a wide variety of a TNFα-related disorders including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503). Accordingly, the controlled protein heterogeneity composition of the invention may be used to treat an autoimmune disease, such as rheumatoid arthritis, juvenile idiopathic arthritis or psoriatic arthritis, an intestinal disorder, such as Crohn's disease or ulcerative colitis, a spondyloarthropathy, such as ankylosing spondylitis or a skin disorder, such as psoriasis.

Disorders in which TNFα activity is detrimental are well known in the art and described in detail in U.S. Pat. No. 8,231,876 and U.S. Pat. No. 6,090,382, the entire contents of each of which are expressly incorporated herein by reference. In one embodiment, "a disorder in which TNFα activity is detrimental" includes sepsis (including septic shock, endotoxic shock, gram negative sepsis and toxic shock syndrome), autoimmune diseases (including rheumatoid arthritis, rheumatoid spondylitis, osteoarthritis and gouty arthritis, allergy, multiple sclerosis, autoimmune diabetes, autoimmune uveitis, nephrotic syndrome, multisystem autoimmune diseases, lupus (including systemic lupus, lupus nephritis and lupus cerebritis), Crohn's disease and autoimmune hearing loss), infectious diseases (including malaria, meningitis, acquired immune deficiency syndrome (AIDS), influenza and cachexia secondary to infection), allograft rejection and graft versus host disease, malignancy, pulmonary disorders (including adult respiratory distress syndrome (ARDS), shock lung, chronic pulmonary inflammatory disease, pulmonary sarcoidosis, pulmonary fibrosis, silicosis, idiopathic interstitial lung disease and chronic obstructive airway disorders (COPD), such as asthma), intestinal disorders (including inflammatory bowel disorders, idiopathic inflammatory bowel disease, Crohn's disease and Crohn's disease-related disorders (including fistulas in the bladder, vagina and skin; bowel obstructions; abscesses; nutritional deficiencies; complications from corticosteroid use; inflammation of the joints; erythem nodosum; pyoderma gangrenosum; lesions of the eye, Crohn's related arthralgias, fistulizing Crohn's indeterminant colitis and pouchitis), cardiac disorders (including ischemia of the heart, heart insufficiency, restenosis, congestive heart failure, coronary artery disease, angina pectoris, myocardial infarction, cardiovascular tissue damage caused by cardiac arrest, cardiovascular tissue damage caused by cardiac bypass, cardiogenic shock and hypertension, atherosclerosis, cardiomyopathy, coronary artery spasm, coronary artery disease, valvular disease, arrhythmias and cardiomyopathies), spondyloarthropathies (including ankylosing spondylitis, psoriatic arthritis/spondylitis, enteropathic arthritis, reactive arthritis or Reiter's syndrome and undifferentiated spondyloarthropathies), metabolic disorders (including obesity and diabetes, including type 1 diabetes mellitus, type 2 diabetes mellitus, diabetic neuropathy, peripheral neuropathy, diabetic retinopathy, diabetic ulcerations, retinopathy ulcerations and diabetic macrovasculopathy), anemia, pain (including acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain and genitourinary tract-related pain including cystitis), hepatic disorders (including hepatitis, alcoholic hepatitis, viral hepatitis, alcoholic cirrhosis, al antitypsin deficiency, autoimmune cirrhosis, cryptogenic cirrhosis, fulminant hepatitis, hepatitis B and C and steatohepatitis, cystic fibrosis, primary biliary cirrhosis, sclerosing cholangitis and biliary obstruction), skin and nail disorders (including psoriasis (including chronic plaque psoriasis, guttate psoriasis, inverse psoriasis, pustular psoriasis and other psoriasis disorders), *pemphigus vulgaris, scleroderma,* atopic dermatitis (eczema), sarcoidosis, erythema nodosum, hidradenitis suppurativa, lichen planus, Sweet's syndrome, *scleroderma* and vitiligo), vasculitides (including Behcet's disease) and other disorders, such as juvenile rheumatoid arthritis (JRA), endometriosis, prostatitis, choroidal neovascularization, sciatica, Sjogren's syndrome, uveitis, wet macular degeneration, osteoporosis and osteoarthritis.

As used herein, the term "subject" is intended to include living organisms, e.g., prokaryotes and eukaryotes. Examples of subjects include mammals, e.g., humans, dogs, cows, horses, pigs, sheep, goats, cats, mice, rabbits, rats and transgenic non-human animals. In specific embodiments of the invention, the subject is a human.

As used herein, the term "treatment" or "treat" refers to both therapeutic treatment and prophylactic or preventative measures. Those in need of treatment include those already with the disorder, as well as those in which the disorder is to be prevented.

In one embodiment, the invention provides a method of administering compositions of an anti-TNFα antibody or antigen binding portion thereof, with desired oligosaccharide heterogeneity, e.g., desired NGA2F and (NGA2F-GlcNAc) and/or NA1F and NA2F distribution, to a subject such that TNFα activity is inhibited or a disorder in which TNFα activity is detrimental is treated. In one embodiment, the TNFα is human TNFα and the subject is a human subject. In one embodiment, the anti-TNFα antibody is adalimumab, also referred to as HUMIRA®.

The controlled protein heterogeneity compositions of the invention can be administered by a variety of methods known in the art. Exemplary routes/modes of administration include subcutaneous injection, intravenous injection or infusion. In certain aspects, a controlled protein heterogeneity composition may be orally administered. As will be appreciated by the skilled artisan, the route and/or mode of administration will vary depending upon the desired results.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments, it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved and (b) the limitations inherent in the art of compounding such an active compound for the treatment of sensitivity in individuals.

An exemplary, non-limiting range for a therapeutically or prophylactically effective amount of a controlled protein heterogeneity composition of the invention is 0.01-20 mg/kg or 1-10 mg/kg or 0.3-1 mg/kg. With respect to controlled protein heterogeneity composition comprising an anti-TNFα antibody or antigen-binding portion thereof, such as adalimumab, an exemplary dose is 40 mg every other week. In some embodiments, in particular for treatment of ulcerative colitis or Crohn's disease, an exemplary dose includes an initial dose (Day 1) of 160 mg (e.g., four 40 mg injections in one day or two 40 mg injections per day for two consecutive days), a second dose two weeks later of 80 mg and a maintenance dose of 40 mg every other week beginning two weeks later. Alternatively, for psoriasis for example, a dosage can include an 80 mg initial dose followed by 40 mg every other week starting one week after the initial dose.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions and that dosage ranges set forth herein are exemplary only and are not intended to limit the scope or practice of the claimed composition.

Pharmaceutical Formulations Containing the Controlled Protein Heterogeneity Compositions of the Invention The present invention further provides preparations and formulations comprising controlled protein heterogeneity compositions, e.g., having desired NGA2F and (NGA2F-GlcNAc) and/or NA1F and NA2F distribution, of the invention. It should be understood that any of the proteins of interest, such as antibodies and antibody fragments described herein, including proteins of interest having any one or more of the structural and functional features described in detail throughout the application, may be formulated or prepared as described below. When various formulations are described in this section as including a protein of interest, such as an antibody, it is understood that such a protein of interest may be a protein having any one or more of the characteristics of the proteins of interest described herein. In one embodiment, the antibody is an anti-TNFα antibody or antigen-binding portion thereof.

In certain embodiments, the controlled protein heterogeneity compositions of the invention may be formulated with a pharmaceutically acceptable carrier as pharmaceutical (therapeutic) compositions and may be administered by a variety of methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the proteins of interest (e.g., antibodies) of the present invention and with each other, in a manner such that there is no interaction which would substantially impair the desired pharmaceutical efficacy.

The controlled protein heterogeneity compositions of the invention are present in a form known in the art and acceptable for therapeutic uses. In one embodiment, a formulation of the controlled protein heterogeneity compositions of the invention is a liquid formulation. In another embodiment, a formulation of the controlled protein heterogeneity compositions of the invention is a lyophilized formulation. In a further embodiment, a formulation of the controlled protein heterogeneity compositions of the invention is a reconstituted liquid formulation. In one embodiment, a formulation of the controlled protein heterogeneity compositions of the invention is a stable liquid formulation. In one embodiment, a liquid formulation of the controlled protein heterogeneity compositions of the invention is an aqueous formulation. In another embodiment, the liquid formulation is non-aqueous. In a specific embodiment, a liquid formulation of the controlled protein heterogeneity compositions of the invention is an aqueous formulation wherein the aqueous carrier is distilled water.

The formulations of the controlled protein heterogeneity compositions of the invention comprise a protein of interest (e.g., an antibody) in a concentration resulting in a w/v appropriate for a desired dose. The protein of interest may be present in the formulation at a concentration of about 1 mg/ml to about 500 mg/ml, e.g., at a concentration of at least 1 mg/ml, at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml or at least 300 mg/ml.

In a specific embodiment, a formulation of the controlled protein heterogeneity compositions of the invention comprises at least about 100 mg/ml, at least about 125 mg/ml, at least 130 mg/ml or at least about 150 mg/ml of protein of interest (e.g., an antibody) of the invention.

In one embodiment, the concentration of protein of interest (e.g., antibody), which is included in the formulation of the invention, is between about 1 mg/ml and about 25 mg/ml, between about 1 mg/ml and about 200 mg/ml, between about 25 mg/ml and about 200 mg/ml, between about 50 mg/ml and about 200 mg/ml, between about 75 mg/ml and about 200 mg/ml, between about 100 mg/ml and about 200 mg/ml, between about 125 mg/ml and about 200 mg/ml, between about 150 mg/ml and about 200 mg/ml, between about 25 mg/ml and about 150 mg/ml, between about 50 mg/ml and about 150 mg/ml, between about 75 mg/ml and about 150 mg/ml, between about 100 mg/ml and about 150 mg/ml, between about 125 mg/ml and about 150 mg/ml, between about 25 mg/ml and about 125 mg/ml, between about 50 mg/ml and about 125 mg/ml, between about 75 mg/ml and about 125 mg/ml, between about 100 mg/ml and about 125 mg/ml, between about 25 mg/ml and about 100 mg/ml, between about 50 mg/ml and about 100 mg/ml, between about 75 mg/ml and about 100 mg/ml, between about 25 mg/ml and about 75 mg/ml, between about 50 mg/ml and about 75 mg/ml or between about 25 mg/ml and about 50 mg/ml.

In a specific embodiment, a formulation of the controlled protein heterogeneity compositions of the invention comprises between about 90 mg/ml and about 110 mg/ml or between about 100 mg/ml and about 210 mg/ml of a protein of interest (e.g., an antibody).

The formulations of the controlled protein heterogeneity compositions of the invention comprising a protein of interest (e.g., an antibody) may further comprise one or more active compounds as necessary for the particular indication being treated, typically those with complementary activities that do not adversely affect each other. Such additional active compounds are suitably present in combination in amounts that are effective for the purpose intended.

The formulations of the controlled protein heterogeneity compositions of the invention may be prepared for storage by mixing the protein of interest (e.g., antibody) having the desired degree of purity with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives or the like (Goodman and Gilman's The Pharmacological Basis of Therapeutics, 12$^{th}$ edition, L. Brunton, et al. and *Remington's Pharmaceutical Sciences,* 16th edition, Osol, A. Ed. (1999)), in the form of lyophilized formulations or aqueous solutions at a desired final concentration. Acceptable carriers, excipients or stabilizers are nontoxic to recipients at the dosages and concentrations employed and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin or immunoglobulins; hydrophilic polymers such as polyvinylpyrrolidone; amino acids such as glycine, glutamine, asparagine, histidine, arginine or lysine; monosaccharides, disaccharides and other carbohydrates including trehalose, glucose, mannose or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

The buffering agent may be histidine, citrate, phosphate, glycine or acetate. The saccharide excipient may be trehalose, sucrose, mannitol, maltose or raffinose. The surfactant may be polysorbate 20, polysorbate 40, polysorbate 80 or Pluronic F68. The salt may be NaCl, KCl, $MgCl_2$ or $CaCl_2$ The formulations of the controlled protein heterogeneity compositions of the invention may include a buffering or pH adjusting agent to provide improved pH control. A formulation of the invention may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0 or between about 5.5 and about 6.5. In a further embodiment, a formulation of the invention has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5 or about 9.0. In a specific embodiment, a formulation of the invention has a pH of about 6.0. One of skill in the art understands that the pH of a formulation generally should not be equal to the isoelectric point of the particular protein of interest (e.g., antibody) to be used in the formulation.

Typically, the buffering agent is a salt prepared from an organic or inorganic acid or base. Representative buffering agents include, but are not limited to organic acid salts such as salts of citric acid, ascorbic acid, gluconic acid, carbonic acid, tartaric acid, succinic acid, acetic acid or phthalic acid; Tris, tromethamine hydrochloride or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is chosen from histidine, citrate, phosphate, glycine and acetate. In a specific embodiment, the buffering agent is histidine. In another specific embodiment, the buffering agent is citrate. In yet another specific embodiment, the buffering agent is glycine. The purity of the buffering agent should be at least 98% or at least 99% or at least 99.5%. As used herein, the term "purity" in the context of histidine and glycine refers to chemical purity of histidine or glycine as understood in the art, e.g., as described in The Merck Index, 13$^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, 2$^{nd}$ Edition, Chapter 5, p. 194, De Luca and Boylan, "Formulation of Small Volume Parenterals", Table 5: Commonly used additives in Parenteral Products. In one embodiment, the buffering agent is at a concentration of about 1 mM or of about 5 mM or of about 10 mM or of about 15 mM or of about 20 mM or of about 25 mM or of about 30 mM or of about 35 mM or of about 40 mM or of about 45 mM or of about 50 mM or of about 60 mM or of about 70 mM or of about 80 mM or of about 90 mM or of about 100 mM. In one embodiment, the buffering agent is at a concentration of 1 mM or of 5 mM or of 10 mM or of 15 mM or of 20 mM or of 25 mM or of 30 mM or of 35 mM or of 40 mM or of 45 mM or of 50 mM or of 60 mM or of 70 mM or of 80 mM or of 90 mM or of 100 mM. In a specific embodiment, the buffering agent is at a concentration of between about 5 mM and about 50 mM. In another specific embodiment, the buffering agent is at a concentration of between 5 mM and 20 mM.

In certain embodiments, the formulation of the controlled protein heterogeneity compositions of the invention comprises histidine as a buffering agent. In one embodiment the histidine is present in the formulation of the invention at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM or at least about 200 mM histidine. In another embodiment, a formulation of the invention comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM or between about 20 mM and about 30 mM histidine. In a further embodiment, the formulation comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM or about 200 mM histidine. In a specific embodiment, a formulation may comprise about 10 mM, about 25 mM or no histidine.

The formulations of the controlled protein heterogeneity compositions of the invention may comprise a carbohydrate excipient. Carbohydrate excipients can act, e.g., as viscosity enhancing agents, stabilizers, bulking agents, solubilizing agents and/or the like. Carbohydrate excipients are generally present at between about 1% to about 99% by weight or volume, e.g., between about 0.1% to about 20%, between about 0.1% to about 15%, between about 0.1% to about 5%, between about 1% to about 20%, between about 5% to about 15%, between about 8% to about 10%, between about 10% and about 15%, between about 15% and about 20%, between about 0.1% to 20%, between 5% to 15%, between 8% to 10%, between 10% and 15%, between 15% and 20%, between about 0.1% to about 5%, between about 5% to about 10% or between about 15% to about 20%. In still other specific embodiments, the carbohydrate excipient is present at 1% or at 1.5% or at 2% or at 2.5% or at 3% or at 4% or at 5% or at 10% or at 15% or at 20%.

Carbohydrate excipients suitable for use in the formulations of the invention include, but are not limited to, monosaccharides such as fructose, maltose, galactose, glucose, D-mannose, sorbose and the like; disaccharides, such as lactose, sucrose, trehalose, cellobiose and the like; polysaccharides, such as raffinose, melezitose, maltodextrins, dextrans, starches and the like; and alditols, such as mannitol, xylitol, maltitol, lactitol, xylitol sorbitol (glucitol) and the like. In one embodiment, the carbohydrate excipients for use in the present invention are chosen from, sucrose, trehalose, lactose, mannitol and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98% or at least 99% or at least 99.5%.

In a specific embodiment, the formulations of the controlled protein heterogeneity compositions of the invention may comprise trehalose. In one embodiment, a formulation of the invention comprises at least about 1%, at least about 2%, at least about 4%, at least about 8%, at least about 20%, at least about 30% or at least about 40% trehalose. In another embodiment, a formulation of the invention comprises between about 1% and about 40%, between about 1% and about 30%, between about 1% and about 20%, between about 2% and about 40%, between about 2% and about 30%, between about 2% and about 20%, between about 4% and about 40%, between about 4% and about 30% or between about 4% and about 20% trehalose. In a further embodiment, a formulation of the invention comprises about 1%, about 2%, about 4%, about 6%, about 8%, about 15%, about 20%, about 30% or about 40% trehalose. In a specific embodiment, a formulation of the invention comprises about 4%, about 6% or about 15% trehalose.

In certain embodiments, a formulation of the controlled protein heterogeneity compositions of the invention comprises an excipient. In a specific embodiment, a formulation of the invention comprises at least one excipient chosen from: sugar, salt, surfactant, amino acid, polyol, chelating agent, emulsifier and preservative. In one embodiment, a formulation of the invention comprises a salt, e.g., a salt selected from: NaCl, KCl, $CaCl_2$ and $MgCl_2$. In a specific embodiment, the formulation comprises NaCl.

A formulation of the controlled protein heterogeneity compositions of the invention may comprise at least about 10 mM, at least about 25 mM, at least about 50 mM, at least about 75 mM, at least about 80 mM, at least about 100 mM, at least about 125 mM, at least about 150 mM, at least about 175 mM, at least about 200 mM or at least about 300 mM sodium chloride (NaCl). In a further embodiment, the formulation may comprise between about 10 mM and about 300 mM, between about 10 mM and about 200 mM, between about 10 mM and about 175 mM, between about 10 mM and about 150 mM, between about 25 mM and about 300 mM, between about 25 mM and about 200 mM, between about 25 mM and about 175 mM, between about 25 mM and about 150 mM, between about 50 mM and about 300 mM, between about 50 mM and about 200 mM, between about 50 mM and about 175 mM, between about 50 mM and about 150 mM, between about 75 mM and about 300 mM, between about 75 mM and about 200 mM, between about 75 mM and about 175 mM, between about 75 mM and about 150 mM, between about 100 mM and about 300 mM, between about 100 mM and about 200 mM, between about 100 mM and about 175 mM or between about 100 mM and about 150 mM sodium chloride. In a further embodiment, the formulation may comprise about 10 mM, about 25 mM, about 50 mM, about 75 mM, about 80 mM, about 100 mM, about 125 mM, about 150 mM, about 175 mM, about 200 mM or about 300 mM sodium chloride.

A formulation of the controlled protein heterogeneity compositions of the invention may also comprise an amino acid, e.g., lysine, arginine, glycine, histidine or an amino acid salt. The formulation may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM or at least about 400 mM of an amino acid. In another embodiment, the formulation may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM or between about 150 mM and about 400 mM of an amino acid. In a further embodiment, a formulation of the invention comprises about 1 mM, 1.6 mM, 25 mM, about 50 mM, about 100 mM, about 150 mM, about 200 mM, about 250 mM, about 300 mM, about 350 mM or about 400 mM of an amino acid.

The formulations of the controlled protein heterogeneity compositions of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic and nonionic surfactants. Surfactants are often used as wetting, emulsifying, solubilizing and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl- or stearyl-sulfobetaine; lauryl-, myristyl-, linoleyl- or stearyl-sarcosine; linoleyl-, myristyl- or cetyl-betaine; lauroamidopropyl-, cocamidopropyl-, linoleamidopropyl-, myristamidopropyl-, palmidopropyl- or isostearamidopropyl-betaine (e.g., lauroamidopropyl); myristamidopropyl-, palmidopropyl- or isostearamidopropyl-dimethylamine; sodium methyl cocoyl- or disodium methyl oleyl-taurate; and the MONAQUA™ series (Mona Industries, Inc., Paterson, N.J.), polyethyl glycol, polypropyl glycol and copolymers of ethylene and propylene glycol (e.g., PLURONICS™, PF68, etc.), can optionally be added to the formulations of the invention to reduce aggregation. In one embodiment, a formulation of the invention comprises Polysorbate 20, Polysorbate 40, Polysorbate 60 or Polysorbate 80. Surfactants are particularly useful if a pump or plastic container is used to administer the formulation. The presence of a pharmaceutically acceptable surfactant mitigates the propensity for the protein to aggregate. The formulations may comprise a polysorbate which is at a concentration ranging from between about 0.001% to about 1% or about 0.001% to about 0.1% or about 0.01% to about 0.1%. In other specific embodiments, the formulations of the invention comprise a polysorbate which is at a concentration of 0.001% or 0.002% or 0.003% or 0.004% or 0.005% or 0.006% or 0.007% or 0.008% or 0.009% or 0.01% or 0.015% or 0.02%.

The formulations of the controlled protein heterogeneity compositions of the invention may optionally further comprise other common excipients and/or additives including, but not limited to, diluents, binders, stabilizers, lipophilic solvents, preservatives, adjuvants or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal or mixtures thereof can optionally be added to the formulations of the invention at any suitable concentration such as between about 0.001% to about 5% or any range or value therein. The concentration of preservative used in the formulations of the invention is a concentration sufficient to yield a microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", $21^{st}$ ed., Lippincott Williams & Wilkins, (2005) and in the "Physician's Desk Reference", $60^{th}$ ed., Medical Economics, Montvale, N.J. (2005). Pharmaceutically acceptable carriers can be routinely selected that are suitable for the mode of administration, solubility and/or stability of protein of interest (e.g., an antibody), as well known those in the art or as described herein.

In one embodiment, the controlled protein heterogeneity compositions of the invention are formulated with the same or similar excipients and buffers as are present in the commercial adalimumab (HUMIRA®) formulation, as described in the "Highlights of Prescribing Information" for HUMIRA® (adalimumab) Injection (Revised January 2008) the contents of which are hereby incorporated herein by reference. For example, each prefilled syringe of HUMIRA®, which is administered subcutaneously, delivers 0.8 mL (40 mg) of drug product to the subject. Each 0.8 mL of HUMIRA® contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 and water for Injection, USP. Sodium hydroxide is added as necessary to adjust pH.

It will be understood by one skilled in the art that the formulations of the controlled protein heterogeneity compositions of the invention may be isotonic with human blood, wherein the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonicity of the formulation. Tonicity modifiers suitable for this invention include, but are not limited to, saccharides, salts and amino acids.

In certain embodiments, the formulations of the controlled protein heterogeneity compositions of the invention have an osmotic pressure from about 100 mOSm to about 1200 mOSm or from about 200 mOSm to about 1000 mOSm or from about 200 mOSm to about 800 mOSm or from about 200 mOSm to about 600 mOSm or from about 250 mOSm to about 500 mOSm or from about 250 mOSm to about 400 mOSm or from about 250 mOSm to about 350 mOSm.

The concentration of any one component or any combination of various components, of the formulations of the controlled protein heterogeneity compositions of the invention is adjusted to achieve the desired tonicity of the final formulation. For example, the ratio of the carbohydrate excipient to protein of interest (e.g., antibody) may be adjusted according to methods known in the art (e.g., U.S. Pat. No. 6,685,940). In certain embodiments, the molar ratio of the carbohydrate excipient to protein of interest (e.g., antibody) may be from about 100 moles to about 1000 moles of carbohydrate excipient to about 1 mole of protein of interest or from about 200 moles to about 6000 moles of carbohydrate excipient to about 1 mole of protein of interest or from about 100 moles to about 510 moles of carbohydrate excipient to about 1 mole of protein of interest or from about 100 moles to about 600 moles of carbohydrate excipient to about 1 mole of protein of interest.

The desired isotonicity of the final formulation may also be achieved by adjusting the salt concentration of the formulations. Pharmaceutically acceptable salts and those suitable for this invention as tonicity modifiers include, but are not limited to, sodium chloride, sodium succinate, sodium sulfate, potassium chloride, magnesium chloride, magnesium sulfate and calcium chloride. In specific embodiments, formulations of the invention comprise NaCl, $MgCl_2$ and/or $CaCl_2$. In one embodiment, concentration of NaCl is between about 75 mM and about 150 mM. In another embodiment, concentration of $MgCl_2$ is between about 1 mM and about 100 mM. Pharmaceutically acceptable amino acids including those suitable for this invention as tonicity modifiers include, but are not limited to, proline, alanine, L-arginine, asparagine, L-aspartic acid, glycine, serine, lysine and histidine.

In one embodiment the formulations of the controlled protein heterogeneity compositions of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with proteins of interest (e.g., antibodies), even trace amounts of harmful and dangerous endotoxin must be removed. In certain specific embodiments, the endotoxin and pyrogen levels in the composition are less then 10 EU/mg or less then 5 EU/mg or less then 1 EU/mg or less then 0.1 EU/mg or less then 0.01 EU/mg or less then 0.001 EU/mg.

When used for in vivo administration, the formulations of the controlled protein heterogeneity compositions of the invention should be sterile. The formulations of the invention may be sterilized by various sterilization methods, including sterile filtration, radiation, etc. In one embodiment, the protein of interest (e.g., antibody) formulation is filter-sterilized with a presterilized 0.22-micron filter. Sterile compositions for injection can be formulated according to conventional pharmaceutical practice as described in "Remington: The Science & Practice of Pharmacy", $21^{st}$ ed., Lippincott Williams & Wilkins, (2005). Formulations comprising proteins of interest (e.g., antibodies), such as those disclosed herein ordinarily will be stored in lyophilized form or in solution. It is contemplated that sterile compositions comprising proteins of interest (e.g., antibodies) are placed into a container having a sterile access port, for example, an intravenous solution bag or vial having an adapter that allows retrieval of the formulation, such as a stopper pierceable by a hypodermic injection needle. In one embodiment, a composition of the invention is provided as a pre-filled syringe.

In one embodiment, a formulation of the controlled protein heterogeneity compositions of the invention is a lyophilized formulation. The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen and synthetic monomers and polymers.

A "lyoprotectant" is a molecule which, when combined with a protein of interest (such as an antibody of the invention), significantly prevents or reduces chemical and/or physical instability of the protein upon lyophilization and subsequent storage. Lyoprotectants include, but are not limited to, sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol and mannitol; propylene glycol; polyethylene glycol; PLURONICS™; and combinations thereof. Additional examples of lyoprotectants include, but are not limited to, glycerin and gelatin and the sugars mellibiose, melezitose, raffinose, mannotriose and stachyose. Examples of reducing sugars include, but are not limited to, glucose, maltose, lactose, maltulose, iso-maltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

In one embodiment, the molar ratio of a lyoprotectant (e.g., trehalose) and protein of interest (e.g., antibody) molecules of a formulation of the invention is at least about 10, at least about 50, at least about 100, at least about 200 or at least about 300. In another embodiment, the molar ratio of a lyoprotectant (e.g., trehalose) and protein of interest molecules of a formulation of the invention is about 1, is about 2, is about 5, is about 10, about 50, about 100, about 200 or about 300.

A "reconstituted" formulation is one which has been prepared by dissolving a lyophilized protein of interest (e.g., antibody) formulation in a diluent such that the protein of interest is dispersed in the reconstituted formulation. The reconstituted formulation is suitable for administration (e.g., parenteral administration) to a patient to be treated with the protein of interest and, in certain embodiments of the invention, may be one which is suitable for intravenous administration.

The "diluent" of interest herein is one which is pharmaceutically acceptable (safe and non-toxic for administration to a human) and is useful for the preparation of a liquid formulation, such as a formulation reconstituted after lyophilization. In some embodiments, diluents include, but are not limited to, sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

In certain embodiments, a formulation of the controlled protein heterogeneity compositions of the invention is a lyophilized formulation comprising a protein of interest (e.g., antibody) of the invention, wherein at least about 90%, at least about 95%, at least about 97%, at least about 98% or at least about 99% of said protein of interest may be recovered from a vial upon shaking said vial for 4 hours at a speed of 400 shakes per minute wherein the vial is filled to half of its volume with the formulation. In another embodiment, a formulation of the invention is a lyophilized formulation comprising a protein of interest of the invention, wherein at least about 90%, at least about 95%, at least about 97%, at least about 98% or at least about 99% of the protein of interest may be recovered from a vial upon subjecting the formulation to three freeze/thaw cycles wherein the vial is filled to half of its volume with said formulation. In a further embodiment, a formulation of the invention is a lyophilized formulation comprising a protein of interest of the invention, wherein at least about 90%, at least about 95%, at least about 97%, at least about 98% or at least about 99% of the protein of interest may be recovered by reconstituting a lyophilized cake generated from said formulation.

In one embodiment, a reconstituted liquid formulation may comprise a protein of interest (e.g., antibody) at the same concentration as the pre-lyophilized liquid formulation.

In another embodiment, a reconstituted liquid formulation may comprise a protein of interest (e.g., antibody) at a higher concentration than the pre-lyophilized liquid formulation, e.g., about 2 fold, about 3 fold, about 4 fold, about 5 fold, about 6 fold, about 7 fold, about 8 fold, about 9 fold or about 10 fold higher concentration of a protein of interest than the pre-lyophilized liquid formulation.

In yet another embodiment, a reconstituted liquid formulation may comprise a protein of interest (e.g., antibody) of the invention at a lower concentration than the pre-lyophilized liquid formulation, e.g., about 2 fold, about 3 fold, about 4 fold, about 5 fold, about 6 fold, about 7 fold, about 8 fold, about 9 fold or about 10 fold lower concentration of a protein of interest than the pre-lyophilized liquid formulation.

The pharmaceutical formulations of the controlled protein heterogeneity compositions of the invention are typically stable formulations, e.g., stable at room temperature.

The terms "stability" and "stable" as used herein in the context of a formulation comprising a protein of interest (e.g., an antibody) of the invention refer to the resistance of the protein of interest in the formulation to aggregation, degradation or fragmentation under given manufacture, preparation, transportation and storage conditions. The "stable" formulations of the invention retain biological activity under given manufacture, preparation, transportation and storage conditions. The stability of the protein of interest can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry and/or ANS binding techniques, compared to a reference formulation. For example, a reference formulation may be a reference standard frozen at −70° C. consisting of 10 mg/ml of a protein of interest of the invention in PBS.

Therapeutic formulations of the controlled protein heterogeneity compositions of the invention may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the protein of interest (e.g., antibody) and the particular therapeutic effect to be achieved and (b) the limitations inherent in the art of compounding such a protein of interest for the treatment of sensitivity in individuals.

Therapeutic compositions of the controlled protein heterogeneity compositions of the invention can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy.

The amount of active ingredient which can be combined with a carrier material to produce a single dosage form will vary depending upon the subject being treated and the particular mode of administration. The amount of active ingredient which can be combined with a carrier material to produce a single dosage form will generally be that amount of the composition which produces a therapeutic effect. By way of example, in certain embodiments, the proteins of interest (including fragments of the protein of interest) are formulated for intravenous administration. In certain other embodiments, the proteins of interest (e.g., antibodies), including fragments of the proteins of interest (e.g., antibody fragments) are formulated for local delivery to the cardiovascular system, for example, via catheter, stent, wire, intramyocardial delivery, intrapericardial delivery or intraendocardial delivery.

Formulations of the controlled protein heterogeneity compositions of the invention which are suitable for topical or transdermal administration include powders, sprays, ointments, pastes, creams, lotions, gels, solutions, patches and inhalants. The active compound may be mixed under sterile conditions with a pharmaceutically acceptable carrier and with any preservatives, buffers or propellants which may be required (U.S. Pat. Nos. 7,378,110; 7,258,873; 7,135,180; 7,923,029; and US Publication No. 20040042972).

The phrases "parenteral administration" and "administered parenterally" as used herein means modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the controlled protein heterogeneity compositions of the invention may be varied so as to obtain an amount of the active ingredient which is effective to achieve the desired therapeutic response for a particular patient, composition and mode of administration, without being toxic to the patient. The selected dosage level will depend upon a variety of pharmacokinetic factors including the activity of the particular compositions of the present invention employed or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated and like factors well known in the medical arts.

In certain embodiments, the proteins of interest (e.g., antibodies) of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; 5,399, 331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant Protein A receptor (Briscoe et al. (1995) *Am. J. Physiol.* 1233:134), different species of which may comprise the formulations of the invention, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in another embodiment, the liposomes include a targeting moiety. In another embodiment, the therapeutic compounds in the liposomes are delivered by bolus injection to a site proximal to the desired area. When administered in this manner, the composition must be fluid to the extent that easy syringability exists. It must be stable under the conditions of manufacture and storage and may be preserved against the contaminating action of microorganisms such as bacteria and fungi. Additionally or alternatively, the proteins of interest (e.g., antibodies) of the invention may be delivered locally to the brain to mitigate the risk that the blood brain barrier slows effective delivery.

In certain embodiments, the controlled protein heterogeneity compositions of the invention may be administered with medical devices known in the art. For example, in certain embodiments a protein of interest (e.g., antibody) or a fragment of protein of interest (e.g., antibody fragment) is administered locally via a catheter, stent, wire or the like. For example, in one embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems and modules are known to those skilled in the art.

The efficient dosages and the dosage regimens for the reduced level of at least one controlled protein heterogeneity composition of the invention depend on the disease or condition to be treated and can be determined by the persons skilled in the art. One of ordinary skill in the art would be able to determine such amounts based on such factors as the subject's size, the severity of the subject's symptoms and the particular composition or route of administration selected.

Alternative Formulations Containing the Controlled Protein Heterogeneity Compositions of the Invention
Alternative Aqueous Formulations The invention also provides a controlled protein heterogeneity composition formulated as an aqueous formulation comprising a protein of interest and water, as described in U.S. Pat. No. 8,420,081, the contents of which are hereby incorporated by reference. In these aqueous formulations, the protein of interest is stable without the need for additional agents. This aqueous formulation has a number of advantages over conventional formulations in the art, including stability of the protein of interest in water without the requirement for additional excipients, increased concentrations of protein of interest without the need for additional excipients to maintain solubility of the protein of interest and low osmolality. These also have advantageous storage properties, as the proteins of interest in the formulation remain stable during storage, e.g., stored as a liquid form for more than 3 months at 7° C. or freeze/thaw conditions, even at high protein of interest concentrations and repeated freeze/thaw processing steps. In one embodiment, formulations described herein include high concentrations of proteins of interest such that the aqueous formulation does not show significant opalescence, aggregation or precipitation.

In one embodiment, an aqueous controlled protein heterogeneity composition comprising a protein of interest, e.g., an antibody, an anti-TNFα antibody or antigen biding portion thereof and water is provided, wherein the formulation has certain characteristics, such as, but not limited to, low conductivity, e.g., a conductivity of less than about 2.5 mS/cm, a protein of interest concentration of at least about 10 μg/mL, an osmolality of no more than about 30 mOsmol/kg and/or the protein of interest has a molecular weight (Mw) greater than about 47 kDa. In one embodiment, the formulation has improved stability, such as, but not limited to, stability in a liquid form for an extended time (e.g., at least about 3 months or at least about 12 months) or stability through at least one freeze/thaw cycle (if not more freeze/thaw cycles). In one embodiment, the formulation is stable for at least about 3 months in a form selected from the group consisting of frozen, lyophilized or spray-dried.

In one embodiment, the formulation has a low conductivity, including, for example, a conductivity of less than about 2.5 mS/cm, a conductivity of less than about 2 mS/cm, a conductivity of less than about 1.5 mS/cm, a conductivity of less than about 1 mS/cm or a conductivity of less than about 0.5 mS/cm.

In another embodiment, controlled protein heterogeneity compositions included in the formulation have a given concentration, including, for example, a concentration of at least about 1 mg/mL, at least about 10 mg/mL, at least about 50 mg/mL, at least about 100 mg/mL, at least about 150 mg/mL, at least about 200 mg/mL or greater than about 200 mg/mL. In another embodiment, the formulation of the invention has an osmolality of no more than about 15 mOsmol/kg.

The aqueous formulations described herein do not rely on standard excipients, e.g., a tonicity modifier, a stabilizing agent, a surfactant, an anti-oxidant, a cryoprotectant, a bulking agent, a lyoprotectant, a basic component and an acidic component. In other embodiments of the invention, the formulation contains water, one or more proteins of interest and no ionic excipients (e.g., salts, free amino acids).

In certain embodiments, the aqueous formulation as described herein comprise a controlled protein heterogeneity composition comprising a protein of interest concentration of at least 50 mg/mL and water, wherein the formulation has an osmolality of no more than 30 mOsmol/kg. Lower limits of osmolality of the aqueous formulation are also encompassed by the invention. In one embodiment the osmolality of the aqueous formulation is no more than 15 mOsmol/kg. The aqueous formulation of the invention may have an osmolality of less than 30 mOsmol/kg and also have a high protein of interest concentration, e.g., the concentration of the protein of interest is at least 100 mg/mL and may be as much as 200 mg/mL or greater. Ranges intermediate to the above recited concentrations and osmolality units are also intended to be part of this invention. In addition, ranges of values using a combination of any of the above recited values as upper and/or lower limits are intended to be included.

The concentration of the aqueous formulation as described herein is not limited by the protein of interest size and the formulation may include any size range of proteins. Included within the scope of the invention is an aqueous formulation comprising at least 40 mg/mL and as much as 200 mg/mL or more of a protein of interest, for example, 40 mg/mL, 65 mg/mL, 130 mg/mL or 195 mg/ml, which may range in size from 5 kDa to 150 kDa or more. In one embodiment, the protein of interest in the formulation of the invention is at least about 15 kD in size, at least about 20 kD in size; at least about 47 kD in size; at least about 60 kD in size; at least about 80 kD in size; at least about 100 kD in size; at least about 120 kD in size; at least about 140 kD in size; at least about 160 kD in size; or greater than about 160 kD in size. Ranges intermediate to the above recited sizes are also intended to be part of this invention. In addition, ranges of values using a combination of any of the above recited values as upper and/or lower limits are intended to be included.

The aqueous formulation as described herein may be characterized by the hydrodynamic diameter ($D_h$) of the proteins of interest in solution. The hydrodynamic diameter of the protein of interest in solution may be measured using dynamic light scattering (DLS), which is an established analytical method for determining the $D_h$ of proteins. Typical values for monoclonal antibodies, e.g., IgG, are about 10 nm. Low-ionic formulations may be characterized in that the $D_h$ of the proteins of interest are notably lower than protein of interest formulations comprising ionic excipients. It has been discovered that the $D_h$ values of antibodies in aqueous formulations made using the diafiltration/ultrafiltration (DF/UF) process, as described in U.S. Pat. No. 8,420,081, using pure water as an exchange medium, are notably lower than the $D_h$ of antibodies in conventional formulations independent of protein concentration. In one embodiment, antibodies in the aqueous formulation as described herein have a $D_h$ of less than 4 nm or less than 3 nm.

In one embodiment, the $D_h$ of the protein of interest in the aqueous formulation is smaller relative to the $D_h$ of the same protein of interest in a buffered solution, irrespective of protein of interest concentration. Thus, in certain embodiments, a protein of interest in an aqueous formulation made in accordance with the methods described herein, will have a $D_h$ which is at least 25% less than the $D_h$ of the protein of interest in a buffered solution at the same given concentration. Examples of buffered solutions include, but are not limited to phosphate buffered saline (PBS). In certain embodiments, proteins of interest in the aqueous formulation of the invention have a $D_h$ that is at least 50% less than the $D_h$ of the protein of interest in PBS in at the given concentration; at least 60% less than the $D_h$ of the protein of interest in PBS at the given concentration; at least 70% less than the $D_h$ of the protein of interest in PBS at the given concentration; or more than 70% less than the $D_h$ of the protein of interest in PBS at the given concentration. Ranges intermediate to the above recited percentages are also intended to be part of this invention, e.g., about 55%, 56%, 57%, 64%, 68% and so forth. In addition, ranges of values using a combination of any of the above recited values as upper and/or lower limits are intended to be included, e.g., about 50% to about 80%.

In one aspect, the aqueous formulation includes the protein of interest at a dosage of about 0.01 mg/kg-10 mg/kg. In another aspect, the dosages of the protein of interest include approximately 1 mg/kg administered every other week or approximately 0.3 mg/kg administered weekly. A skilled practitioner can ascertain the proper dosage and regime for administering to a subject.

Alternative Solid Unit Formulations

The invention also provides a controlled protein heterogeneity composition of the invention formulated as a stable composition of a protein of interest, e.g., an antibody or antigen binding portion thereof and a stabilizer, referred to herein as solid units, as described in Attorney Docket No. 117813-31001, the contents of which are hereby incorporated by reference herein.

Specifically, it has been discovered that despite having a high proportion of sugar, the solid units comprising the controlled protein heterogeneity compositions of the invention maintain structural rigidity and resist changes in shape and/or volume when stored under ambient conditions, e.g., room temperature and humidity, for extended periods of time (e.g., the solid units comprising the controlled protein heterogeneity compositions of the invention do not require storage in a sealed container) and maintain long-term physical and chemical stability of the protein of interest without significant degradation and/or aggregate formation. Moreover, despite having a high proportion of sugar, the solid units comprising the controlled protein heterogeneity compositions of the invention remain free-flowing when stored under ambient conditions, e.g., room temperature and humidity, for extended periods of time and yet are easily dissolved in an aqueous solvent, e.g., water (e.g., the solid units require minimal mixing when contacted with a solvent for reconstitution). Furthermore, the solid units comprising the controlled protein heterogeneity compositions of the invention may be prepared directly in a device for patient use. These properties, when compared to existing techniques which require a vial containing a lyophilized protein of interest provided as a cake (which may not stabilize a protein of interest for extended periods of time), a separate vial for a diluent, one or more sterile syringes and several manipulation steps, thus provides alternative approaches for reconstitution since the solid units comprising the controlled protein heterogeneity compositions of the invention may be provided, e.g., in a dual chambered cartridge, to make reconstitution invisible during patient delivery. Furthermore, the solid units comprising the controlled protein heterogeneity compositions of the invention are versatile in that they can be readily and easily adapted for numerous modes of administration, such as parenteral and oral administration.

As used herein, the term "solid unit," refers to a composition which is suitable for pharmaceutical administration and comprises a protein of interest, e.g., an antibody or peptide and a stabilizer, e.g., a sugar. The solid unit comprising the controlled protein heterogeneity compositions of the invention has a structural rigidity and resistance to changes in shape and/or volume. In one embodiment, the solid unit comprising the controlled protein heterogeneity compositions of the invention is obtained by freeze-drying a pharmaceutical formulation of a therapeutic protein of interest. The solid unit comprising the controlled protein heterogeneity compositions of the invention may be any shape, e.g., geometric shape, including, but not limited to, a sphere, a cube, a pyramid, a hemisphere, a cylinder, a teardrop and so forth, including irregularly shaped units. In one embodiment, the solid unit has a volume ranging from about 1 ml to about 20 ml. In another embodiment, the solid unit is not obtained using spray drying techniques, e.g., the solid unit is not a powder or granule.

As used herein, the phrase "a plurality of solid units" refers to a collection or population of solid units comprising the controlled protein heterogeneity compositions of the invention, wherein the collection comprises two or more solid units having a substantially uniform shape, e.g., sphere and/or volume distribution. A substantially uniform size distribution is intended to mean that the individual shapes and/or volumes of the solid units comprising the controlled protein heterogeneity compositions of the invention are substantially similar and not greater than a 10% standard deviation in volume. For example, a plurality of solid units which are spherical in shape would include a collection of solid units having no greater than 10% standard deviation from an average volume of the spheres. In one embodiment, the plurality of solid units is free-flowing.

Kits and Articles of Manufacture Comprising the Controlled Protein Heterogeneity Compositions of the Invention Also within the scope of the present invention are kits comprising the controlled protein heterogeneity compositions of the invention and instructions for use. The term "kit" as used herein refers to a packaged product comprising components with which to administer the protein of interest (e.g., antibody or antigen-binding portion thereof), of the invention for treatment of a disease or disorder. The kit may comprise a box or container that holds the components of the kit. The box or container is affixed with a label or a Food and Drug Administration approved protocol. The box or container holds components of the invention which may be contained within plastic, polyethylene, polypropylene, ethylene or propylene vessels. The vessels can be capped-tubes or bottles. The kit can also include instructions for administering a protein of interest (e.g., an antibody) of the invention.

The kit can further contain one more additional reagents, such as an immunosuppressive reagent, a cytotoxic agent or a radiotoxic agent or one or more additional proteins of interest of the invention (e.g., an antibody having a complementary activity which binds to an epitope in the TNFα antigen distinct from a first anti-TNFα antibody). Kits typically include a label indicating the intended use of the contents of the kit. The term label includes any writing or recorded material supplied on or with the kit or which otherwise accompanies the kit.

The invention also provides a pharmaceutical pack or kit comprising one or more containers filled with a liquid formulation or lyophilized formulation of a protein of interest (e.g., an antibody or antibody fragment thereof) of the invention. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 mL. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a container filled with a liquid formulation of the invention is a pre-filled syringe. Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. Nos. 6,792,743, 5,607,400, 5,893,842, 7,081,107, 7,041,087, 5,989,227, 6,807,797, 6,142,976, 5,899,889, 7,699,811, 7,540,382, 7,998,120, 7,645,267 and US Patent Publication No. US20050075611. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a protein formulation stored in the syringe. For example, it is understood that silicon based lubricants deposited on the inside surface of the syringe chamber may affect particle formation in the protein formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

In certain embodiments, kits comprising proteins of interest (e.g., antibodies) of the invention are also provided that are useful for various purposes, e.g., research and diagnostic including for purification or immunoprecipitation of protein of interest from cells, detection of the protein of interest in vitro or in vivo. For isolation and purification of a protein of interest, the kit may contain an antibody coupled to beads (e.g., sepharose beads). Kits may be provided which contain the antibodies for detection and quantitation of a protein of interest in vitro, e.g., in an ELISA or a Western blot. As with the article of manufacture, the kit comprises a container and a label or package insert on or associated with the container. The container holds a composition comprising at least one protein of interest (e.g., antibody) of the invention. Additional containers may be included that contain, e.g., diluents and buffers, control proteins of interest (e.g., antibodies). The label or package insert may provide a description of the composition as well as instructions for the intended in vitro or diagnostic use.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising a protein of interest (e.g., an antibody) that is suitable for parenteral administration. In another embodiment, the unit dosage form is provided as a sterile lyophilized powder comprising a protein of interest (e.g., an antibody) that is suitable for reconstitution.

In one embodiment, the unit dosage form is suitable for intravenous, intramuscular, intranasal oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures and other monitoring information.

Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a pharmaceutical agent contained within said packaging material, wherein said pharmaceutical agent comprises a liquid formulation containing a protein of interest (e.g., an antibody). The packaging material includes instruction means which indicate how that said protein of interest (e.g., antibody) can be used to prevent, treat and/or manage one or more symptoms associated with a disease or disorder.

The present invention is further illustrated by the following examples which should not be construed as limiting in any way. The contents of all cited references, including literature references, issued patents and published patent applications, as cited throughout this application are hereby expressly incorporated herein by reference. It should further be understood that the contents of all the figures and tables attached hereto are expressly incorporated herein by reference. The entire contents of the following applications are also expressly incorporated herein by reference:

U.S. Provisional Patent Application 61/893,123, entitled "STABLE SOLID PROTEIN COMPOSITIONS AND METHODS OF MAKING SAME", filed on Oct. 18, 2013;

U.S. Provisional Application Ser. No. 61/892,833, entitled "LOW ACIDIC SPECIES COMPOSITIONS AND METHODS FOR PRODUCING THE SAME USING DISPLACEMENT CHROMATOGRAPHY", filed on Oct. 18, 2013;

U.S. Provisional Patent Application 61/892,710, entitled "MUTATED ANTI-TNFα ANTIBODIES AND METHODS OF THEIR USE", filed on Oct. 18, 2013;

U.S. Provisional Patent Application 61/893,068, entitled "LOW ACIDIC SPECIES COMPOSITIONS AND METHODS FOR PRODUCING THE SAME", filed on Oct. 18, 2013;

U.S. Provisional Patent Application 61/893,088, entitled "MODULATED LYSINE VARIANT SPECIES AND METHODS FOR PRODUCING AND USING THE SAME", filed on Oct. 18, 2013; and U.S. Provisional Patent Application 61/893,131, entitled "PURIFICATION OF PROTEINS USING HYDROPHOBIC INTERACTION CHROMATOGRAPHY", filed on Oct. 18, 2013.

EXAMPLES

Example 1

Control of Heterogeneity by Addition of Hydrolysates to CD Media GIA-1 for Culture of an Adalimumab-Producing Cho Cell Line #1

Control of heterogeneity of therapeutic monoclonal antibodies (mAbs) can aid in ensuring their efficacy, stability, immunogenicity and biological activity. Media composition has been shown to play a role in product quality of mAbs together with process conditions and choice of cell line. In certain embodiments, the present invention provides methods for fine-tuning the product quality profile of a mAb produced in various Chinese hamster ovary (CHO) cell lines by supplementation of yeast and/or plant hydrolysates to chemically defined (CD) media. In certain embodiments, the resulting mAb product is characterized by having a decreased content of complex agalactosylated glycans NGA2F and NGA2F-

GlcNac and increased levels of terminally galactosylated glycans NA1F and NA2F. In certain embodiments, addition of increasing amounts of yeast, soy or wheat hydrolysates from several suppliers to a CD medium resulted in altered product quality profiles in a concentration-dependent manner.

In the studies summarized in this example, the effects on glycosylation resulting from the addition of yeast (Bacto TC Yeastolate: 2, 5, 11 g/L), soy (BBL Phytone Peptone: 2, 4, 7, 10, 15 g/L) or wheat (Wheat Peptone E1: 2, 4, 7, 10, 15 g/L) hydrolysates to CD medium GIA-1 (Life Technologies Gibco; proprietary formulation) in the adalimumab-producing CHO cell line #1 were investigated. The antibody produced by the adalimumab-producing CHO cell line #1 was identified as mAb #1.

1.1 Materials and Methods

Adaptation and production media were supplemented with Bacto TC Yeastolate, BBL Phytone Peptone or Wheat Peptone E1 according to the experimental design in FIG. 39. The control cultures were not supplemented with hydrolysates. In addition to hydrolysates, adaptation media was supplemented with 0.876 g/kg L-glutamine and 2.0 mL/kg methotrexate solution and production media was supplemented with 0.584 g/L L-glutamine. The experiment was designed into two blocks. All media pH was adjusted to approximately 7.1 using 6N hydrochloric acid/5N sodium hydroxide. The media osmolality was adjusted to 290-300 mOsmol/kg with sodium chloride.

The adalimumab-producing cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. At each passage, cultures were inoculated at an initial viable cell density (VCD) of approximately $0.5 \times 10^6$ cells/mL.

Production cultures were initiated in duplicate 500 mL Corning, vented, non-baffled shake flasks each containing 200 mL culture in dry incubators at 35° C., 5% $CO_2$ and 110 RPM. Initial VCD was approximately $0.5 \times 10^6$ cells/mL. A 1.25% (v/v) 40% glucose stock solution was fed when the media glucose concentration was less than 3 g/L.

For all studies described throughout this application, samples were collected daily and measured for cell density and viability using a Cedex cell counter. Retention samples for titer analysis (2×1.5 mL per condition) via Poros A method were collected daily after culture viability fell below 90%. Samples were centrifuged at 12,000 RPM for 5 min and the supernatant was stored at −80° C. until further analysis. The harvest procedure was performed by centrifugation of the culture sample at 3,000 RPM for 30 min followed by storage of the supernatant in 125 mL PETG bottles at −80° C. until protein A purification, oligosaccharide and WCX-10 analysis.

For the oligosaccharide assay, the oligosaccharides are released from the protein by enzymatic digestion with N-glycanase. Once the glycans are released, the free reducing end of each glycan is labeled by reductive amination with a fluorescent tag, 2-aminobenzamide (2-AB). The resulting labeled glycans are separated by normal-phase HPLC (NP-HPLC) in acetonitrile: 50 mM ammonium formate, pH 4.4 and detected by a fluorescence detector. Quantitation is based on the relative area percent of detected sugars. The relative area percents of the agalactosyl fucosylated biantennary oligosaccharides (NGA2F and [NGA2F-GlcNac]) and the galactose-containing fucosylated biantennary oligosaccharides NA1F and NA2F are reported and discussed.

1.2 Culture Growth and Productivity

Figure 1B:
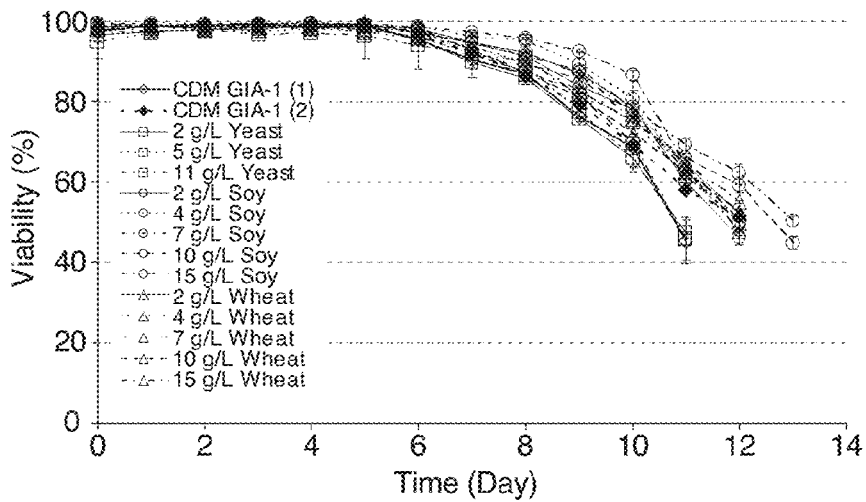
Figure 1C:
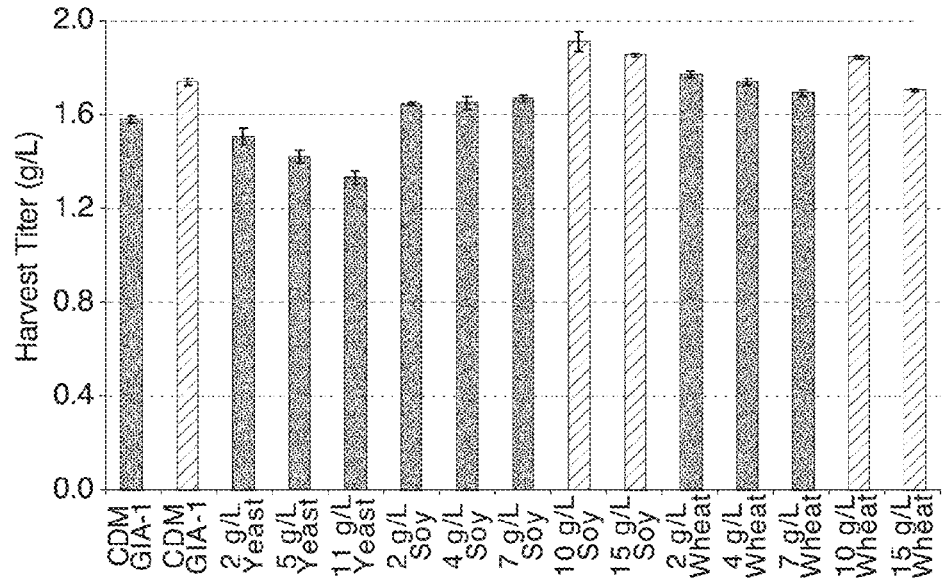

The majority of cultures grew to a similar peak VCD in the range of $9-11 \times 10^6$ cells/mL. Cultures supplemented with 11 g/L yeast hydrolysate BD TC yeastolate experienced slight inhibition of growth (FIG. 1A). Viability profiles were comparable to the control condition with cultures lasting 11 to 13 days (FIG. 1B). Increasing the yeast hydrolysate concentration in CDM media GIA-1 resulted in decreased average productivity compared to the control condition. Cultures supplemented with soy or wheat hydrolysates lasted 12 to 13 days and experienced slightly increased average titer compared to the control condition (FIG. 1C).

1.3 Oligosaccharide Analysis

Figure 2A:
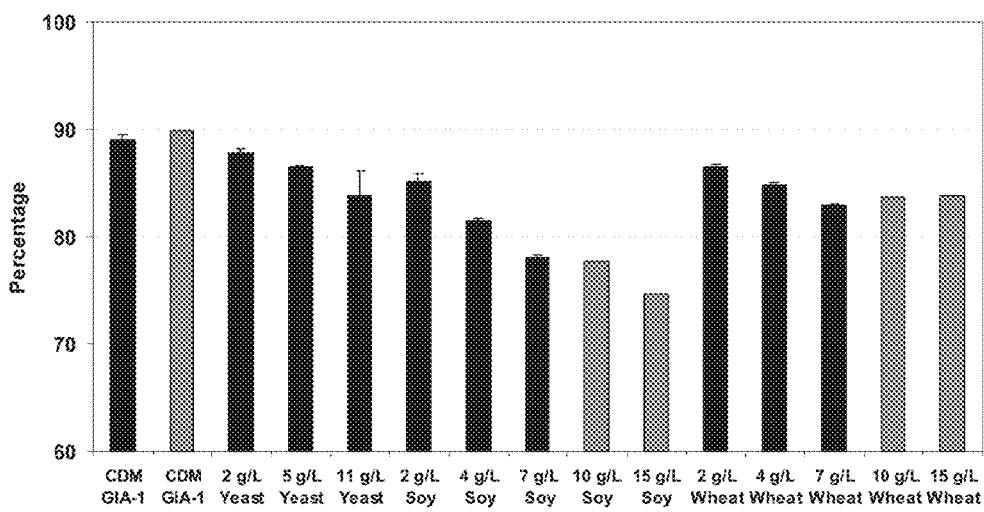
FIGS. 2A and 2B depict the effect of yeast, soy or wheat hydrolysate addition to CDM GIA-1 in adalimumab-producing CHO cell line #1 on (FIG. 2A) NGA2F and (NGA2F-GlcNac) and (FIG. 2B) NA1F and NA2F, respectively.
Figure 2B:
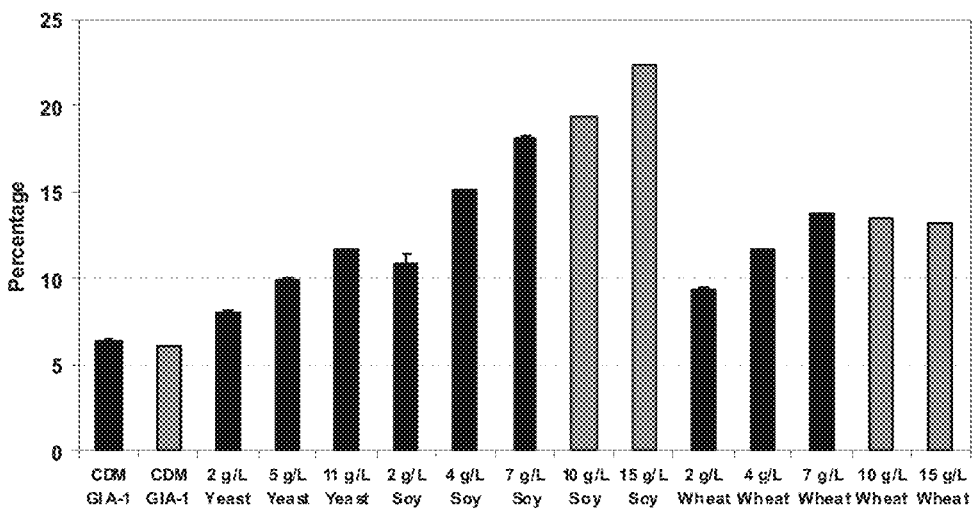

Addition of yeast, soy or wheat hydrolysates to CD media GIA-1 lowered the percentage of glycans NGA2F and NGA2F-GlcNac by 1-14% and increased the percentage of NA1F and NA2F glycans by 2-12% compared to control condition (NGA2F and NGA2F-GlcNac: 89%; NA1F and NA2F: 6%) (FIGS. 2A-B). A dose-dependent decrease in NGA2F and NGA2F-GlcNac and a corresponding increase in NA1F and NA2F glycans was observed with the addition of yeast, soy or wheat hydrolysate over the tested range. The highest percentage decrease in NGA2F and NGA2F-GlcNac and corresponding highest increase in NA1F and NA2F glycans was recorded for the condition supplemented with 7 g/L BD BBL phytone peptone (NGA2F and NGA2F-GlcNac: 78% and NA1F and NA2F: 18%) compared to control.

Example 2

Yeast and Soy Hydrolysates Combined Addition to Multiple Commercially Available CD Media for Culture of an Adalimumab-Producing Cho Cell Line #1

In the study summarized in this example, the effects of combined yeast and soy hydrolysates addition to CD media from multiple suppliers: Life Technologies Gibco (OptiCHO and GIA-1), Irvine Scientific (IS CHO-CD) and HyClone/Thermo Scientific (CDM4CHO) on product quality in the adalimumab-producing CHO cell line #1 utilized in Example 1 were evaluated.

2.1 Materials and Methods

The liquid or powder formulation media were purchased from multiple vendors (Life Technologies Gibco—OptiCHO and GIA-1; Irvine Scientific—IS CHO-CD; and HyClone/Thermo Scientific—CDM4CHO), reconstituted per the manufacturers' recommendations and supplemented with Bacto TC Yeastolate and BBL Phytone Peptone according to the experimental design in FIG. 40. The control cultures for each condition were not supplemented with hydrolysates. All media pH was adjusted to approximately 7.1 using 6N hydrochloric acid/5N sodium hydroxide.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning vented non-baffled shake flasks at an initial VCD of approximately $0.5 \times 10^6$ cells/mL. The shake flask study was run in an extended batch-mode by feeding a glucose solution (1.25% (v/v) of 40% solution) when the media glucose concentration fell below 3 g/L.

2.2 Culture Growth and Productivity

Figure 3A:
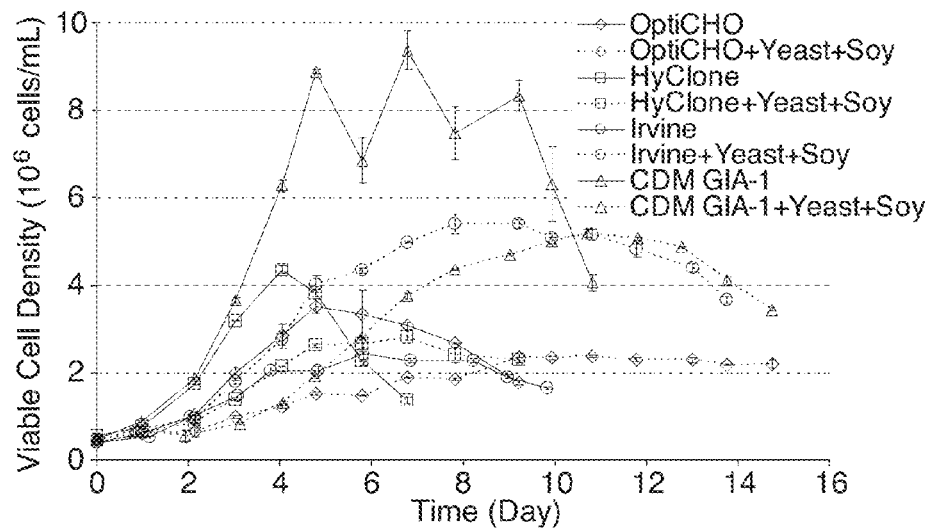
FIGS. 3A-3C depict the effect of combined supplementation of yeast and soy hydrolysates to CD media from multiple suppliers in adalimumab-producing CHO cell line #1 on (FIG. 3A) Culture growth, (FIG. 3B) Culture viability and (FIG. 3C) Harvest titer, respectively.
Figure 3B:
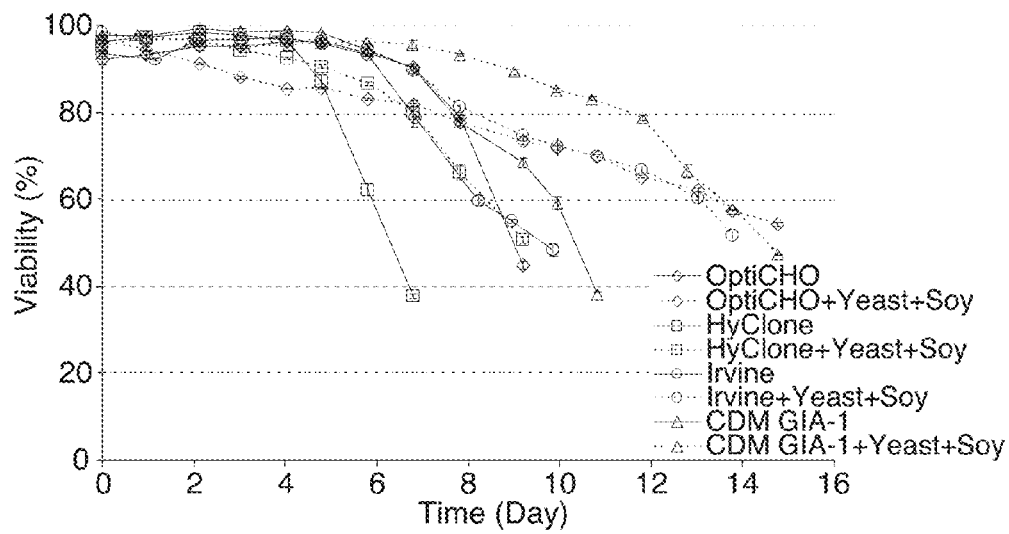
Figure 3C:
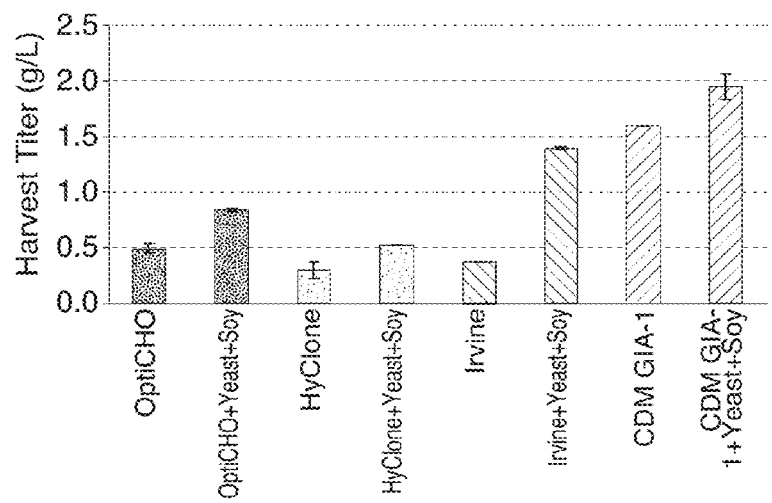

Commercially available CD media supported markedly different culture growth profiles with maximum VCD of 2-9×$10^6$ cells/mL and culture duration ranging from 7 to 15 days (FIG. 3A). Addition of yeast and soy hydrolysates to Life Technologies Gibco OptiCHO and GIA-1 and HyClone CDM4CHO media decreased peak VCD and increased culture length by 2 to 6 days. However, addition of hydrolysates to Irvine IS CHO-CD media increased peak VCD from 2.5×$10^6$ cells/mL to 5.4×$10^6$ cells/mL. Culture viability declined slower with addition of hydrolysates for all media tested (FIG. 3B). Productivity also varied significantly among cultures; however, the addition of hydrolysates to CD media increased productivity in all cases (FIG. 3C).

2.3 Oligosaccharide Analysis

Figure 4A:
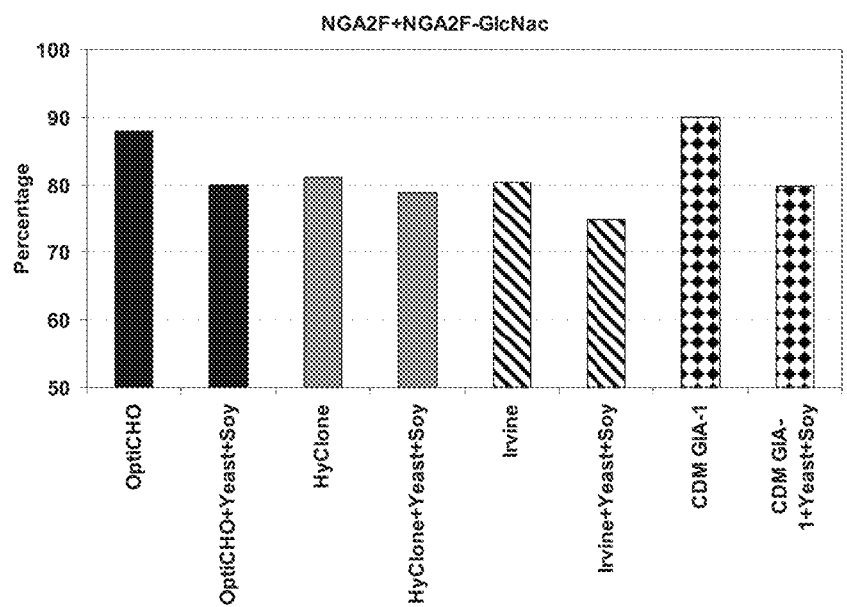
FIGS. 4A and 4B depict the effect of combined supplementation of yeast and soy hydrolysates to CD media from multiple suppliers in adalimumab-producing CHO cell line #1 on (FIG. 4A) NGA2F and (NGA2F-GlcNac) and (FIG. 4B) NA1F and NA2F, respectively.
Figure 4B:
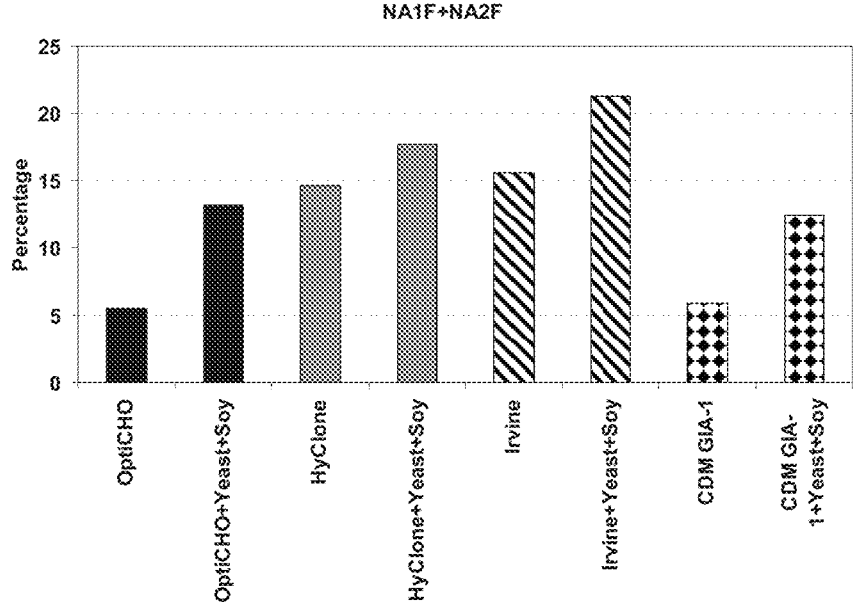
Figure 5A:
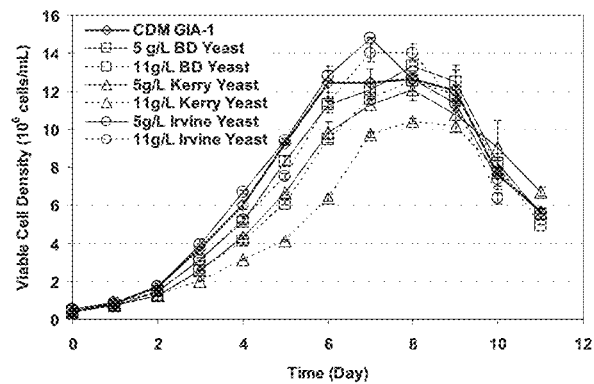
FIGS. 5A-5C depict the effect of supplementing (FIG. 5A) yeast, (FIG. 5B) soy or (FIG. 5C) wheat hydrolysate from multiple vendors to CDM GIA-1 on culture growth in CHO cell line #1, respectively.
Figure 5B:
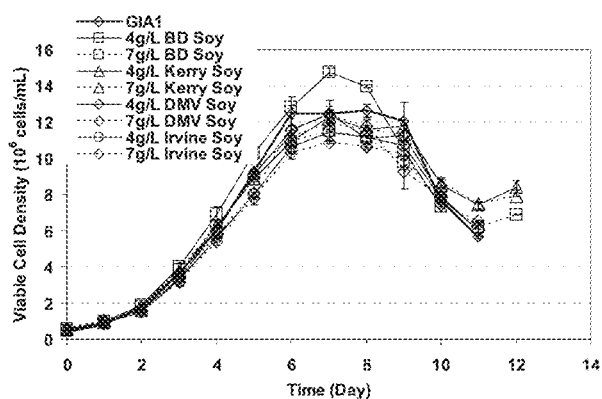
Figure 5C:
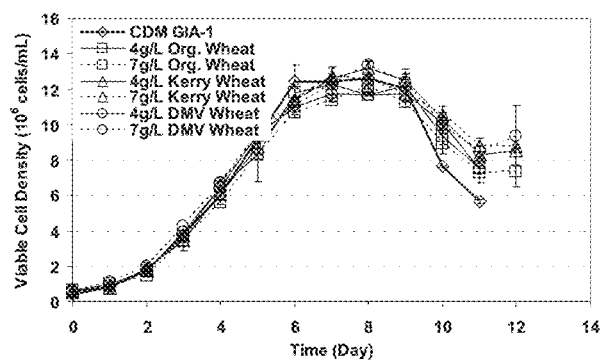
Figure 6A:
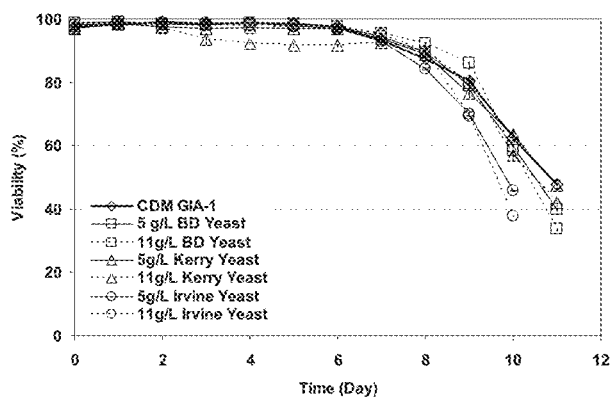
FIGS. 6A-6C depict the effect of supplementing (FIG. 6A) yeast, (FIG. 6B) soy or (FIG. 6C) wheat hydrolysate from multiple vendors to CDM GIA-1 on culture viability in CHO cell line #1, respectively.
Figure 6B:
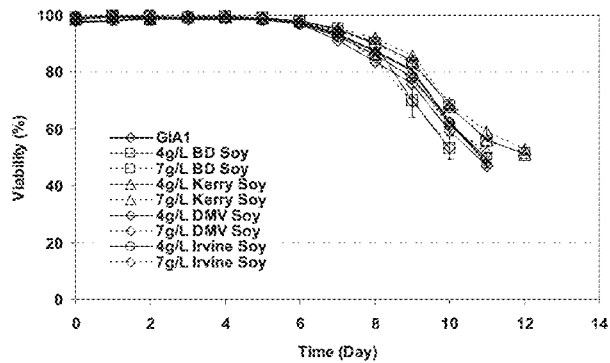
Figure 6C:
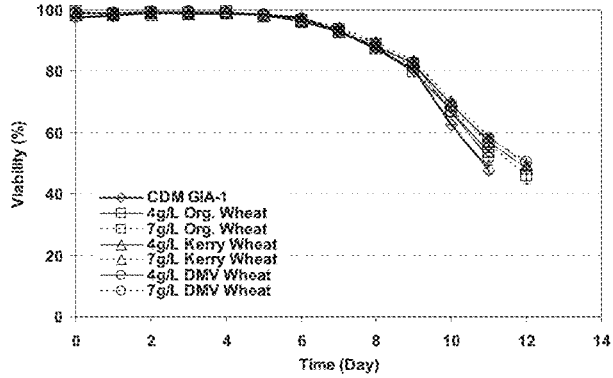

The combined addition of yeast and soy hydrolysates to various commercially available CD media lowered the percentage of NGA2F and NGA2F-GlcNac glycans by 2-10% compared to control (FIG. 4A): from 81% to 79% (HyClone CDM4CHO); from 80% to 75% (Irvine IS CHO-CD); from 88% to 80% (Life Technologies OptiCHO); from 90% to 80% (Life Technologies GIA-1). The percentage of NA1F and NA2F glycans increased by 3-8% compared to control (FIG. 4B): from 15% to 18% (HyClone CDM4CHO); from 6% to 12% (Life Technologies GIA-1); from 16% to 21% (Irvine IS CHO-CD); from 5% to 13% (Life Technologies OptiCHO).

Example 3

Yeast, Soy or Wheat Hydrolysates Addition to CD Media GIA-1 for Culture of an Adalimumab-Producing CHO Cell Line #1

In the study summarized in this example, we investigated the effects on glycosylation resulting from the addition of yeast (5, 11 g/L), soy (4, 7 g/L) or wheat (4, 7 g/L) hydrolysates from multiple vendors (BD Biosciences, Sheffield/Kerry Biosciences, DMV International, Irvine Scientific and Organotechnie) to CDM GIA-1 in the adalimumab-producing CHO cell line #1.

3.1 Materials and Methods

Adaptation and production media were supplemented with Bacto TC Yeastolate, BBL Phytone Peptone or Wheat Peptone E1 according to the experimental design in FIG. 41. The control cultures were not supplemented with hydrolysates. All media pH was adjusted to approximately 7.1 using 6N hydrochloric acid/5N sodium hydroxide. The media osmolality was adjusted to 290-300 mOsmol/kg with sodium chloride.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning, vented, non-baffled shake flasks at an initial VCD of approximately 0.5×$10^6$ cells/mL. The shake flask study was run in an extended-batch mode by feeding a glucose solution (1.25% (v/v) of 40% solution) when the media glucose concentration fell below 3 g/L.

3.2 Culture Growth and Productivity

Figure 7:
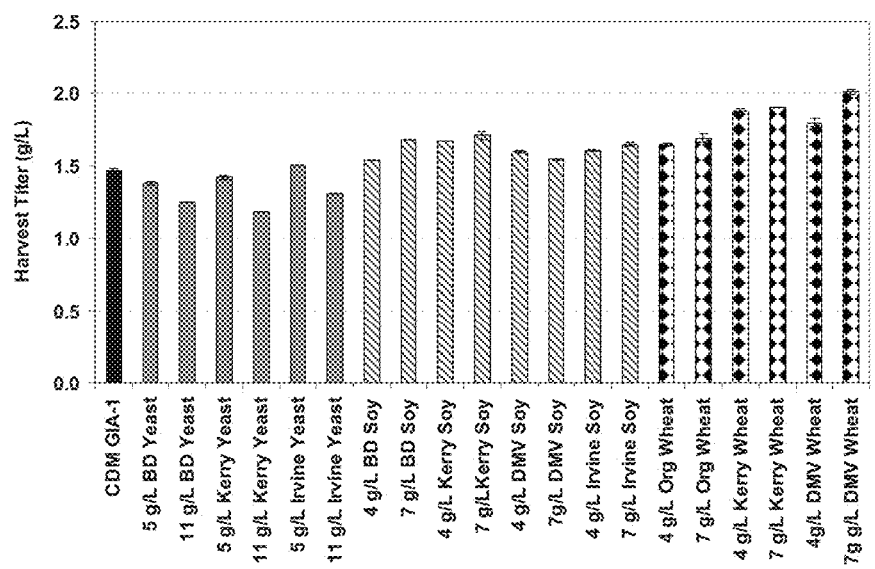
FIG. 7 depicts the effect of supplementing yeast, soy or wheat hydrolysate from multiple vendors to CDM GIA-1 on harvest titer in CHO cell line #1.

Culture growth and viability profiles were comparable among all test conditions (FIGS. 5A-C, 6A-C) except for 11 g/L BD Bacto TC yeastolate, for which a slight decrease in the growth rate and maximum VCD was observed. Supplementation of CD media GIA-1 with yeast hydrolysates lowered the harvest titer by up to 25% compared to the control, while the harvest titer increased up to 14% and 27% with the addition of soy or wheat hydrolysates, respectively (FIG. 7).

3.3 Oligosaccharide Analysis

Figure 8A:
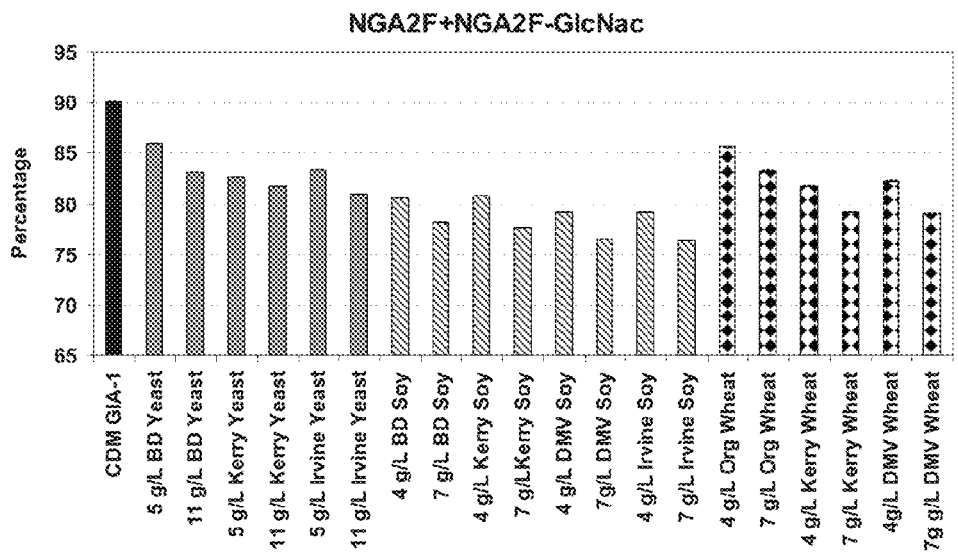
FIGS. 8A and 8B depict the effect of supplementing yeast, soy or wheat hydrolysate from multiple vendors to CDM GIA-1 in CHO cell line #1 on (FIG. 8A) NGA2F and (NGA2F-GlcNac) and (FIG. 8B) NA1F and NA2F, respectively.
Figure 8B:
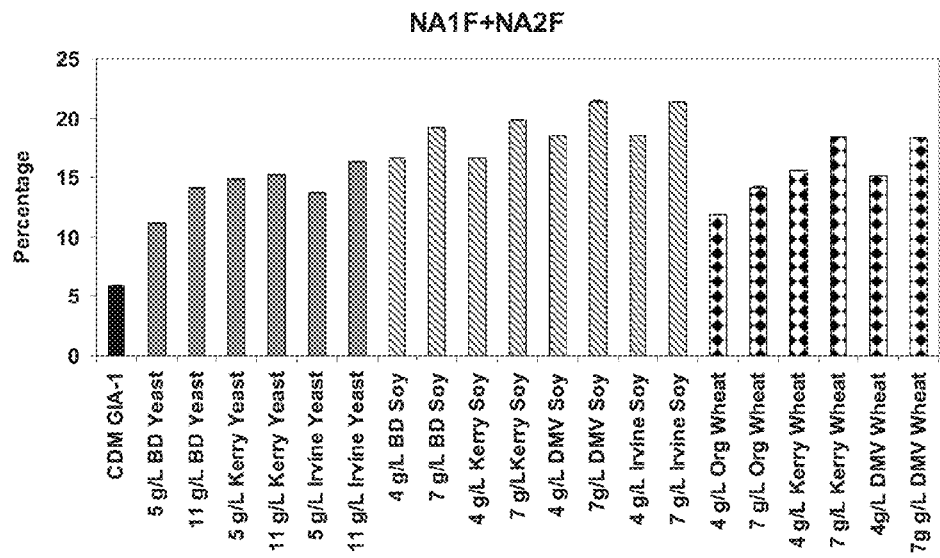

Addition of yeast, soy or wheat hydrolysates to CD media GIA-1 decreased the NGA2F and NGA2F-GlcNac glycans in a dose-dependent manner for all hydrolysate vendors evaluated (FIGS. 8A-B). Addition of yeast hydrolysates to CD media GIA-1 lowered the percentage of NGA2F and NGA2F-GlcNac glycans by 4-9% and increased the percentage of NA1F and NA2F glycans by 5-10% compared to control (NGA2F and NGA2F-GlcNac: 90%; NA1F and NA2F: 6%). Addition of soy hydrolysates to CD media GIA-1 decreased the NGA2F and NGA2F-GlcNac glycans by 9-14% and increased the NA1F and NA2F glycans by 11-15% compared to control. Addition of wheat hydrolysates decreased the NGA2F and NGA2F-GlcNac glycans by 4-11% and increased the NA1F and NA2F glycans by 6-12% compared to control.

Example 4

Control of Heterogeneity by Addition of Reduced Ratio of Yeast to Plant Hydrolysate To identify the role which the ratio of yeast to plant hydrolysate plays in connection with the generation of protein heterogeneity, experiments employing a range of different hydrolysate ratios were undertaken. The cell culture medium employed in each experimental process contains both yeast and soy hydrolysate (phytone). The ratios of yeast to soy hydrolysate (by weight) are 1.55, 0.67 and 0.25. The total weight of yeastolate and soy hydrolysate were not changed in each experimental process. Two distinct yeastolate lots were used in connection with these experiments (see FIGS. 9 & 11 and 10 & 12, respectively). Culture growth, productivity and product quality were assessed. As outlined in FIGS. 9-12, reducing the yeast to soy hydrolysate ratio resulted in altered oligosaccharide profiles.

4.1. Materials and Methods

The CHO cell line #1 was employed in the studies covered here. The production medium used in this experiment contains basal medium PFCHO, Bacto TC yeastolate and phytone peptone. The pH of all media was adjusted to 7.15; and media osmolality was adjusted to 373-403 mOsmol/kg with sodium chloride. For each experiment, 500 mL shakers with 200 mL working volume were employed at the following conditions: 35° C. constant temperature; 5% $CO_2$; and 110 RPM. Cultures were inoculated at an initial viable cell density (VCD) of approximately 0.5×$10^6$ cells/mL. Two mL of 40% w/w glucose solution was added to each shaker when the glucose concentration dropped below 2 g/L. The shakers were harvested when the viable cell density decreased to approximately 50%. The harvest broth was centrifuged at 3200 rpm for 30 min at 5° C. to remove cells and the supernatant was stored at −80° C.

Samples were taken daily from each shaker to monitor growth. The following equipment was used to analyze the samples: Cedex cell counter, Radiometer blood gas analyzer, YSI glucose analyzer and osmometer. The harvest samples stored at −80° C. were later thawed and analyzed for titer with Poros A HPLC method. In addition, the thawed samples were filtered through a 0.2 μm filter, purified by Protein A chromatography and then oligosaccharide analysis was performed as described in Example 1.

4.2 Cell Growth and Productivity

Figure 9A:
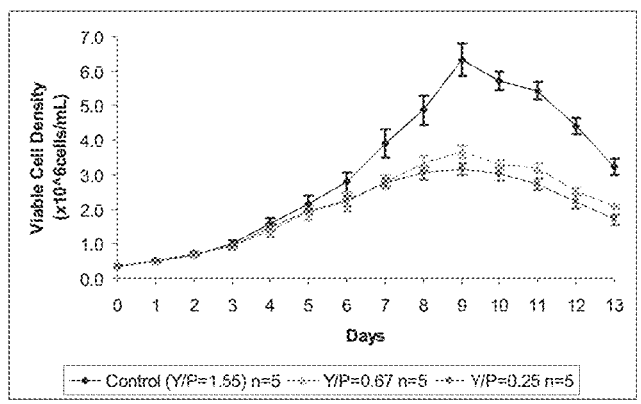
FIG. 9A depicts viable cell density and FIG. 9B depicts viability in Example 4: Hydrolysate study #1 using distinct ratios of yeast to soy hydrolysate in adalimumab-producing CHO cell line #1.
Figure 9B:
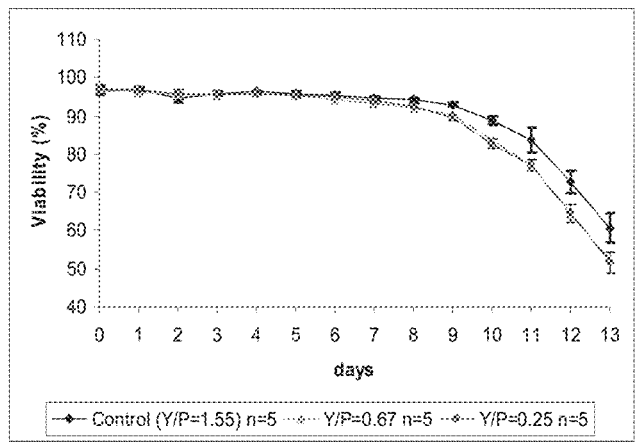
Figure 10A:
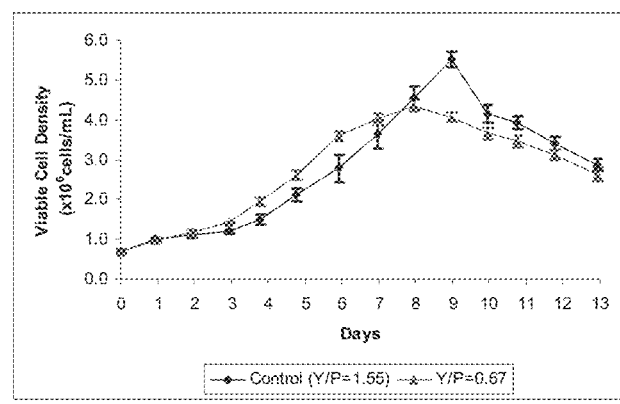
FIG. 10A depicts viable cell density and FIG. 10B depicts viability in Example 4: Hydrolysate study #2 using distinct ratios of yeast to soy hydrolysate in adalimumab-producing CHO cell line #1.
Figure 10B:
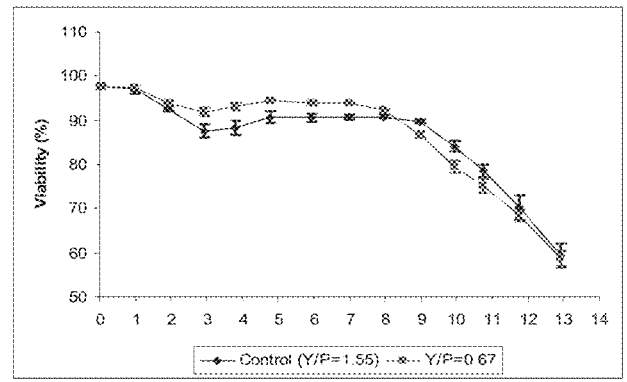

In the first hydrolysate study, the viable cell densities for the reduced ratios of yeastolate to phytone (i.e. Y/P=0.67 and Y/P=0.25) were much lower than the viable cell density for the 1.55 ratio of yeastolate to phytone (FIG. 9). As a result, the IVCC on day 13 (i.e. the harvest day) was significantly lower for the reduced ratio conditions compared to the 1.55 ratio condition and the titer was also lower (but not statistically significantly—data not shown). The viability profiles were comparable until day 8 (FIG. 9). After day 8, the viability declined faster for the reduced ratio conditions. In hydrolysate study 2, the viable cell density and viability for the 1.55 ratio were slightly lower than those with reduced ratio in the exponential phase, but higher in the decline phase (FIG. 10). However, the titer for the 1.55 ratio shaker was 0.2 g/L lower than the reduced ratio (i.e. Y/P=0.67) (data not shown).

4.3. Oligosaccharide Analysis

Glycosylation profiles for hydrolysate studies 1 and 2 are shown in FIGS. 11 and 12, respectively. Reducing the ratio of yeastolate to phytone reduced the percentage of NGA2F and (NGA2F-GlcNAc) glycan. In hydrolysate study 1, the percentage of NGA2F and (NGA2F-GlcNAc) was significantly reduced for Y/P=0.67 and Y/P=0.25 as compared to Y/P=1.55. The p values were 0.03 and 0.001 for Y/P=0.67 and Y/P=0.25, respectively. At the same time, the percentage of NA1F and NA2F was increased significantly as the ratio of yeastolate to phytone was reduced.

As shown in FIG. 12 in hydrolysate study 2, the difference in the percentage of NGA2F and (NGA2F-GlcNAc) between Y/P=0.67 and Y/P=1.55 was significant (i.e. p=0.000002). The percentage of NGA2F and (NGA2F-GlcNAc) was lowered from 77.5% in the 1.55 ratio to approximately 75.4% with the reduced ratio.

Therefore, this study successfully demonstrated that reducing the ratio of yeastolate to phytone could alter oligosaccharide profile using two different lots of yeast hydrolysate.

Example 5

Control of Heterogeneity by Supplementation with Asparagine

The present invention relates to methods for modulating the glycosylation profile of a monoclonal antibody (mAb) by varying the concentration of asparagine in cell culture media. Cell culture medium components, such as asparagine, are commonly used and are typical constituents of suspension culture media. These nutrients are important for ensuring both robust cell growth and production of glycoproteins. It has been shown that the cell viability and product titer can be enhanced by the addition of asparagine to a glutamine-free production medium (Genentech, Inc. "Production of Proteins in Glutamine-Free Cell Culture Media" WO2011019619 (2010)). However, the present invention provides methods to modify glycosyaltion distribution by adjusting the concentration of asparagine. Without being bound by theory, it is thought that the effect of asparagine on glycosylation profile of an antibody is through its conversion to glutamine and/or aspartate. Asparagine is the amide donor for glutamine and can be converted to glutamine and/or aspartate (H Huang, Y Yu, X Yi, Y Zhang "Nitrogen metabolism of asparagine and glutamate in Vero cells studied by 1H/15N NMR spectroscopy" Applied microbiology and biotechnology 77 (2007) 427-436). Glutamine and aspartate are important intermediates in pyrimidine synthesis; and it is known that enhancing de novo pyrimidine biosynthesis could increase intracellular UTP concentration (Genentech, Inc. "Galacosylation of Recombinant Glycoproteins" US20030211573 (2003)). In addition, studies have suggested that glutamine and aspartate limitation is expected to inhibit amino sugar synthesis (G B Nyberg, R R Balcarcel, B D Follstad, G Stephanopoulos, D I Wang "Metabolic effects on recombinant interferon-gamma glycosylation in continuous culture of Chinese hamster ovary cells" Biotechnology and Bioengineering 62 (1999) 336-47; D C F Wong, K T K Wong, L T Goh, C K Heng, M G S. Yap "Impact of dynamic online fed-batch strategies on metabolism, productivity and N-glycosylation quality in CHO cell cultures" Biotechnology and Bioengineering 89 (2005) 164-177). Both UTP and amino sugar are required for the synthesis of UDP-GlcNac, which is the substrate for protein glycosylation process. It is also possible that the effect of asparagine on glycosyaltion is via increasing ammonia concentration in the cell culture medium since it is showed that the addition of ammonia in CHO cultures could reduce the extent of glycosylation of synthesized EPO (M. Yang and M. Butler "Effect of Ammonia on the Glycosylation of Human Recombinant Erythropoietin in Culture" Biotechnol. Prog. 16 (2000) 751-759). We have found that ammonia concentration was increased after asparagine addition into the cell culture media.

In the studies summarized in Example 5, we investigated the effects on product quality attributes resulting from the addition of asparagine to hydrolysate based medium in an adalimumab-producing CHO cell line, generically named CHO cell line #1. Two experiments were performed in the instant Example. For the first experiment, glutamine and/or asparagine were added (at an individual concentration of 0.4 g/L) on day 6. For the second experiment, asparagine was added at different dosage (i.e. 0.4 g/L, 0.8 g/L or 1.6 g/L) either on day 0 (before inoculation) or together with the first glucose shot (happened on day 7).

5.1 Materials and Methods

The CHO cell line #1 was employed in the studies covered here. Upon thaw, cells were expanded in a 19-days seed train and then transferred into seed reactors for up to 7 days in growth medium. The cells were then brought to the laboratory and used in the small scale bioreactor experiments. The media used in these experiments contains basal media PFCHO (proprietary formulation), Bacto TC Yeastolate and Phytone Peptone.

Three litter Applikon bioreactors were sterilized and then charged with production medium. At inoculation, cells were aseptically transferred into each bioreactor to reach an initial cell density of $0.5 \times 10^6$ viable cells/mL. After inoculation, the bioreactors were set to the following conditions: pH=7.1, T=35° C., DO=30% and agitation=200 rpm. The pH was shifted from 7.1 to 6.9 over the first 2.5 days and held at 6.9 for the remainder of the run. The percentage of dissolved oxygen was controlled by sparging a mixture of air and oxygen. The addition of 0.5 N NaOH or sparging of $CO_2$ maintained the pH. When the glucose concentration fell below 2 g/L, approximately 1.25% (v/v) of glucose solution (400 g/kg) was added to the cell culture.

For the first experiment, glutamine and/or asparagine were added (at an individual concentration of 0.4 g/L) together with the first glucose shot (happened on day 6). For the second experiment, asparagine was added at different dosage (i.e., 0.4 g/L, 0.8 g/L or 1.6 g/L) either on day 0 (before inoculation) or together with the first glucose shot (happened on day 7).

Samples were taken daily from each reactor to monitor growth. The following equipment was used to analyze the samples: Cedex cell counter for cell density and viability;

Radiometer ABL 5 blood gas analyzer for pH, pCO2 and pO2; YSI 7100 analyzer for glucose and lactate concentration. Some of the daily samples and the harvest samples were centrifuged at 3,000 RPM for 30 min and then the supernatants were stored at −80° C. Later, the thawed harvest samples were filtered through a 0.2 μm filter, purified by Protein A chromatography and then oligosaccharide analysis was performed and then oligosaccharide analysis was performed as described in Example 1.

5.2 Culture growth and Productivity

Figure 13A:
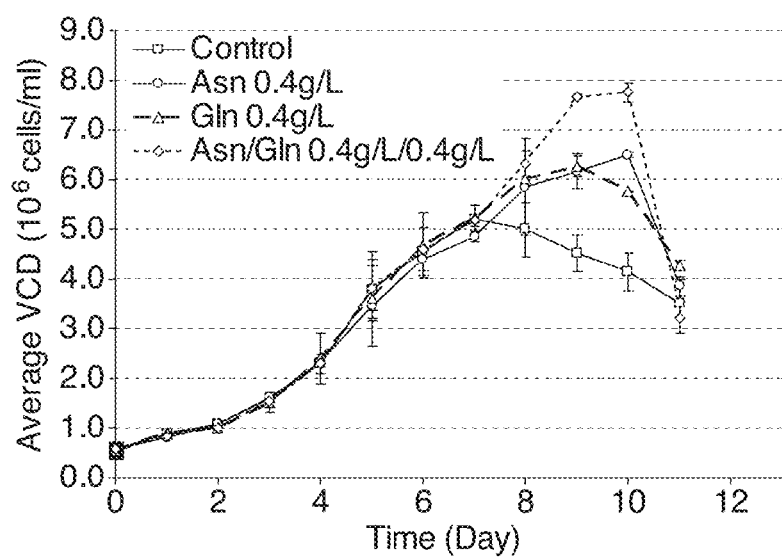
FIGS. 13A-13C depict the effect of supplementation of asparagine and/or glutamine on day 6 to hydrolysate based media in CHO cell line #1 on culture growth (FIG. 13A), culture viability (FIG. 13B) and product titer (FIG. 13C), respectively.
Figure 15A:
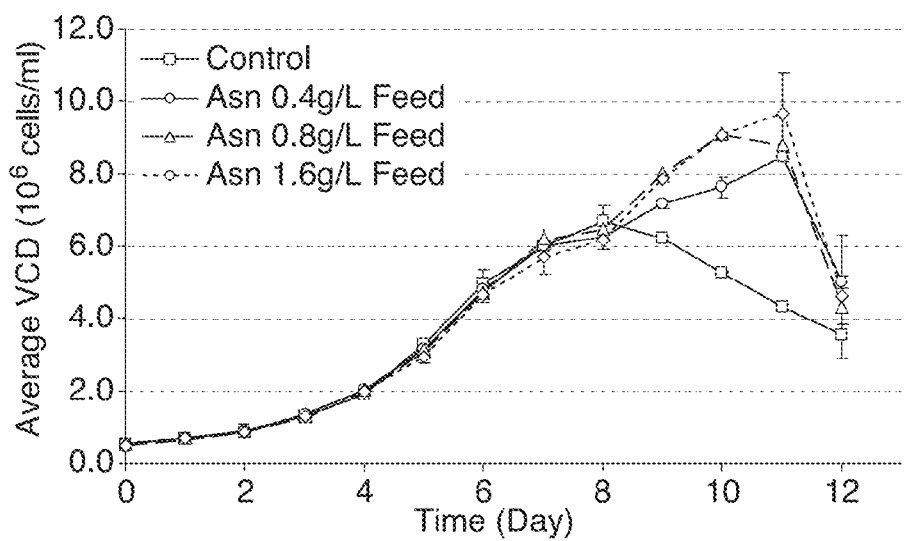
FIGS. 15A-15C depict the dose dependent effect of supplementation of asparagine on Day 7 to hydrolysate based media in adalimumab-producing CHO cell line #1 on culture growth (FIG. 15A), culture viability (FIG. 15B) and product titer (FIG. 15C), respectively.
Figure 17A:
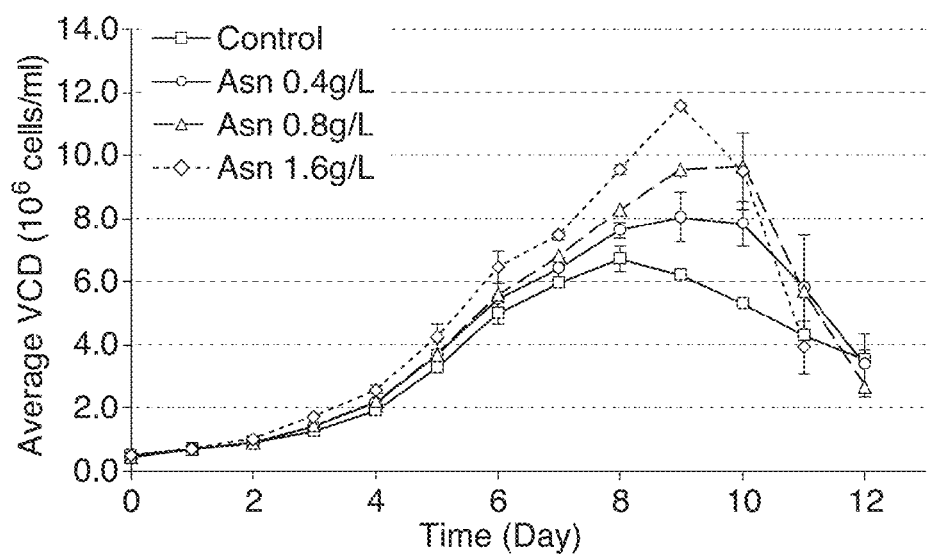
FIGS. 17A-17C depict the dose dependent effect of supplementation of asparagine on Day 0 to hydrolysate based media in adalimumab-producing CHO cell line #1 on culture growth (FIG. 17A), culture viability (FIG. 17B) and product titer (FIG. 17C), respectively.

In both of the experiments performed in 3 L bioreactor in hydrolysate based media with CHO cell line #1 described in the instant Example, the addition of glutamine and/or asparagine together with a glucose shot increased the maximum cell density (FIGS. 13A and 15A, respectively). The increase in cell density is started two days after the addition in both cases. Maximum viable cell density was consistent when 0.4 g/L of glutamine or asparagine was added. Increasing the concentration of asparagine to 0.8 g/L or adding both glutamine and asparagine at a concentration of 0.4 g/L each further increased the maximum viable cell density; however, adding asparagine at a higher concentration than 0.8 g/L (e.g., 1.6 g/L) did not continue to increase the maximum viable cell density. In contrast, when asparagine was added on day 0 (before inoculation), the maximum viable cell density increased in a dose dependent manner, with the maximum viable cell density being reached when 1.6 g/L of asparagine was added on day 0 (FIG. 17A).

Figure 13B:
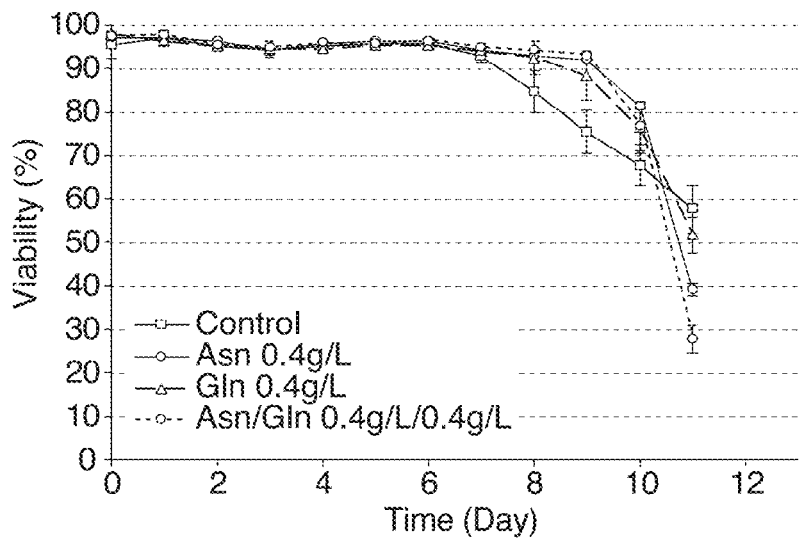
Figure 13C:
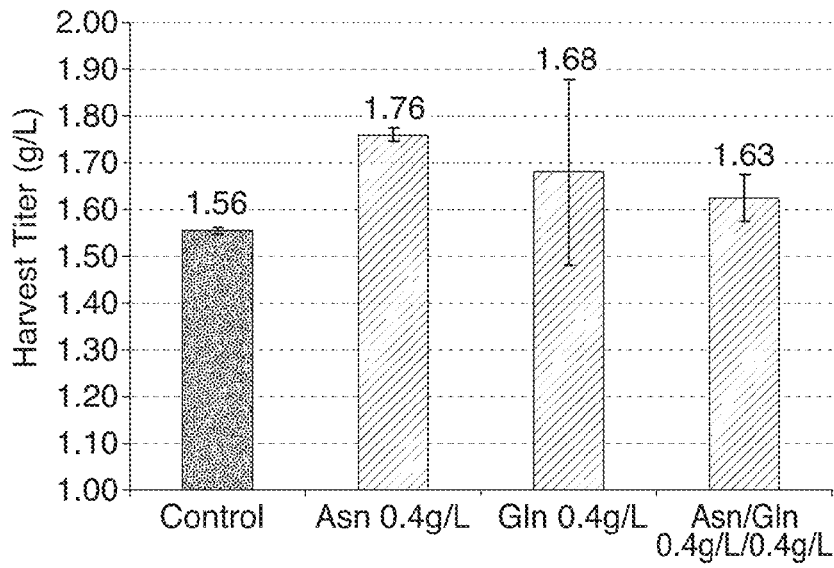
Figure 14A:
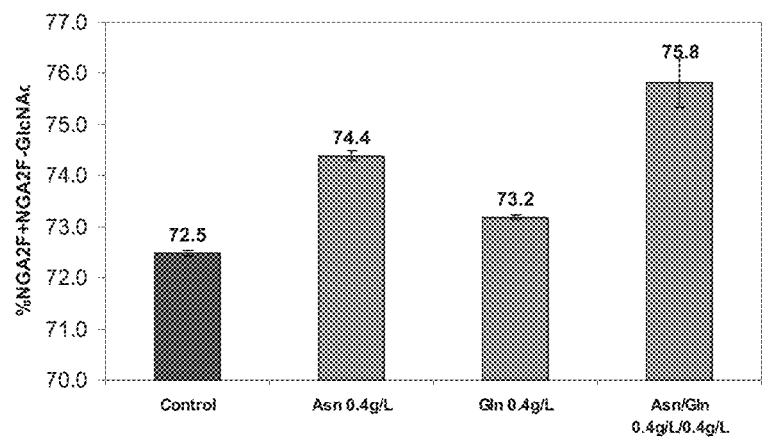
FIGS. 14A and 14B depict the effect of supplementation of asparagine and/or glutamine on Day 6 to hydrolysate based media in adalimumab-producing CHO cell line #1 on NGA2F and (NGA2F-GlcNac) glycans (FIG. 14A) and on NA1F and NA2F glycans (FIG. 14B), respectively.
Figure 14B:
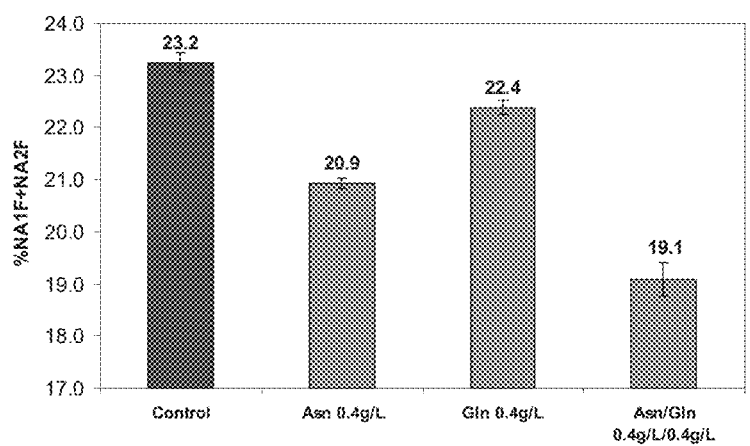
Figure 15B:
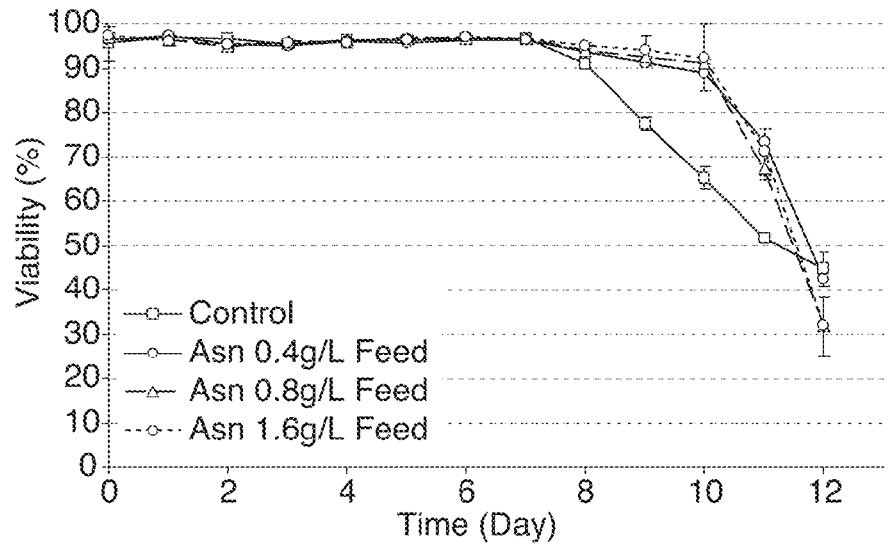
Figure 15C:
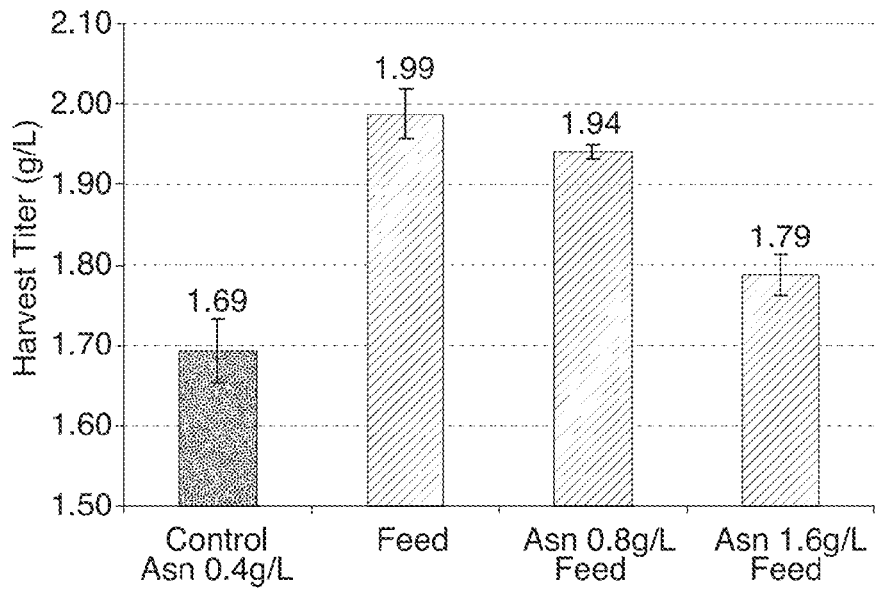
Figure 16A:
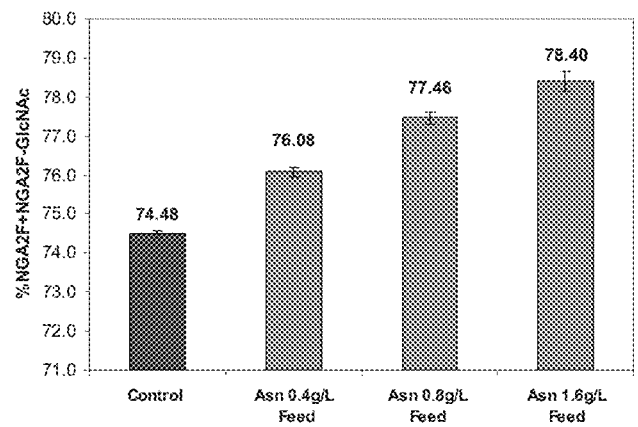
FIGS. 16A and 16B depict the dose dependent effect of supplementation of asparagine on Day 7 to hydrolysate based media in adalimumab-producing CHO cell line #1 on NGA2F and (NGA2F-GlcNac) glycans (FIG. 16A) and on NA1F and NA2F glycans (FIG. 16B), respectively.
Figure 16B:
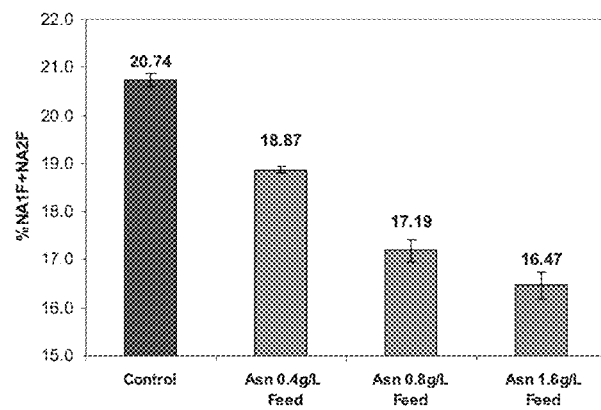
Figure 17B:
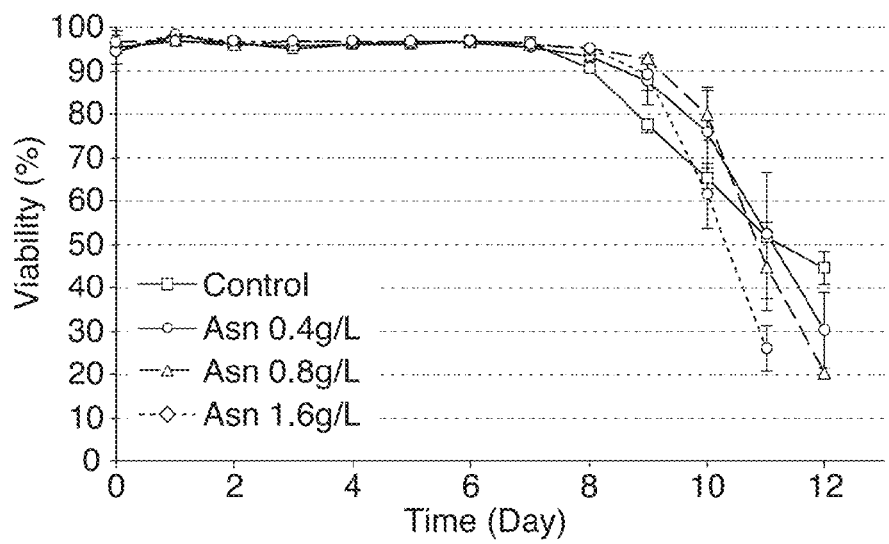
Figure 17C:
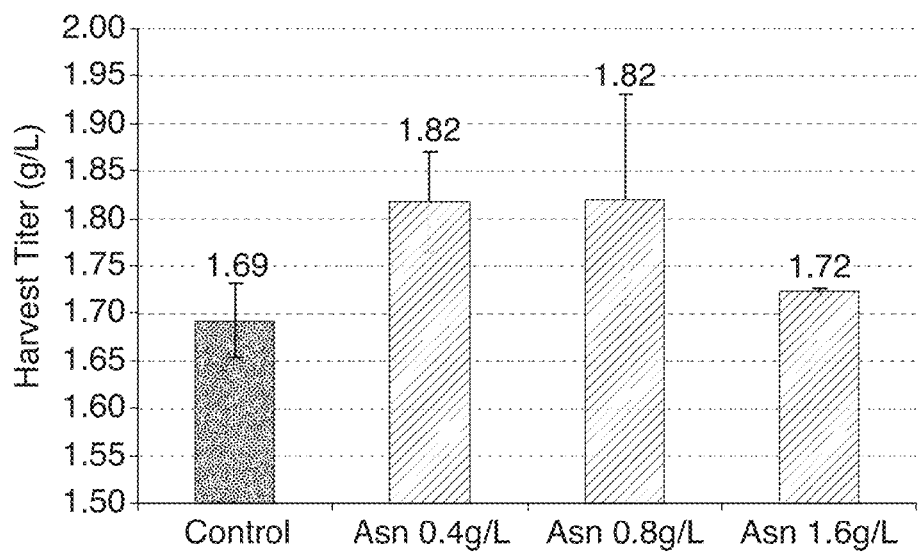
Figure 18A:
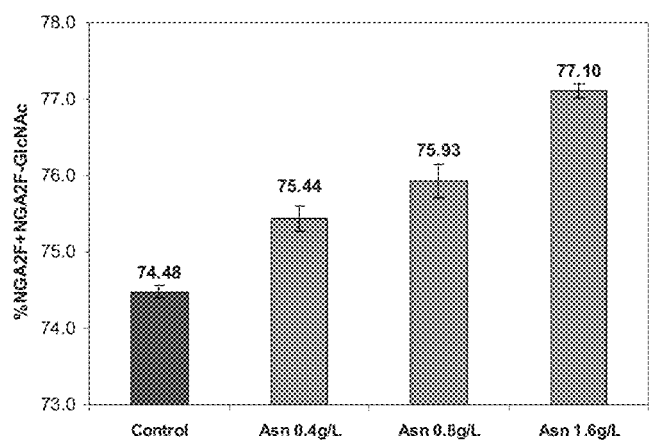
FIGS. 18A and 18B depict the dose dependent effect of supplementation of asparagine on Day 0 to hydrolysate based media in adalimumab-producing CHO cell line #1 on NGA2F and (NGA2F-GlcNac) glycans (FIG. 18A) and on NA1F and NA2F glycans (FIG. 18B), respectively.
Figure 18B:
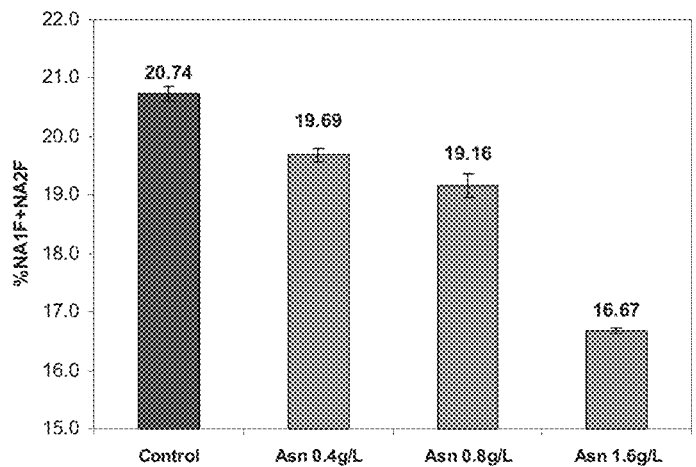

A drop in viability was delayed, as compared to control cultures, in both experiments described in the instant Example for approximately 3 days when glutamine and/or asparagine was added on day 6 or 7 (FIGS. 13B and 15B, respectively). However, the drop in viability accelerated on the last day of the cultures. In contrast, although the drop in viability was delayed when asparagine was added on day 0, the effect of delaying viability decay was not as efficient as when the amino acids were added later (e.g., on day 6 or day 7) as shown in FIG. 17B.

5.3 Oligosaccharide Analysis

The experiments described in the instant Example indicate that oligosaccharide distribution is altered with the addition of asparagine and/or glutamine. The addition of asparagine increased NGA2F and NGA2F-GlcNac in a dose dependent manner. Compared to control, the percentage of NGA2F and NGA2F-GlcNac was increased by 1.0-3.9% and the percentage of NA1F and NA2F was decreased by 1.1-4.3% when 0.4 to 1.6 g/L asparagine was added on either day 0 or days 6 or 7 (FIGS. 14A-14B, 16A-16B and 18A-18B). Addition of 0.4 g/L glutamine increased the percentage of NGA2F and NGA2F-GlcNac by 0.7% and lowered the percentage of NA1F and NA2F by 0.9%. Adding both asparagine and glutamine (0.4 g/L of each) increased the percentage of NGA2F and NGA2F-GlcNAc by 3.3% and decreased the percentage of NA1F and NA2F by 4.2%. In addition, the cell growth profile is the same when 0.8 and 1.6 g/L of asparagine was added on day 7 (FIGS. 15A and 15B), but a dose dependent effect on oligosaccharide distribution was observed (FIGS. 16A and 16B), indicating that the effect on oligosaccharide distribution was due to the addition of asparagine and not the increased maximum viable cell density or delayed drop in viability.

Example 6

Yeast, Soy or Wheat Hydrolysate Addition to Commercially Available CD Media is CHO-CD for Culture of an Adalimumab-Producing CHO Cell Line #1

In the study summarized in this example, the effects on glycosylation resulting from the addition of yeast, soy or wheat hydrolysates to CD media IS CHO-CD (Irvine Scientific) in the adalimumab-producing CHO cell line #1 utilized in Example 1 were evaluated.

6.1 Materials and Methods

Adaptation and production media (Irvine Scientific IS CHO-CD 91119) were supplemented with Bacto TC Yeastolate, BBL Phytone Peptone or Wheat Peptone E1 according to the experimental design in FIG. 42. The control cultures were not supplemented with hydrolysates. All media pH was adjusted to approximately 7.1.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning vented non-baffled shake flasks at an initial VCD of approximately $0.5 \times 10^6$ cells/mL. The shake flask study was run in an extended-batch mode by feeding a glucose solution (1.25% (v/v) of 40% solution) when the media glucose concentration fell below 3 g/L.

6.2 Culture Growth and Productivity

Figure 19A:
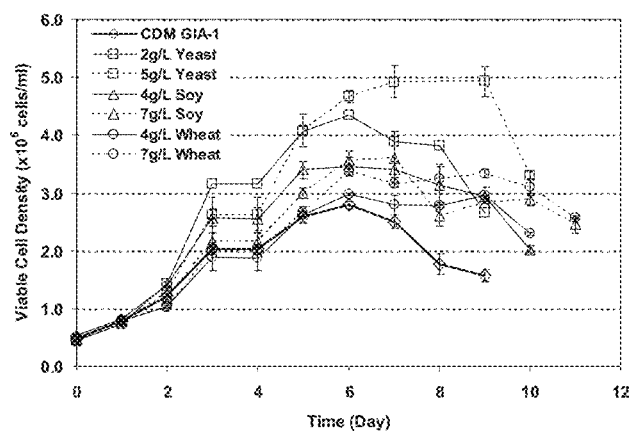
FIGS. 19A-19C depict the effect of yeast, soy or wheat hydrolysate addition to CDM Irvine IS CHO-CD in adalimumab-producing CHO cell line #1 on (FIG. 19A) Culture growth, (FIG. 19B) Culture viability and (FIG. 19C) Harvest titer, respectively.
Figure 19B:
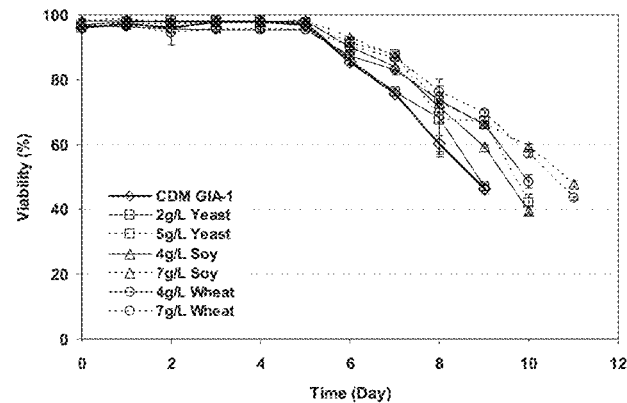
Figure 19C:
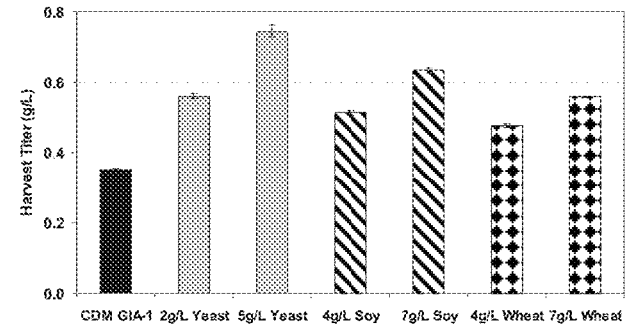

Addition of yeast, soy or wheat hydrolysates to Irvine IS CHO-CD media increased the maximum VCD and culture length for most conditions studied compared to the control (FIG. 19A). The largest increase in maximum VCD was recorded for cultures supplemented with 5 g/L Bacto TC Yeastolate. A concentration-dependent increase in harvest titer was observed for all cultures supplemented with hydrolysates (FIG. 19C).

6.3 Oligosaccharide Analysis

Figure 20A:
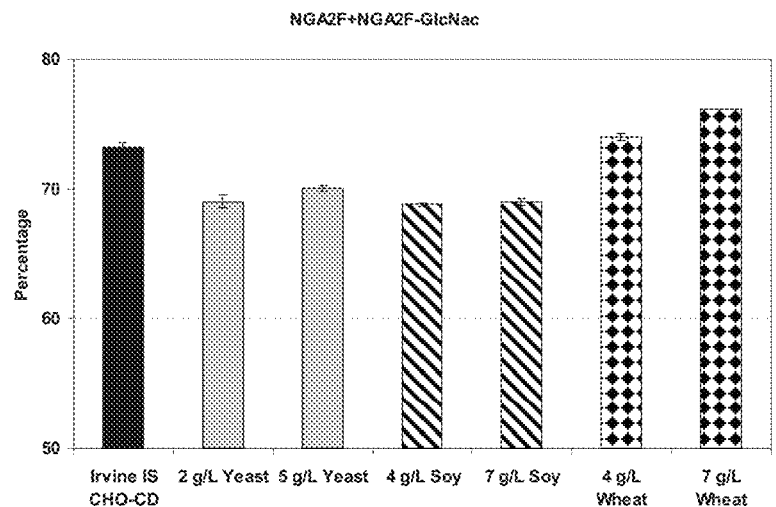
FIGS. 20A and 20B depict the effect of yeast, soy or wheat hydrolysates addition to CDM Irvine IS CHO-CD in adalimumab-producing CHO cell line #1 on oligosaccharides profile (FIG. 20A) NGA2F and (NGA2F-GlcNac) and (FIG. 20B) NA1F and NA2F, respectively.
Figure 20B:
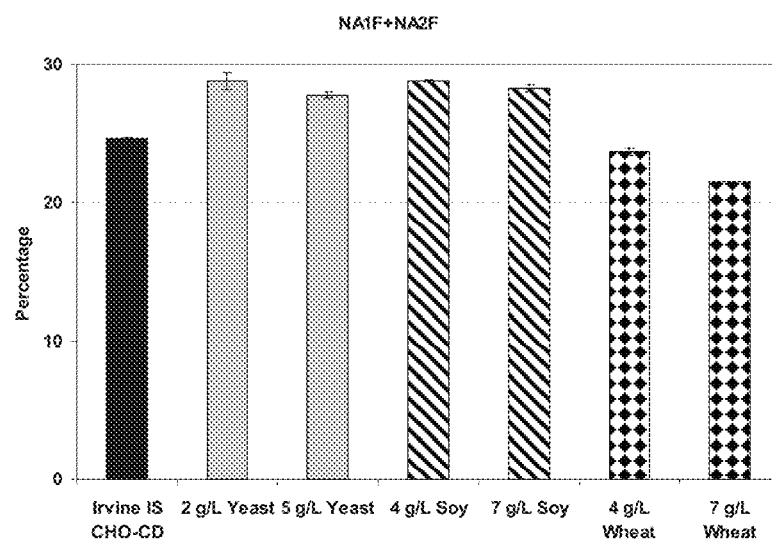

Supplementation of Irvine IS CHO-CD media with yeast hydrolysates decreased the percentage of NGA2F and NGA2F-GlcNac glycans by 3-4% and increased the percentage of NA1F and NA2F glycans by the same percentage compared to control (NGA2F and NGA2F-GlcNac: 73%; NA1F and NA2F: 25%) (FIGS. 20A-B). Addition of soy hydrolysates to Irvine IS CHO-CD media decreased the percentage of NGA2F and NGA2F-GlcNac glycans by 4% and increased the percentage of NA1F and NA2F glycans by the same percentage compared to control. However, addition of wheat hydrolysates to Irvine IS CHO-CD media resulted in an opposite trend. A concentration-dependent increase in the percentage of NGA2F and NGA2F-GlcNac glycans by 1-3% and a corresponding decrease in the percentage of NA1F and NA2F glycans was observed.

Example 7

Yeast, Soy or Wheat Hydrolysate Addition to CD Media GIA-1 for Culture of an Adalimumab-Producing CHO Cell Line #2

In the study summarized in this example, the effects on glycosylation resulting from the addition of yeast, soy or wheat hydrolysates to CD media GIA-1 in an adalimumab-producing CHO cell line, generically named CHO cell line #2 were evaluated. The antibody produced by the adalimumab-producing CHO cell line #2 was identified as mAb #2.

7.1 Materials and Methods

Adaptation and production media were supplemented with Bacto TC Yeastolate, BBL Phytone Peptone or Wheat Peptone E1 according to the experimental design in FIG. 43. The control cultures were not supplemented with hydrolysates. All media pH was adjusted to approximately 7.1 and the media osmolality was adjusted to 290-300 mOsmol/kg.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 180 RPM in a 35° C., 5% $CO_2$ dry incubator. Production cultures were initiated in duplicate 500 mL (200 mL working volume) Corning vented non-baffled shake flasks at an initial VCD of approximately $0.5\times10^6$ cells/mL. The shake flask study was run in an extended-batch mode by feeding a glucose solution (1.25% (v/v) of 40% solution) when the media glucose concentration fell below 3 g/L.

7.2 Culture Growth and Productivity

Figure 21A:
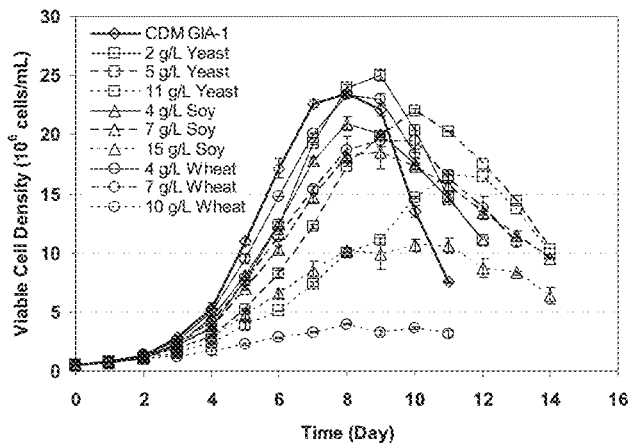
FIGS. 21A-21C depict the effect of yeast, soy or wheat hydrolysate addition to CDM GIA-1 in adalimumab-producing CHO cell line #2 on (FIG. 21A) Culture growth, (FIG. 21B) Culture viability and (FIG. 21C) Harvest titer, respectively.
Figure 21B:
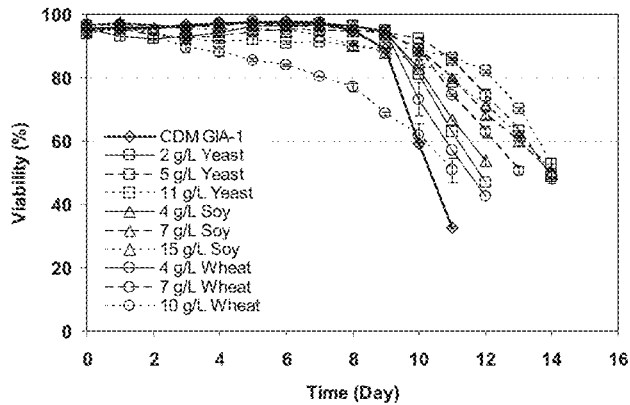
Figure 21C:
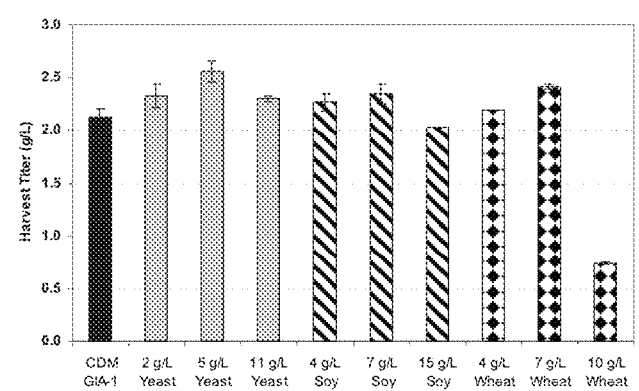

Supplementation of yeast, soy or wheat hydrolysates to CD media GIA-1 extended the culture length by 1 to 3 days and decreased the maximum VCD in a dose-dependent manner (FIGS. 21A-B). The addition of these hydrolysates at the highest concentrations significantly decreased maximum VCD, with wheat hydrolysates added at 10 g/L showing the most severe growth inhibition effects. However, an impact on harvest titer was only observed for the culture supplemented with 10 g/L wheat hydrolysates (65% reduction). An increase in the harvest titer compared to the control (FIG. 21C) was found in most other cultures.

7.3 Oligosaccharide Analysis

Figure 22A:
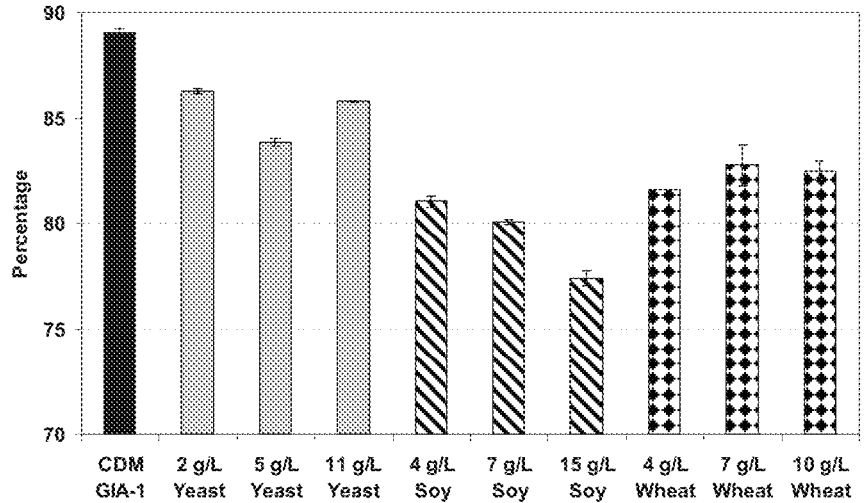
FIGS. 22A and 22B depict the effect of yeast, soy or wheat hydrolysate addition to CDM GIA-1 in adalimumab-producing CHO cell line #2 on (FIG. 22A) NGA2F and (NGA2F-GlcNac) and (FIG. 22B) NA1F and NA2F, respectively.
Figure 22B:
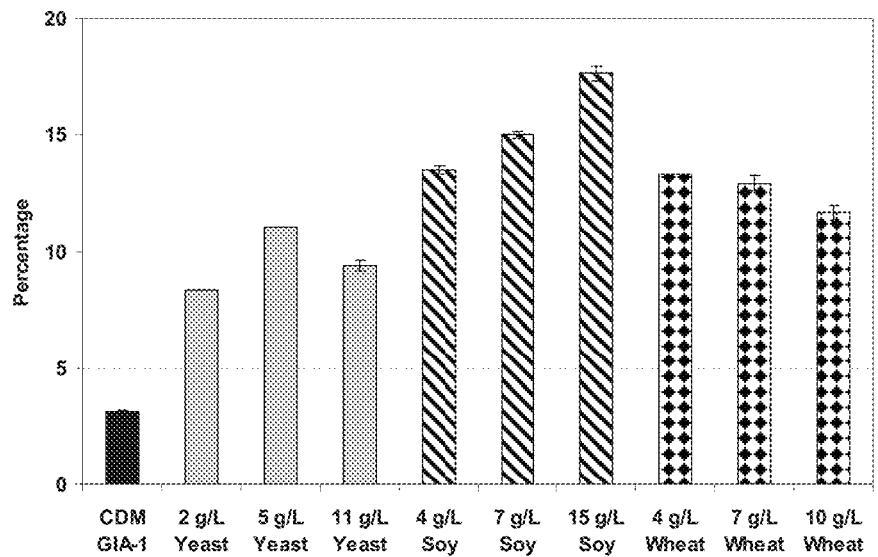

Addition of yeast hydrolysates decreased the percentage of NGA2F and NGA2F-GlcNac glycans by 3-5% and increased the percentage of NA1F and NA2F glycans by 5-8% compared to control (NGA2F and NGA2F-GlcNac: 89%; NA1F and NA2F: 3%) (FIGS. 22A-B). Addition of soy hydrolysates to CD media GIA-1 decreased the NGA2F and NGA2F-GlcNac glycans by 8-12% and increased the NA1F and NA2F glycans by 10-15% compared to control. Addition of wheat hydrolysates decreased the NGA2F and NGA2F-GlcNac glycans by 6-7% and increased the NA1F and NA2F glycans by 9-10% compared to control.

Example 8

Yeast, Soy or Wheat Hydrolysate Addition to CD Media GIA-1 for Culture of an Adalimumab-Producing CHO Cell Line #3

In the study summarized in this example, the effects on glycosylation resulting from the addition of yeast, soy or wheat hydrolysates to CD media GIA-1 in an adalimumab-producing CHO cell line, generically named CHO cell line #3 were evaluated.

8.1 Materials and Methods

Adaptation and production media were supplemented with Bacto TC Yeastolate, BBL Phytone Peptone or Wheat Peptone E1 according to the experimental design in FIG. 44. The control cultures were not supplemented with hydrolysates. All media pH was adjusted to approximately 7.1 and the media osmolality was adjusted to 290-300 mOsmol/kg.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 140 RPM in a 36° C., 5% $CO_2$ dry incubator. Production cultures were initiated in duplicate 500 mL (200 mL working volume) Corning vented non-baffled shake flasks at an initial VCD of approximately $0.5\times10^6$ cells/mL. The shake flask study was run in an extended-batch mode by feeding a glucose solution (1.25% (v/v) of 40% solution) when the media glucose concentration fell below 3 g/L.

8.2 Culture Growth and Productivity

Figure 23A:
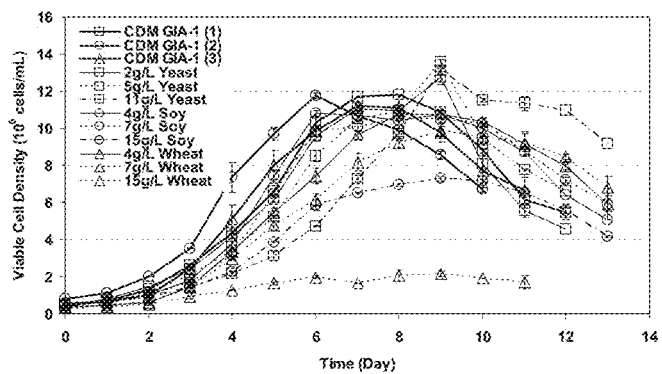
FIGS. 23A-23C depict the effect of yeast, soy or wheat hydrolysate addition to CDM GIA-1 in adalimumab-producing CHO cell line #3 on (FIG. 23A) Culture growth, (FIG. 23B) Culture viability and (FIG. 23C) Harvest titer, respectively.
Figure 23B:
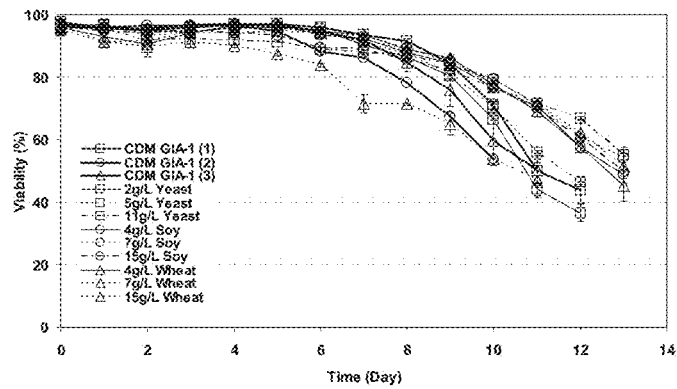
Figure 23C:
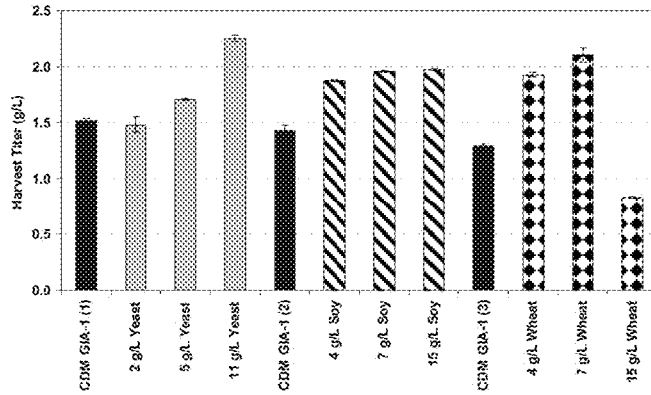

Supplementation of production CD media with high concentrations of hydrolysates—11 g/L yeast, 15 g/L soy or 15 g/L wheat hydrolysates, decreased the culture growth rate and increased the culture length compared to the control (FIGS. 23A-B). Harvest titer increased with increasing hydrolysate concentrations in the production media, except for the condition supplemented with 15 g/L wheat hydrolysates, which experienced significant growth inhibition and harvest titer decrease compared to control (FIG. 23C).

8.3 Oligosaccharide Analysis

Figure 24A:
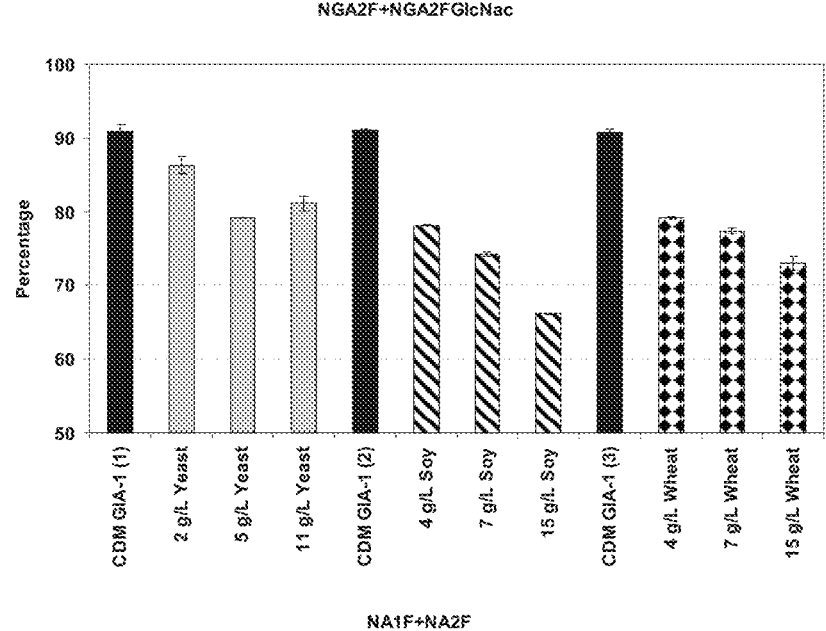
FIGS. 24A and 24B depict the effect of yeast, soy or wheat hydrolysate addition to CDM GIA-1 in adalimumab-producing CHO cell line #3 on (FIG. 24A) NGA2F and (NGA2F-GlcNac) and (FIG. 24B) NA1F and NA2F, respectively.
Figure 24B:
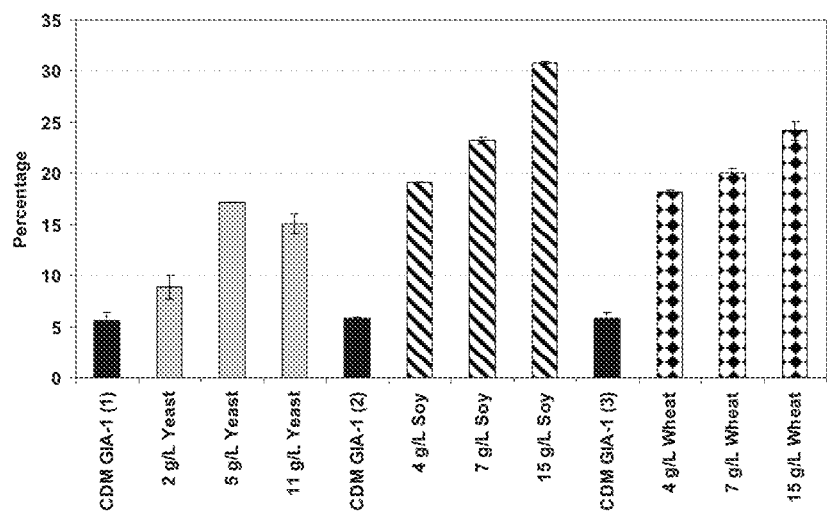

Supplementation of CD media GIA-1 with yeast, soy or wheat hydrolysates decreased the percentage of NGA2F and NGA2F-GlcNac glycans and increased the percentage of NA1F and NA2F glycans in a dose-dependent manner (FIGS. 24A-B). Addition of yeast hydrolysates decreased the percentage of NGA2F and NGA2F-GlcNac glycans by 5-12% and increased the percentage of NA1F and NA2F glycans by 3-11% compared to control (NGA2F and NGA2F-GlcNac: 91%; NA1F and NA2F: 6%). Addition of soy hydrolysates to CD media GIA-1 decreased the NGA2F and NGA2F-GlcNac glycans by 13-25% and increased the NA1F and NA2F glycans by 13-25% compared to control. Addition of wheat hydrolysates decreased the NGA2F and NGA2F-GlcNac glycans by 12-18% and increased the NA1F and NA2F glycans by 12-18% compared to control.

Example 9

Yeast, Soy or Wheat Hydrolysate Addition to CD Media GIA-1 for Culture of a CHO Cell Line Producing mAb #1

In the studies summarized in this example, the effects on glycosylation resulting from the addition of yeast, soy or wheat hydrolysates to CD media GIA-1 in a CHO cell line producing mAb #1 were evaluated.

9.1 Materials and Methods

Adaptation and production media were supplemented with Bacto TC Yeastolate (BD Biosciences; catalog #255772), BBL Phytone Peptone (BD Biosciences; catalog #211096) or Wheat Peptone E1 (Organotechnie; catalog #19559) according to the experimental design in FIG. 45. The control cultures were not supplemented with hydrolysates. All media pH was adjusted to approximately 7.2 and the media osmolality was adjusted to 290-330 mOsmol/kg.

Cultures were expanded for 4 passages (3 days each) in their respective adaptation media in a combination of 250 mL (50 mL or 100 mL working volume) and 500 mL (150 mL working volume) Corning vented non-baffled shake flasks and maintained on an Infors Multitron orbital shaker at 140 RPM in a 36° C., 5% $CO_2$ incubator. Production cultures were initiated in duplicate 500 mL (200 mL working volume) Corning vented non-baffled shake flasks at approximately $1.0\times10^6$ cells/mL initial VCD. The study was run in an extended-batch mode by feeding a glucose solution (1.0% (v/v) of 40% solution) when the media glucose concentration fell below 3 g/L.

9.2 Culture Growth and Productivity

Figure 25A:
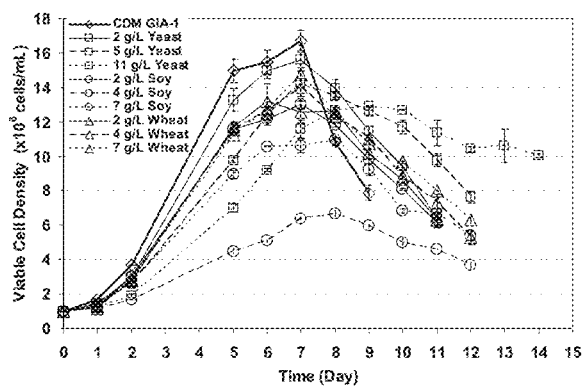
FIGS. 25A-25C depict the effect of yeast, soy or wheat hydrolysate addition to CDM GIA-1 in CHO cell line producing mAb #1 on (FIG. 25A) Culture growth, (FIG. 25B) Culture viability and (FIG. 25C) Harvest titer, respectively.
Figure 25B:
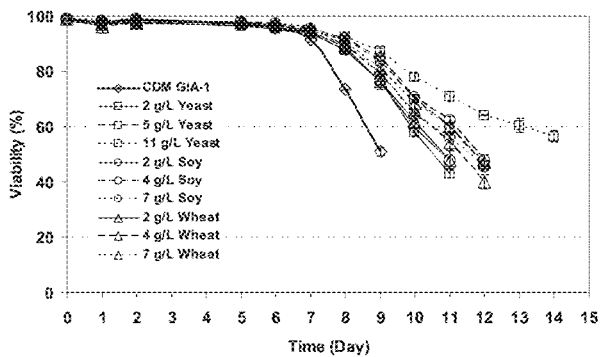
Figure 25C:
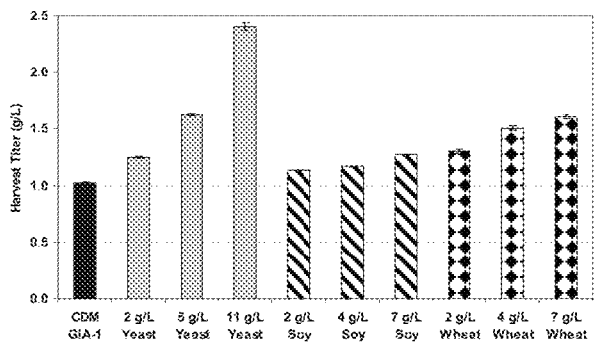

Supplementation of yeast, soy or wheat hydrolysates to the CD media GIA-1 did not affect culture growth profiles dramatically (FIGS. 25A-B). There was some dose-dependent reduction of the peak VCD compared to control as the hydrolysate concentrations increased, particularly in the case of soy hydrolysates, but overall the growth profiles were similar. However, the culture duration was extended to 11-14 days compared to 9 days for control. Cultures supplemented with 11 g/L yeast hydrolysate had a substantial increase in harvest titer (FIG. 25C) that far exceeded the other conditions.

9.3 Oligosaccharide Analysis

Figure 26A:
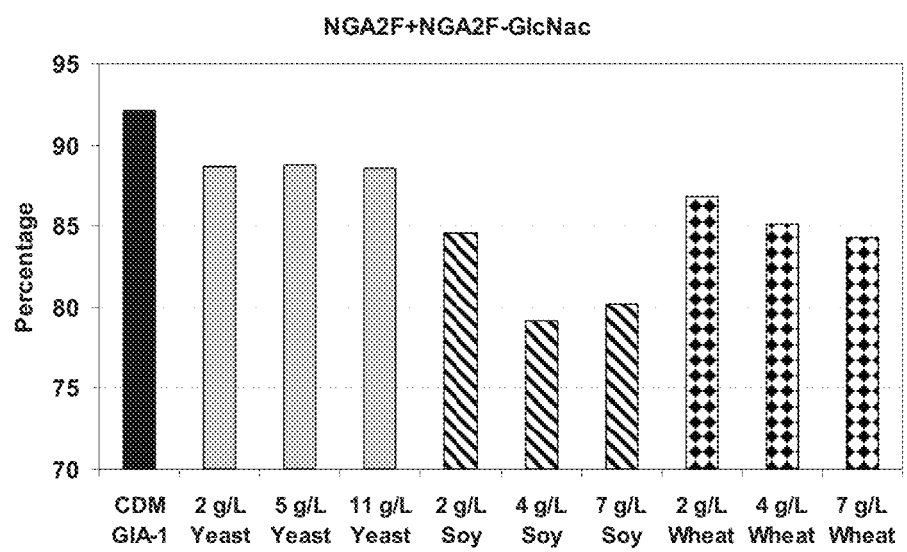
FIGS. 26A and 26B depict the effect of yeast, soy or wheat hydrolysate addition to CDM GIA-1 in CHO cell line producing mAb #1 on (FIG. 26A) NGA2F and (NGA2F-GlcNac) and (FIG. 26B) NA1F and NA2F, respectively.
Figure 26B:
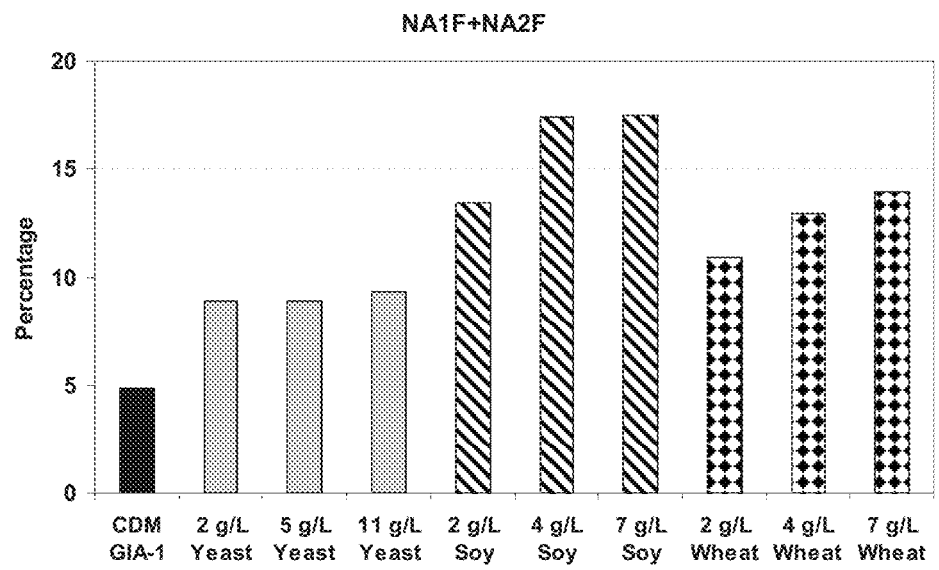

Addition of yeast hydrolysates to CD media GIA-1 lowered the percentage of NGA2F and NGA2F-GlcNac glycans by 3% and increased the percentage of NA1F and NA2F glycans by 4% compared to control (NGA2F and NGA2F-GlcNac: 92%; NA1F and NA2F: 5%) (FIGS. 26A-B). Addition of soy hydrolysates lowered the percentage of NGA2F and NGA2F-GlcNac glycans by 7-13% and increased the percentage of NA1F and NA2F glycans by 8-12% compared to control. Addition of wheat hydrolysates lowered the percentage of NGA2F and NGA2F-GlcNac glycans by 5-8% and increased the percentage of NA1F and NA2F glycans by 6-9% compared to control.

Example 10

Yeast, Soy or Wheat Hydrolysate Addition to CD Media GIA-1 for Culture of a CHO Cell Line Producing mAb #2

In the study summarized in this example, the effects on glycosylation resulting from the addition of yeast, soy or wheat hydrolysates to CD media GIA-1 in a CHO cell line producing mAb #2 were evaluated.

10.1 Materials and Methods

Adaptation and production media were supplemented with Bacto TC, BBL Phytone Peptone or Wheat Peptone E1 according to the experimental design in FIG. 46. The control cultures were not supplemented with hydrolysates. All media pH was adjusted to approximately 7.2 and the media osmolality was adjusted to 280-330 mOsmol/kg.

Upon thaw, cells were cultured in CD media GIA-1 growth media in a combination of Corning vented non-baffled shake flasks and maintained on a shaker platform at 140 RPM and 20 L cell bags. Cultures were propagated in a 35° C., 5% $CO_2$ dry incubator. Production cultures were initiated in duplicate 500 mL (200 mL working volume) Corning vented non-baffled shake flasks at an initial VCD of approximately 0.5×$10^6$ cells/mL. The shake flask study was run in an extended-batch mode by feeding a glucose solution (1.25% (v/v) of 40% solution) when the media glucose concentration fell below 3 g/L. For this study, samples were collected daily and measured for cell density and viability using a NOVA cell counter.

10.2 Culture Growth and Productivity

Figure 27A:
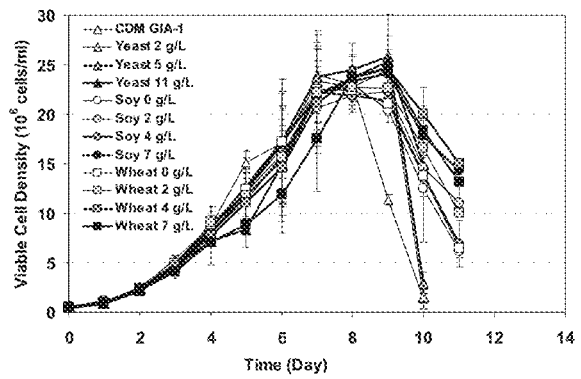
FIGS. 27A-27C depict the effect of yeast, soy or wheat hydrolysate addition to CDM GIA-1 in CHO cell line producing mAb #2 on (FIG. 27A) Culture growth, (FIG. 27B) Culture viability and (FIG. 27C) Harvest titer, respectively.
Figure 27B:
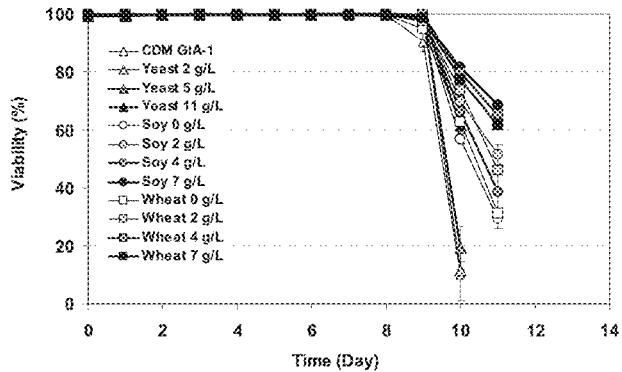
Figure 27C:
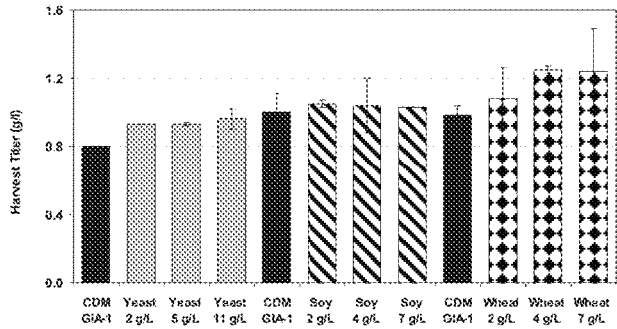

Supplementation of yeast, soy or wheat hydrolysates to CD media GIA-1 did not impact culture growth for most conditions studied compared to control (FIG. 27A). Supplementation with hydrolysates led to higher viability profiles compared to control (FIG. 27B). The addition of wheat hydrolysates increased harvest titer compared to the control (FIG. 27C).

10.3 Oligosaccharide Analysis

Figure 28A:
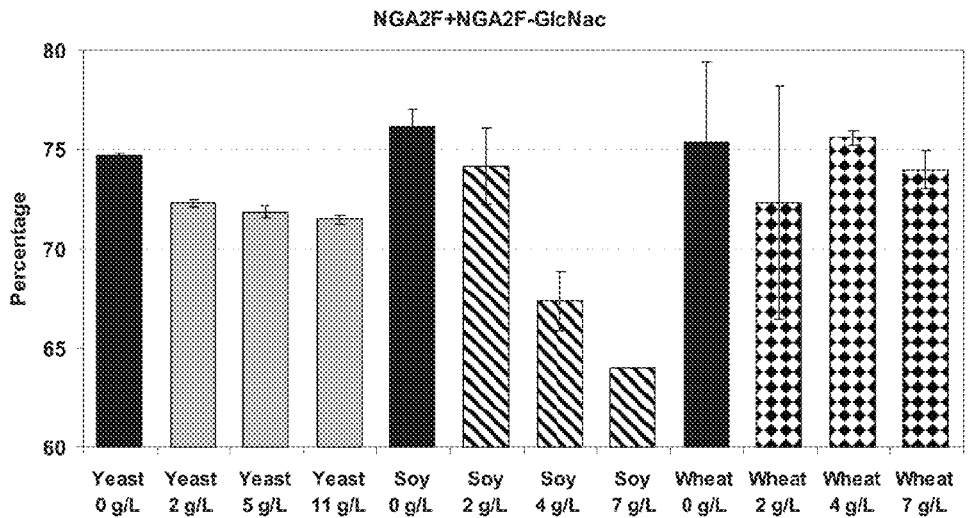
FIGS. 28A and 28B depict the effect of yeast, soy or wheat hydrolysate addition to CDM GIA-1 in CHO cell line producing mAb #2 on (FIG. 28A) NGA2F and (NGA2F-GlcNac) and (FIG. 28B) NA1F and NA2F, respectively.
Figure 28B:
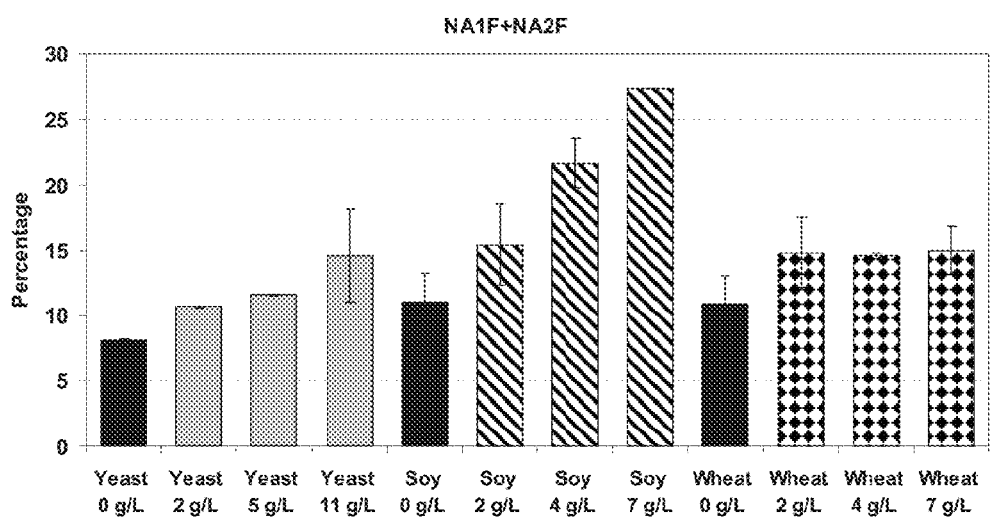

Addition of yeast hydrolysates to CD media GIA-1 lowered the percentage of NGA2F and NGA2F-GlcNac glycans by 3% (FIG. 28A) and increased the percentage of NA1F and NA2F glycans by 7% (FIG. 28B) in a dose-dependent manner compared to control (NGA2F and NGA2F-GlcNac: 75%; NA1F and NA2F: 8%). Addition of soy hydrolysates lowered the percentage of NGA2F and NGA2F-GlcNac by 2-12% and increased the percentage of NA1F and NA2F by 4-16% compared to control (NGA2F and NGA2F-GlcNac: 76%; NA1F and NA2: 11%). For this cell line, there was no significant difference in the percentage of NGA2F and NGA2F-GlcNac glycans between the control condition and the cultures supplemented with wheat hydrolysates at the concentration range evaluated. Furthermore, only a minor increase in the percentage of NA1F and NA2F glycans was observed.

Example 11

Combined Yeast, Soy and/or Wheat Hydrolysate Addition to CD Media GIA-1 for Culture of an Adalimumab-Producing CHO Cell Line #1

In the study summarized in this example, the effects on glycosylation resulting from the individual or combined addition of yeast, soy and/or wheat hydrolysates to CD media GIA-1 in the adalimumab-producing CHO cell line #1 utilized in Example 1 were evaluated.

11.1 Materials and Methods

Adaptation and production media were supplemented with Bacto TC Yeastolate, BBL Phytone Peptone and/or Wheat Peptone E1 according to the experimental design in FIGS. 47 and 48. The control cultures were not supplemented with hydrolysates. All media pH was adjusted to approximately 7.1 and the media osmolality was adjusted to 290-300 mOsmol/kg.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning vented non-baffled shake flasks at an initial VCD of approximately 0.5×$10^6$ cells/mL. The shake flask study was run in an extended-batch mode by feeding a glucose solution (1.25% (v/v) of 40% solution) when the media glucose concentration fell below 3 g/L.

11.2 Culture Growth and Productivity

Figure 29A:
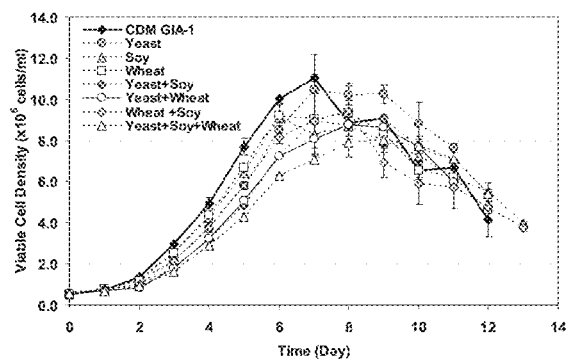
FIGS. 29A-29C depict the effect of combined supplementation of yeast, soy and/or wheat hydrolysates to CDM GIA-1 in adalimumab-producing CHO cell line #1 on (FIG. 29A) Culture growth, (FIG. 29B) Culture viability and (FIG. 29C) Harvest titer, respectively.
Figure 29B:
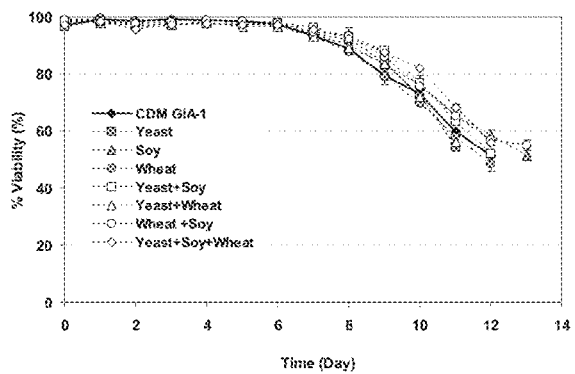
Figure 29C:
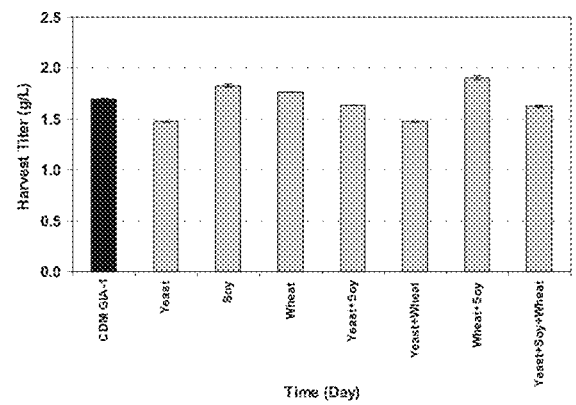

Supplementation of yeast, soy and/or wheat hydrolysates to CD media GIA-1 resulted in slight growth inhibition and reduced maximum VCD compared to the control (FIG. 29A). Culture viability profiles and harvest titer were comparable for all cultures (FIGS. 29B-C).

11.3 Oligosaccharide Analysis

Figure 30A:
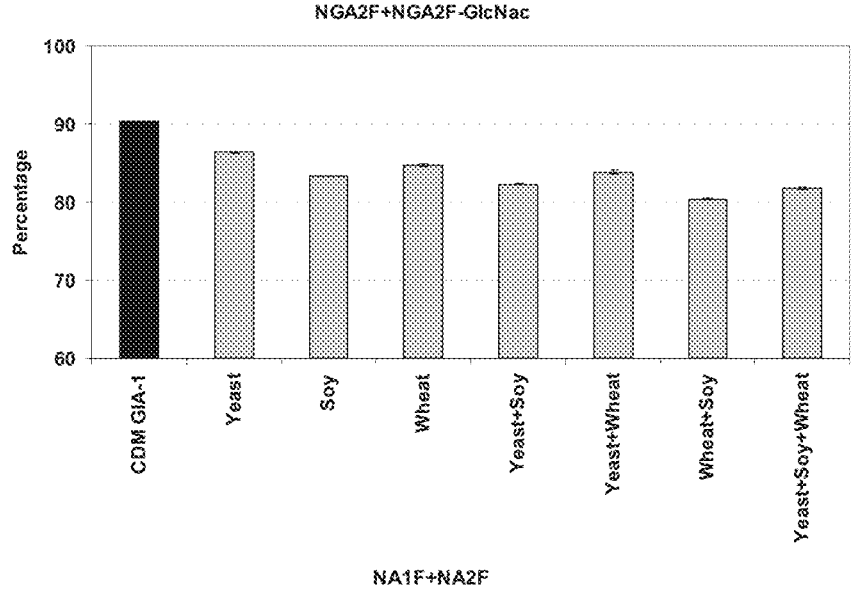
FIGS. 30A and 30B depict the effect of combined supplementation of yeast, soy and/or wheat hydrolysates to CDM GIA-1 in adalimumab-producing CHO cell line #1 on (FIG. 30A) NGA2F and (NGA2F-GlcNac) and (FIG. 30B) NA1F and NA2F, respectively.
Figure 30B:
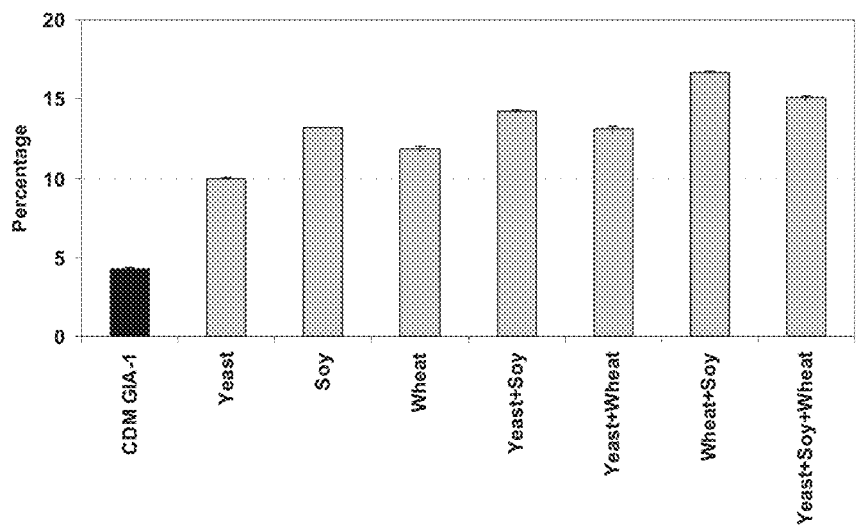

Supplementation of yeast hydrolysates only to CD media GIA-1 decreased the percentage of NGA2F and NGA2F-GlcNac glycans by 4% and increased the percentage of NA1F and NA2F glycans by 6% compared to control (NGA2F and NGA2F-GlcNac: 90%; NA1F and NA2F: 4%) (FIGS. 30A-B). Supplementation of soy hydrolysates only decreased the percentage of NGA2F and NGA2F-GlcNac glycans by 7% and increased the percentage of NA1F and NA2F glycans by 9% compared to control. Supplementation of wheat hydrolysates decreased the percentage of NGA2F and NGA2F-GlcNac glycans only by 5% and increased the percentage of NA1F and NA2F glycans by 8% compared to control.

The addition of two hydrolysates (yeast and soy; yeast and wheat; soy and wheat) further decreased the percentage of NGA2F and NGA2F-GlcNac glycans and increased the percentage of NA1F and NA2F glycans by a couple of percentages compared to the addition of each component individually (FIGS. 30A-B). Supplementing CD media GIA-1 with all three hydrolysates did not result in any further changes in the glycosylation profile, indicating a saturation state being reached.

Example 12

Effect of Asparagine in CD Media GIA-1 for Culture of Adalimumab-Producing CHO Cell Line #1

In the study summarized in this Example, the effects on product quality attributes resulting from the addition of asparagine to CD media GIA-1 in an adalimumab-producing CHO cell line, generically named CHO cell line #1 were investigated.

12.1 Materials and Methods

The CHO cell line #1 was employed in the study covered here. Upon thaw, cells were expanded in a 19-days seed train and then transferred into seed reactors for up to 7 days in growth medium. The cells were then brought to the laboratory and adapted in 500-mL shaker flasks with 200 mL working volume in CD media GIA1 medium for 13 days with 3 passages. The shaker flasks were placed on a shaker platform at 110 RPM in a 35° C., 5% $CO_2$ incubator.

The chemically defined growth or production media, was prepared from basal IVGN CD media GIA1. For preparation of the IVGN CD media formulation, the proprietary media was supplemented with L-glutamine, insulin, sodium bicarbonate, sodium chloride and methotrexate solution. Production media consisted of all the components in the growth medium, excluding methotrexate. In addition, 5 mM of Galactose (Sigma, G5388) and 10 μM of Manganese (Sigma, M1787) were supplemented into production medium. Osmolality was adjusted by the concentration of sodium chloride. All media was filtered through filter systems (0.22 μm PES) and stored at 4° C. until usage.

Production cultures were initiated in duplicate 500 mL Corning, vented, non-baffled shaker flasks each containing 200 mL culture in dry incubators with 5% $CO_2$ at 35° C. and 110 RPM. Initial VCD was approximately $0.5 \times 10^6$ cells/ml. The shake flask study was run in an extended batch mode by feeding a glucose solution (1.25% (v/v) of 40% solution) when the media glucose concentration fell below 3 g/L. Asparagine stock solution (20 g/L) was fed to culture on Day 6 to increase Asparagine concentration by 0, 0.4, 1.2 and 2.0 g/L.

Samples were taken daily from each reactor to monitor growth. The following equipment was used to analyze the samples: Cedex cell counter for cell density and viability; YSI 7100 analyzer for glucose and lactate concentration.

Some of the daily samples and the harvest samples were centrifuged at 3,000 rpm for 30 min and then supernatants were stored at −80° C. The thawed harvest samples were subsequently filtered through a 0.2 μm filter, purified by Protein A chromatography and then oligosaccharide analysis was performed as described in Example 1.

12.2 Culture Growth and Productivity

Figure 31A:
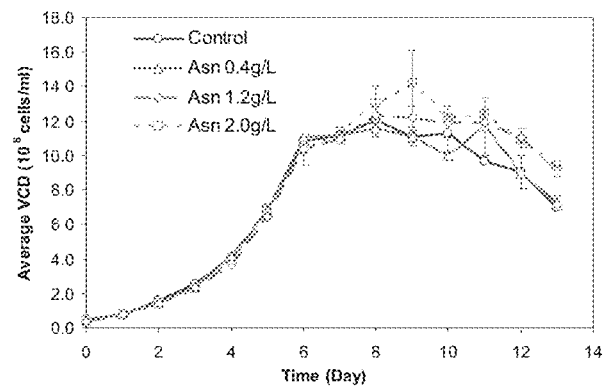
FIGS. 31A-31C depict the dose dependent effect of supplementation of asparagine on Day 6 to CDM GIA-1 in adalimumab-producing CHO cell line #1 on culture growth (FIG. 31A) and culture viability (FIG. 31B) and product titer (FIG. 31C), respectively.
Figure 31B:
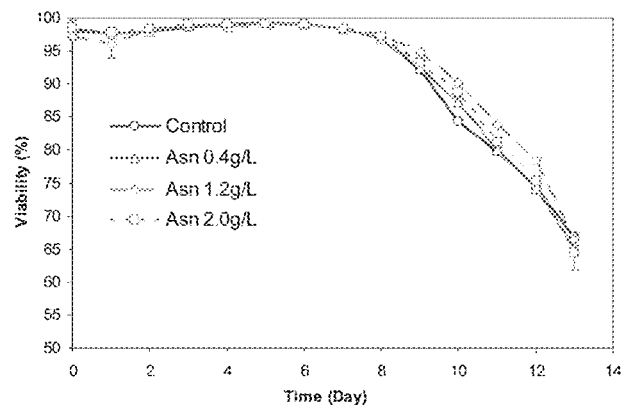
Figure 31C:
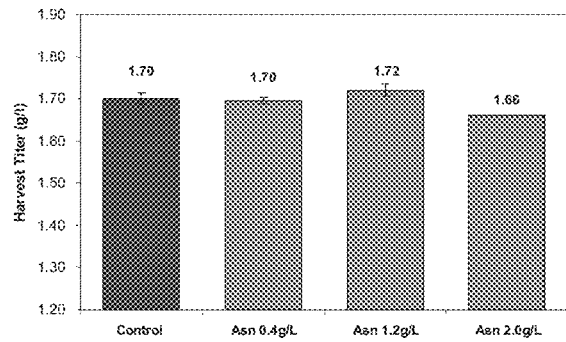

Feeding of asparagine to CD media GIA-1 did not impact culture growth for most conditions studied as compared to the control (FIG. 31A). The cultures showed similar growth rates and reached maximum VCD of ~$12 \times 10^6$ cells/mL. Culture viabilities were also very similar to that of the controls (FIG. 31B). Similarly, all the cultures examined here resulted in comparable harvest titers of approximately 1.7 g/L (FIG. 31C).

12.3 Oligosaccharide Analysis

Figure 32A:
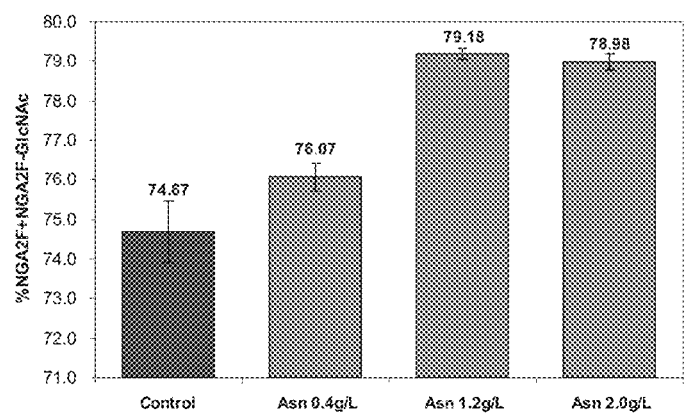
FIGS. 32A and 32B depict the dose dependent effect of supplementation of asparagine on Day 6 to CDM GIA-1 in adalimumab-producing CHO cell line #1 on NGA2F and (NGA2F-GlcNac) glycans (FIG. 32A) and on NA1F and NA2F glycans (FIG. 32B), respectively.

The effect of asparagine addition on oligosaccharide distribution was consistent with the experiments performed in hydrolysate based media described above. The addition of asparagine increased NGA2F and NGA2F-GlcNac glycans in a dose dependent manner (FIG. 32A). The percentage of NGA2F and NGA2F-GlcNac in the control sample (without Asparagine addition) was as low as 74.7%. In the sample with the addition of asparagine the percentage of NGA2F and NGA2F-GlcNAc was increased to 76.1% (0.4 g/L of asparagine), 79.2% (1.2 g/L of asparagine) and 79.0% (2.0 g/L of asparagine), for a total increase of 4.5%.

Figure 32B:
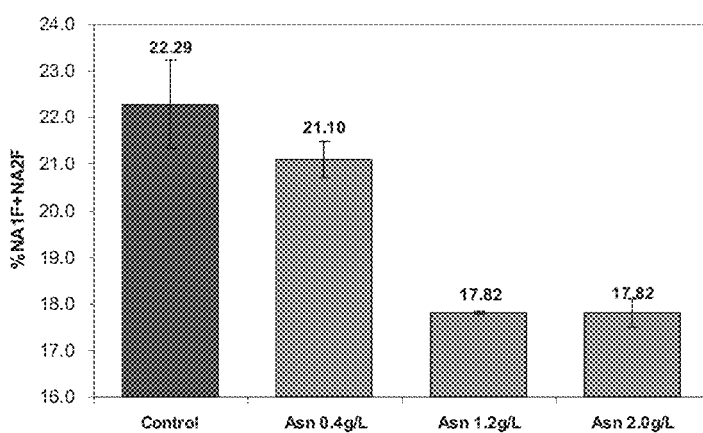

The percentage of NA1F and NA2F in the control sample (without asparagine addition) was as high as 22.3% (FIG. 32B). In the sample with the addition of asparagine the percentage of NA1F and NA2F was decreased to 21.1% (0.4 g/L of asparagine), 17.8% (1.2 g/L of asparagine) and 17.8% (2.0 g/L of asparagine), for a total reduction of 4.5%.

Example 13

Effect of Asparagine in CD Media GIA-1 for Culture of Adalimumab-Producing CHO Cell Line #3

In the study summarized in Example 13, the effects on product quality attributes resulting from the addition of asparagine to CD media GIA-1 in an adalimumab-producing CHO cell line, generically named CHO cell line #3 were investigated.

13.1 Materials and Methods

The CHO cell line #3 was employed in the study covered here. Upon thaw, adalimumab producing cell line #3 was cultured in CD media GIA-1 in a combination of vented shake flasks on a shaker platform @ 140 rpm and 20 L wave bags. Cultures were propagated in a 36° C., 5% $CO_2$ incubator to obtain the required number of cells to be able to initiate production stage cultures.

The chemically defined growth or production media was prepared from basal IVGN CD media GIA1. For preparation of the IVGN CD media formulation, the proprietary media was supplemented with L-glutamine, sodium bicarbonate, sodium chloride and methotrexate solution. Production media consisted of all the components in the growth medium, excluding methotrexate. In addition, 10 mM of Galactose (Sigma, G5388) and 0.2 μM of Manganese (Sigma, M1787) were supplemented into production medium. Osmolality was adjusted by the concentration of sodium chloride. All media was filtered through filter systems (0.22 μm PES) and stored at 4° C. until usage.

Production cultures were initiated in duplicate 500 mL Corning, vented, non-baffled shaker flasks each containing 200 mL culture in dry incubators with 5% $CO_2$ at 36° C. and 140 RPM. Initial VCD was approximately $0.5 \times 10^6$ cells/ml. The shake flask study was run in an extended batch mode by feeding a glucose solution (1.25% (v/v) of 40% solution) when the media glucose concentration fell below 3 g/L. Asparagine stock solution (20 g/L) was fed to culture on Day 6 to increase asparagine concentration by 0, 0.4, 0.8, 1.2, 1.6 and 2.0 g/L.

Samples were taken daily from each reactor to monitor growth. The following equipment was used to analyze the samples: Cedex cell counter for cell density and viability; YSI 7100 analyzer for glucose and lactate concentration.

Some of the daily samples and the harvest samples were centrifuged at 3,000 rpm for 30 min and then supernatants were stored at −80° C. The thawed harvest samples were subsequently filtered through a 0.2 μm filter, purified by Protein A chromatography and then oligosaccharide analysis was performed as described in Example 1.

13.2 Culture Growth and Productivity

Figure 33A:
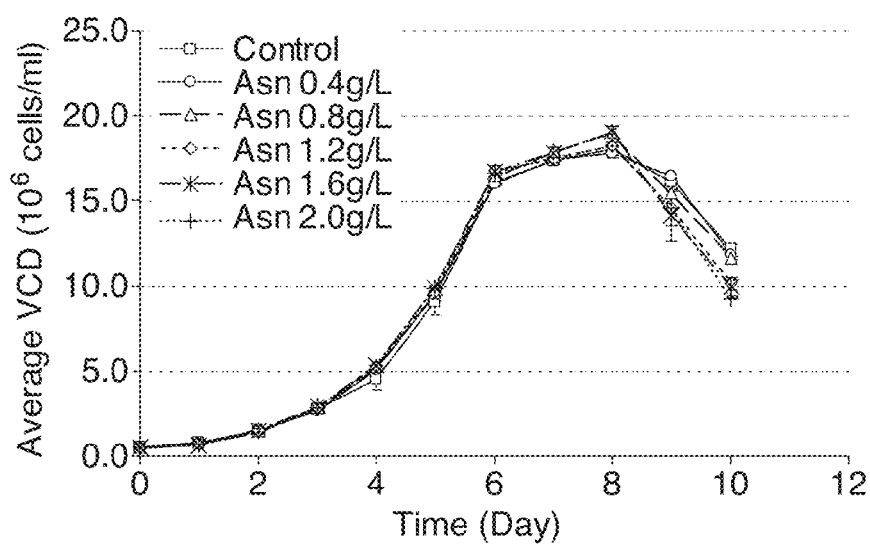
FIGS. 33A-33C depict the dose dependent effect of supplementation of asparagine on Day 6 to CDM GIA-1 in adalimumab-producing CHO cell line #2 on culture growth (FIG. 33A) and culture viability (FIG. 33B) and product titer (FIG. 33C), respectively.
Figure 33B:
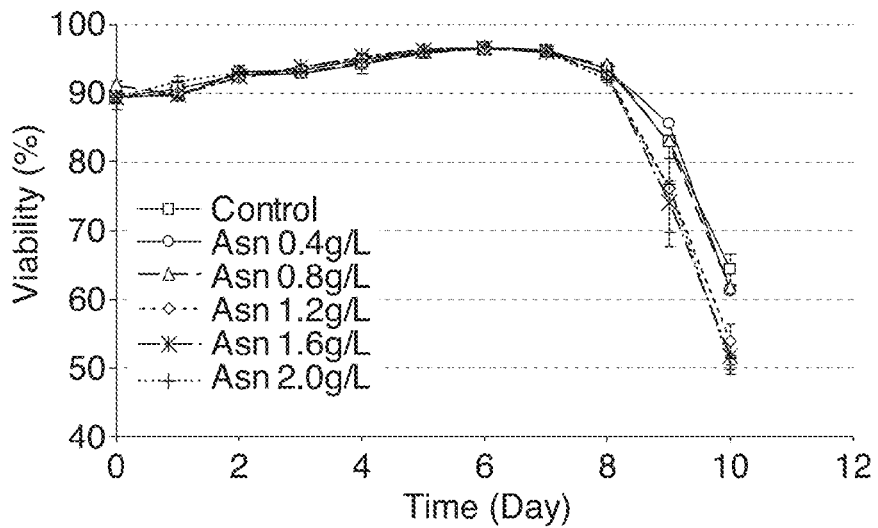
Figure 33C:
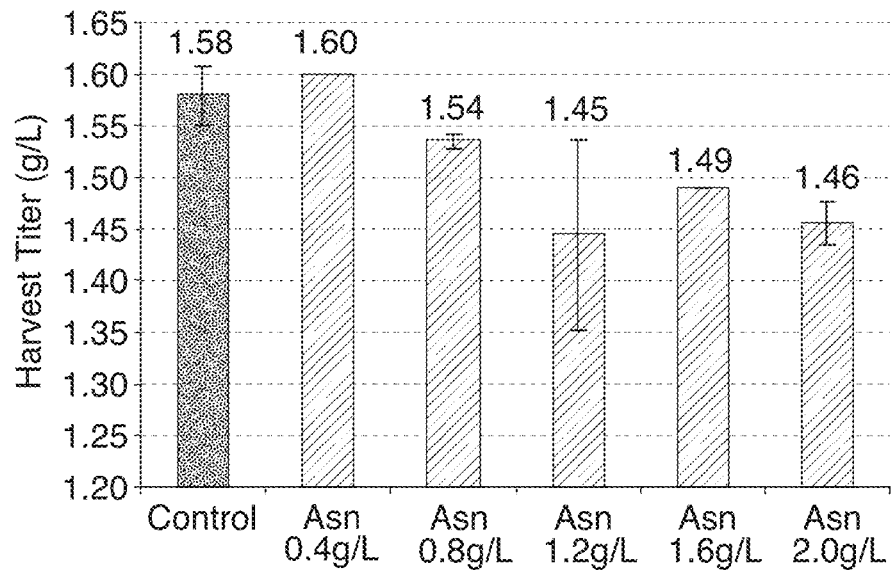

The experiment described in the instant Example used a different cell line (i.e., CHO cell line #3) in CD media GIA-1. Culture growth and viability profiles were comparable among all test conditions with different dosage of asparagine added on day 6 (FIGS. 33A and 33B). All cultures reached maximum VCD of ~18-19×10$^6$ cells/mL. The product titer (~1.5-1.6 g/L) was slightly reduced when higher dosage of asparagine was added (FIG. 33C).

13.3 Oligosaccharide Analysis

Figure 34A:
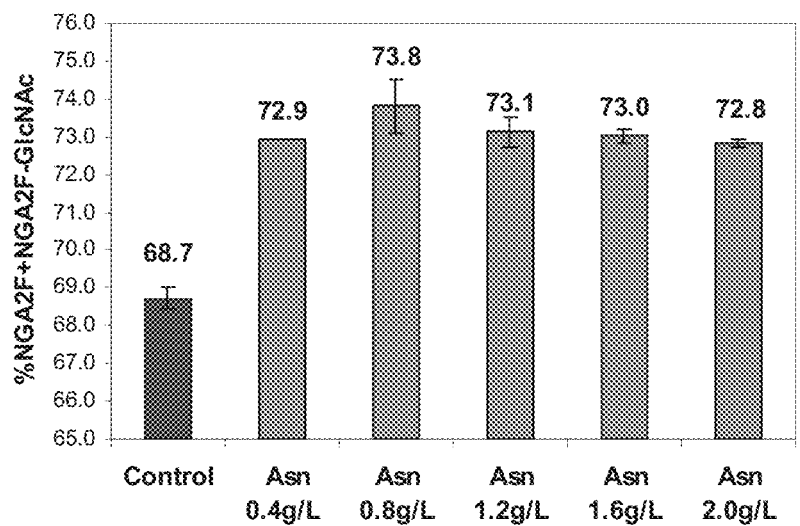
FIGS. 34A and 34B depict the dose dependent effect of supplementation of asparagine on Day 6 to CDM GIA-1 in adalimumab-producing CHO cell line #2 on NGA2F and (NGA2F-GlcNac) glycans (FIG. 34A) and on NA1F and NA2F glycans (FIG. 34B), respectively.
Figure 34B:
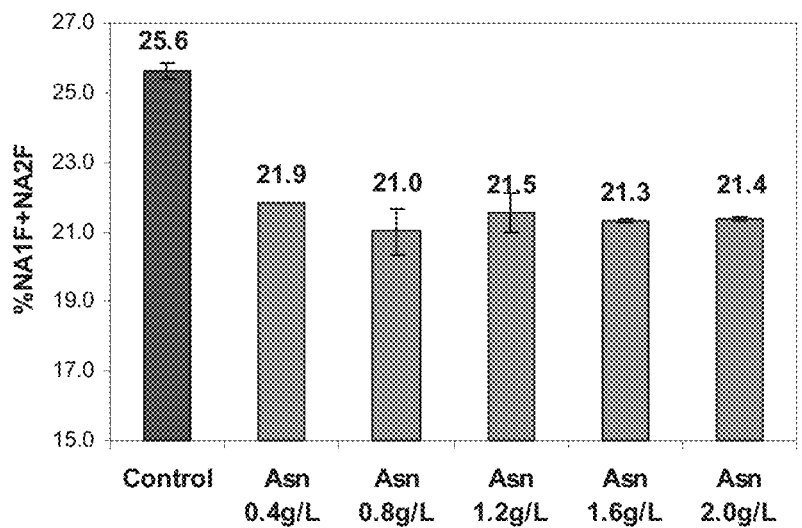

Again, the addition of asparagine increased NGA2F and NGA2F-GlcNac (FIG. 34A). The percentage of NGA2F and NGA2F-GlcNac in the control sample (without asparagine addition) was as low as 68.7%. In the sample with the addition of asparagine, the percentage of NGA2F and NGA2F-GlcNac was increased by 4.1-5.1% when 0.4 to 2.0 g/L asparagine was added on day 6 (FIG. 34A). The percentage of NA1F and NA2F in the control sample (without asparagine addition) was as high as 25.6% (FIG. 34B). In the sample with the addition of asparagine the percentage of NA1F and NA2F was decreased by 3.8-4.6% when 0.4 to 2.0 g/L asparagine was added on day 6 (FIG. 34B).

Example 14

Effect of Asparagine in a Shaker Flask Batch Culture in CD Media GIA-1 with a CHO Cell Line Producing mAb #2

In the studies summarized in Example 14, the effects on product quality attributes resulting from the addition of asparagine to CD media GIA-1 from Life Technologies Gibco in a CHO cell line producing monoclonal antibody #2 were investigated. In this instant Example, asparagine was either supplemented into culture media during media preparation or added on day 5 of the cell culture process.

14.1 Materials and Methods mAb #2 producing cell line was employed in the study covered here. Upon thaw, cells were cultured in chemically defined growth media in a combination of vented baffled shake flasks (Corning) on a shaker platform at 140 RPM. All media pH was adjusted to approximately 7.2 and the media osmolality was adjusted to 280-330 mOsmol/kg.

Cultures were propagated in a 35° C., 5% $CO_2$ incubator to obtain the required number of cells to be able to initiate production stage cultures. Production cultures were initiated in duplicate 500 mL vented non-baffled Corning shake flasks (200 mL working volume) at an initial viable cell density (VCD) of approximately 0.5×10$^6$ cells/mL. The shake flask study was run in an extended batch mode by feeding a glucose solution (1.25% (v/v) of 40% solution) when the media glucose concentration fell below 3 g/L. Asparagine (Sigma, Catalog Number A4284) were solubilized in Milli-Q water to make a 30 g/L stock solution. All media was filtered through Corning or Millipore 1 L filter systems (0.22 μm PES) and stored at 4° C. until usage.

For asparagine supplemented into culture media during media preparation, asparagine stock solution was supplemented to production media to increase asparagine concentration by 0, 0.4, 0.8 and 1.6 g/L. After addition of asparagine, media was brought to a pH similar to non-supplemented (control) media using 5N hydrochloric acid/5N NaOH and it was brought to an osmolality similar to non-supplemented (control) media by adjusting the concentration of sodium chloride. For asparagine addition study, asparagine stock solution was added to culture on Day 5 to increase Asparagine concentration by 0, 0.4, 0.8 and 1.6 g/L.

For all studies described throughout this invention, samples were collected daily and measured for cell density and viability using a NOVA cell counter. Retention samples for titer analysis via Poros A method were collected by centrifugation at 12,000 RPM for 5 min when the culture viability began declining. The cultures were harvested by collecting 125 mL aliquots and centrifuging at 3,000 RPM for 30 min when culture viability was near or below 50%. All supernatants were stored at −80° C. until analysis. The harvest samples were Protein A purified and then oligosaccharide analysis was performed as described in Example 1.

14.2 Culture Growth and Productivity

Figure 35A:
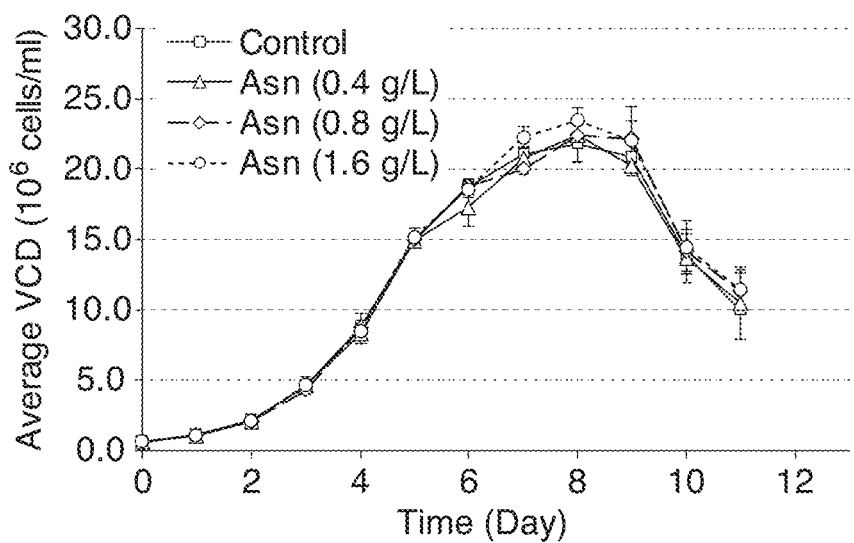
FIGS. 35A-35C depict the dose dependent effect of supplementation of asparagine during medium preparation to CDM GIA-1 in CHO cell line producing mAb #2 on culture growth (FIG. 35A) and culture viability (FIG. 35B) and product titer (FIG. 35C), respectively.
Figure 35B:
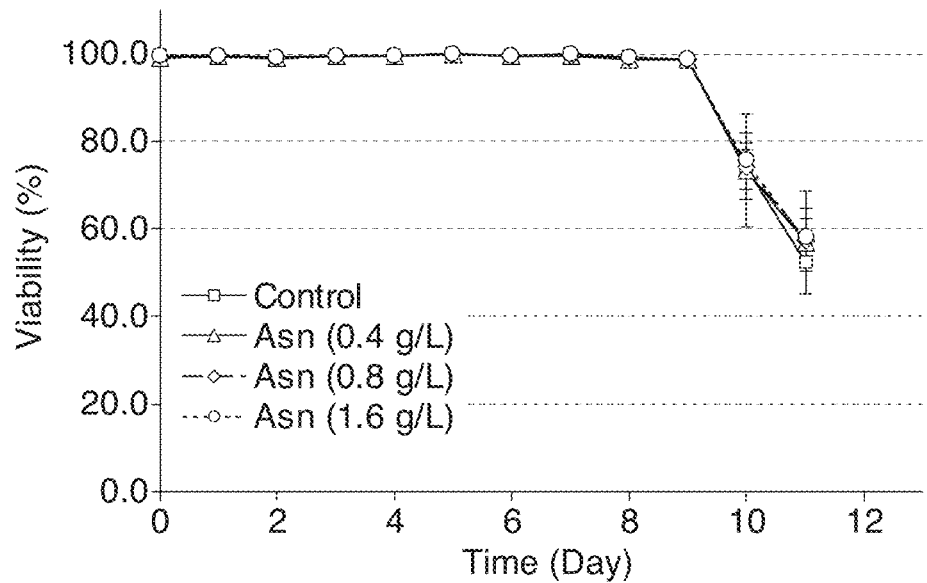
Figure 35C:
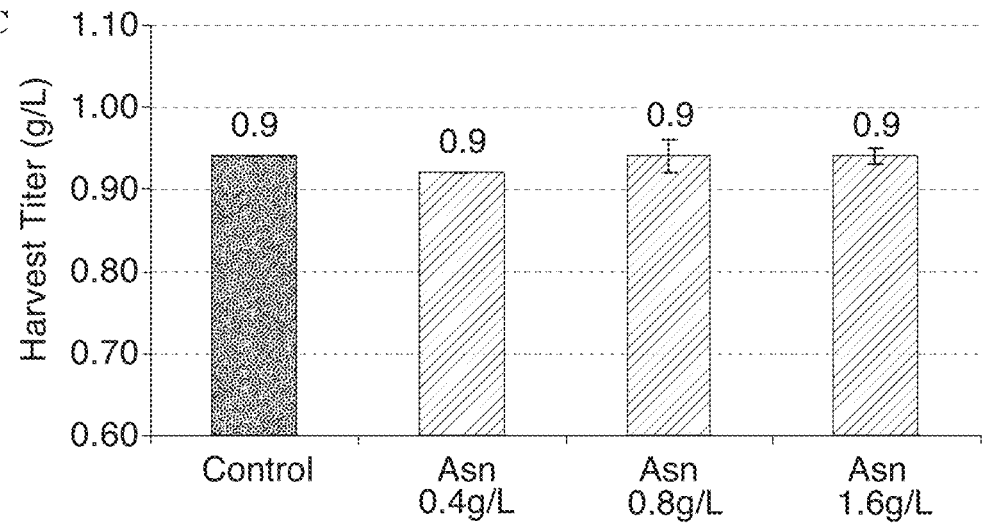
Figure 37A:
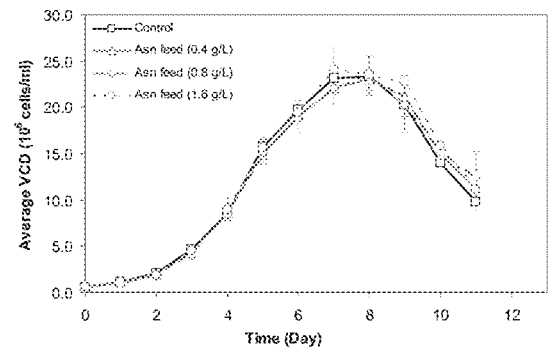
FIGS. 37A-37C depict the dose dependent effect of supplementation of asparagine on Day 5 to CDM GIA-1 in CHO cell line producing mAb #2 on culture growth (FIG. 37A) and culture viability (FIG. 37B) and product titer (FIG. 37C), respectively.
Figure 37B:
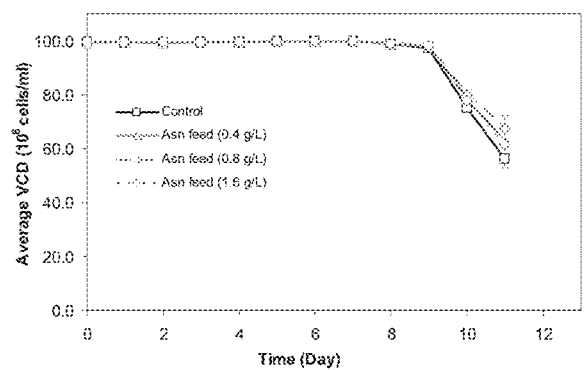
Figure 37C:
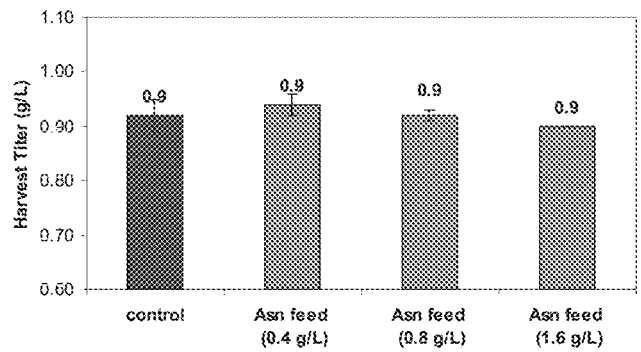

Adding asparagine to CD media GIA-1 during medium preparation or on day 5 of the cell culture did not impact culture growth for most conditions studied as compared to the non-supplemented 0 g/L controls (FIGS. 45A and 47A). The cultures showed similar growth rates and reached maximum VCD of 22-24×10$^6$ cells/mL. Culture viabilities were also very similar to that of the controls (FIGS. 35B and 37B). Similarly, all the cultures examined here resulted in comparable harvest titers of approximately 0.9 g/L of mAb #2 (FIGS. 35C and 37C).

14.3 Oligosaccharide Analysis

Figure 36A:
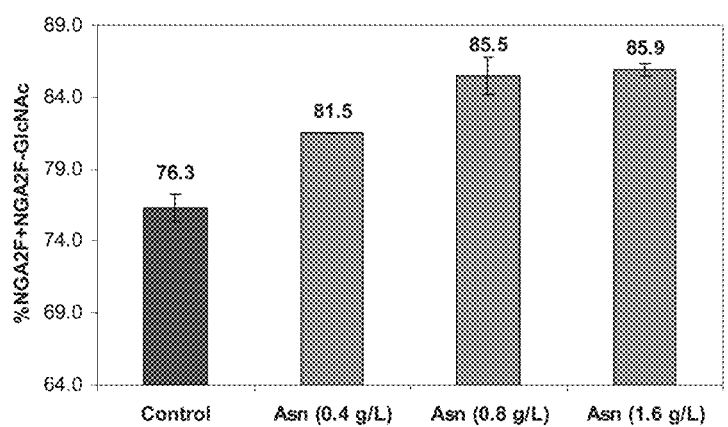
FIGS. 36A and 36B depict the dose dependent effect of supplementation of asparagine during medium preparation to CDM GIA-1 in CHO cell line producing mAb #2 on NGA2F and (NGA2F-GlcNac) glycans (FIG. 36A) and on NA1F and NA2F glycans (FIG. 36B), respectively.
Figure 36B:
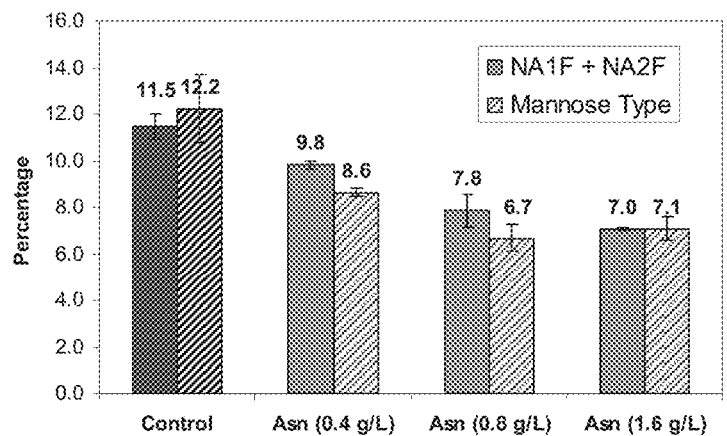

The addition of asparagine during medium preparation increased NGA2F and NGA2F-GlcNac glycans in a dose dependent manner (FIG. 36A). The percentage of NGA2F and NGA2F-GlcNac in the control sample (without asparagine addition) was as low as 76.3%. In the sample with the addition of asparagine the percentage of NGA2F and NGA2F-GlcNac was increased to 81.5% (0.4 g/L of asparagine), 85.5% (0.8 g/L of asparagine) and 85.9% (1.6 g/L of asparagine), for a total increase of 9.6%. The percentage of NA1F and NA2F in the control sample (without asparagine addition) was as high as 11.5% (FIG. 36B). In the sample with the addition of asparagine the percentage of NA1F and NA2F was decreased to 9.8% (0.4 g/L of asparagine), 7.8% (0.8 g/L of asparagine) and 7.0% (1.6 g/L of asparagine), for a total reduction of 4.5%. With mAb #2 cell line used in the study, the percentage of Mannose type glycans was also decreased with the supplementation of asparagine. The percentage of Mannoses in the control sample (without asparagine addition) was as high as 12.2% (FIG. 36B). In the sample with the addition of asparagine the percentage of Mannoses was decreased to 8.6% (0.4 g/L of asparagine), 6.7% (0.8 g/L of asparagine) and 7.1% (1.6 g/L of asparagine), for a total reduction of 5.5%.

Figure 38A:
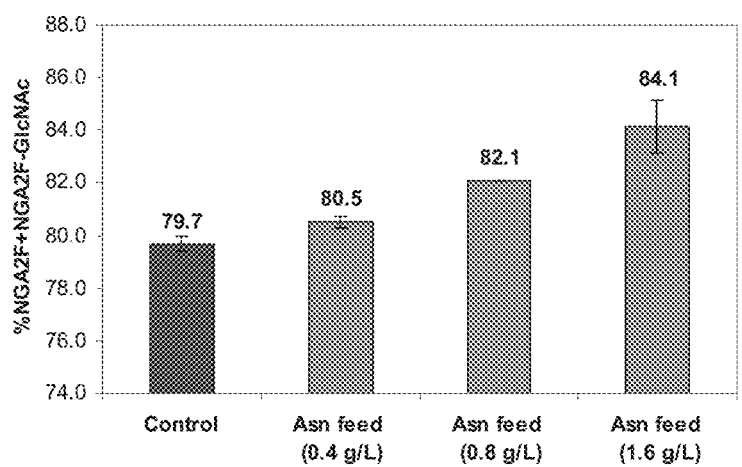
FIGS. 38A and 38B depict the dose dependent effect of supplementation of asparagine on Day 5 to CDM GIA-1 in CHO cell line producing mAb #2 on NGA2F and (NGA2F-GlcNac) glycans (FIG. 38A) and on NA1F and NA2F glycans (FIG. 38B), respectively.
Figure 38B:
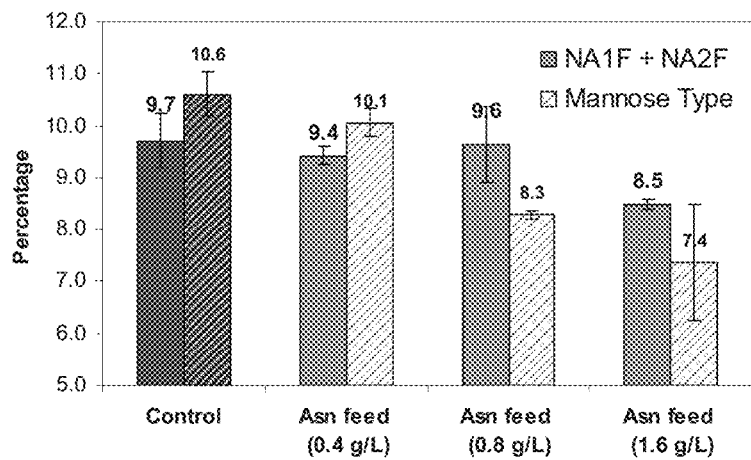

The addition of asparagine on day 5 of the culture also increased NGA2F and NGA2F-GlcNac glycans in a dose dependent manner (FIG. 38A). The percentage of NGA2F and NGA2F-GlcNac in the control sample (without asparagine addition) was as low as 79.7%. In the sample with the addition of asparagine the percentage of NGA2F and NGA2F-GlcNac was increased to 80.5% (0.4 g/L of asparagine), 82.1% (0.8 g/L of asparagine) and 84.1% (1.6 g/L of asparagine), for a total increase of 4.4%. The percentage of NA1F and NA2F in the control sample (without asparagine addition) was as high as 9.7% (FIG. 38B). In the sample with the addition of asparagine the percentage of NA1F and NA2F was decreased to 9.4% (0.4 g/L of asparagine), 9.6% (0.8 g/L of asparagine) and 8.5% (1.6 g/L of asparagine), for a total reduction of 1.2%. Again, the percentage of Mannose type glycans was also decreased with the supplementation of asparagine. The percentage of Mannoses in the control sample (without asparagine addition) was as high as 10.6% (FIG. 38B). In the sample with the addition of asparagine the percentage of Mannoses was decreased to 10.1% (0.4 g/L of asparagine), 8.3% (0.8 g/L of asparagine) and 7.4% (1.6 g/L of asparagine), for a total reduction of 3.2%.

Example 15

Effect of Pea Hydrolysate Addition to CD Media GIA-1 in Adalimumab-Producing CHO Cell Line #1

In the study summarized in this Example, the effects on glycosylation resulting from the addition of pea hydrolysate (Hy-Pea 7404, Kerry: 2, 4, 7, 10 g/L) to chemically defined (CD) medium GIA-1 (Life Technologies Gibco) in the adalimumab-producing CHO cell line #1 was investigated.

15.1 Materials and Methods

Adaptation media was supplemented with pea hydrolysate at a concentration of 2 g/L and production media were supplemented with pea hydrolysate at concentrations of 2, 4, 7, 10 g/L. Cultures not supplemented with pea hydrolysate were included as a control. In addition to pea hydrolysate, adaptation media was supplemented with 0.876 g/kg L-glutamine and 2.0 mL/kg methotrexate solution; production media was supplemented with 0.584 g/L L-glutamine. The pH of production media was adjusted to approximately 7.1 using 6N hydrochloric acid/5N sodium hydroxide. The media osmolality was adjusted to approximately 315 mOsmol/kg with sodium chloride.

The adalimumab-producing cultures were expanded for 4 passages (3 days each) in adaptation media containing 2 g/L pea hydrolysate in a combination of 250 mL (50 mL or 100 mL working volume), 500 mL (150 mL working volume) and 1 L (300 mL working volume) Corning vented non-baffled shake flasks and maintained on an orbital shaker at 110 RPM in a 35° C., 5% $CO_2$ dry incubator. At each passage, cultures were inoculated at an initial viable cell density (VCD) of approximately $0.5 \times 10^6$ cells/mL.

Production cultures were initiated in duplicate 500 mL Corning, vented, non-baffled shake flasks each containing 200 mL culture in dry incubators at 35° C., 5% $CO_2$ and 110 RPM. Initial VCD was approximately $0.5 \times 10^6$ cells/mL. A 1.25% (v/v) 40% glucose stock solution was fed when the media glucose concentration was less than 3 g/L.

Samples were collected and measured for cell density and viability as set forth in Example 1. In addition, the oligosaccharide assay was performed as set forth in Example 1.

15.2 Culture Growth and Productivity

Figure 49A:
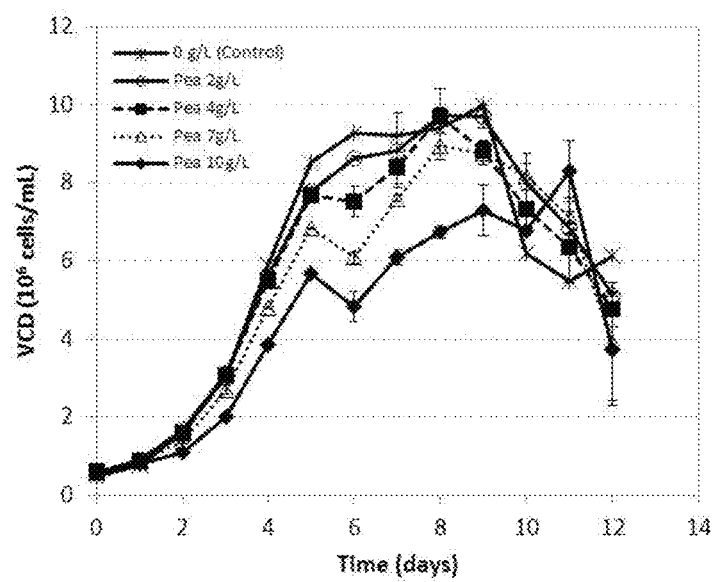
Figure 49B:
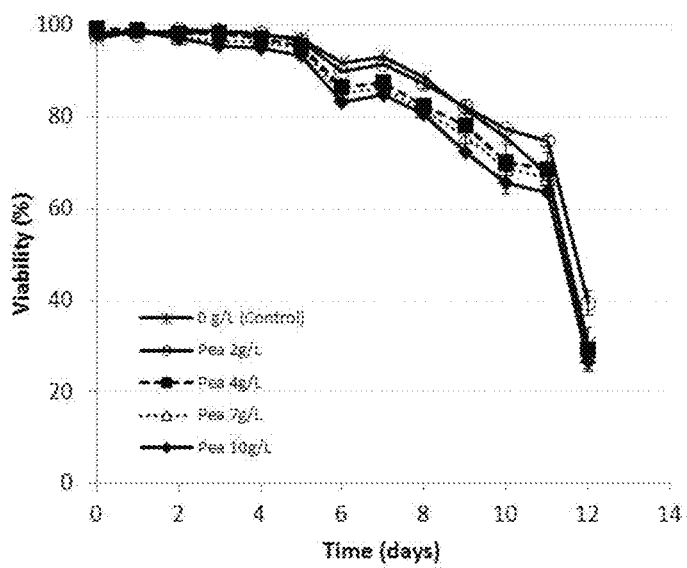

The majority of cultures grew to a similar peak VCD in the range of $9-10 \times 10^6$ cells/mL. Cultures supplemented with 10 g/L pea hydrolysate experienced slight inhibition of growth (FIG. 49A). The viability profile of cultures with 2 g/L pea hydrolysate were comparable to the control condition; however, a small dose-dependent decrease in viability was observed with higher concentrations of hydrolysate. The culture duration (12 days) was similar within the hydrolysate concentration range evaluated (FIG. 49B). However, a dose-dependent decrease in cell productivity compared to the control condition was observed with the addition of pea hydrolysate (FIG. 49C).

15.3 Oligosaccharide Analysis

Figure 50A:
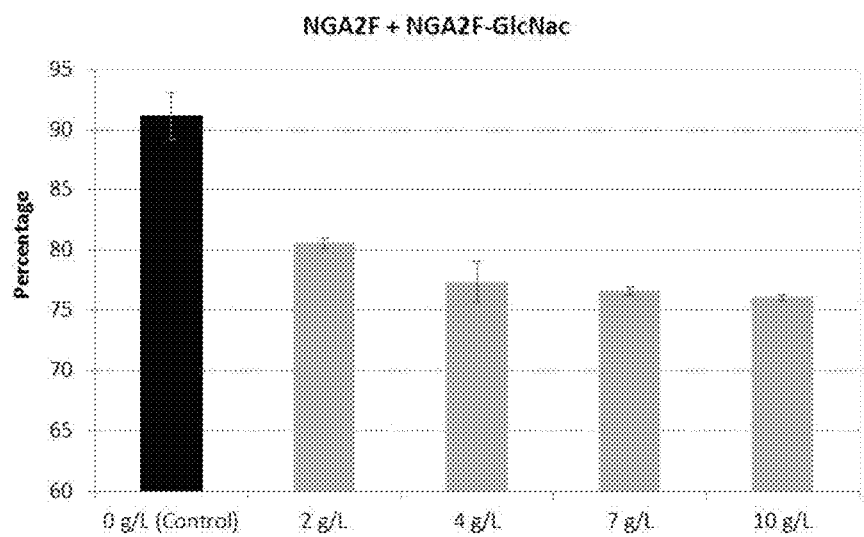
FIGS. 50A and 50B depict the effect of pea hydrolysate addition to CD media GIA-1 in adalimumab-producing CHO cell line #1 on NGA2F and (NGA2F-GlcNac) (FIG. 50A) and NA1F and NA2F (FIG. 50B), respectively.
Figure 50B:
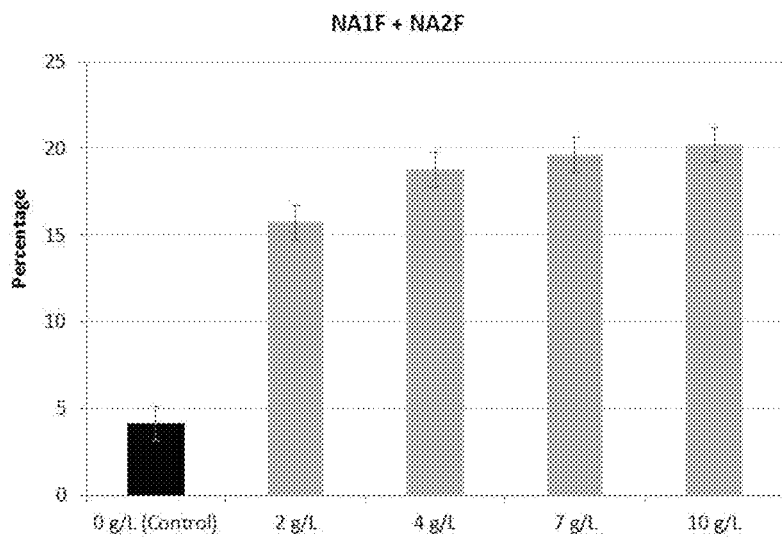

Addition of pea hydrolysate to CD media GIA-1 lowered the percentage of NGA2F and NGA2F-GlcNac glycans by 11-15% and increased the percentage of NA1F and NA2F glycans by 12-16% compared to control condition (NGA2F and NGA2F-GlcNac: 91%; NA1F and NA2F: 4%) (FIGS. 50A-B). A dose-dependent decrease in NGA2F and NGA2F-GlcNac and a corresponding increase in NA1F and NA2F glycans was observed with the addition of pea hydrolysate over the tested range.

What is claimed is:

1. A process for producing a recombinantly-expressed immunoglobulin comprising a heavy chain variable region comprising the sequence of SEQ ID NO: 2 and a light chain variable region comprising the sequence of SEQ ID NO: 7, comprising culturing a mammalian cell which recombinantly expresses the immunoglobulin during a production stage in a cell culture media comprising at least 0.4 g/L of asparagine, thereby producing the recombinantly-expressed immunoglobulin, wherein the level of agalactosyl fucosylated biantennary oligosaccharides (sum of NGA2F and NGA2F-GlcNac)

present on the produced immunoglobulin is increased as compared to the level of agalactosyl fucosylated biantennary oligosaccharides (sum of NGA2F and NGA2F-GlcNac) of immunoglobulin produced in cell culture media which does not comprise said asparagine during the production stage; and/or wherein the level of galactose containing fucosylated biantennary oligossacharides (sum of NA1F and NA2F) present on the produced immunoglobulin is decreased as compared to the level of galactose containing fucosylated biantennary oligossacharides (sum of NA1F and NA2F) of immunoglobulin produced in cell culture media which does not comprise said asparagine during the production stage.

2. The process of claim 1, wherein the immunoglobulin is adalimumab.

3. The process of claim 1, wherein the cell which expresses the immunoglobulin is a CHO cell.

4. The process of claim 1, wherein the media comprises asparagine at a concentration of at least 0.6 g/L, 0.8 g/L, 1.0 g/L, 1.2 g/L, 1.4 g/L, 1.6 g/L, 1.8 g/L or 2 g/L, or between 0.4 g/L-1.4 g/L, or between 0.4 g/L-2 g/L.

5. The process of claim 1, wherein the media further comprises glutamine.

6. The process of claim 5, wherein the media comprises glutamine at a concentration of at least 0.2 g/L or between 0.1 g/L to 4 g/L.

7. The process of claim 1, wherein the level of agalactosyl fucosylated biantennary oligosaccharides (sum of NGA2F and NGA2F-GlcNAc) present on the produced immunoglobulin is 64%-88%, 70%-88% or 75%-85%; and/or wherein the level of fucosylated biantennary oligosaccharides (sum of NA1F and NA2F) present on the produced immunoglobulin is 1%-30%, 2%-25%, 5%-20%, 5%-15%, 10%-20% or 27%-31%.

8. The process of claim 1, wherein the process is a fed batch process.

9. The process of claim 1, wherein the media further comprises a yeast hydrolysate and/or a plant hydrolysate; optionally, wherein the yeast hydrolysate is selected from the group consisting of Bacto TC Yeastolate, HyPep Yeast Extract and UF Yeast Hydrolysate; and/or wherein the plant hydrolysate is selected from the group consisting of a soy hydrolysate, a wheat hydrolysate, a rice hydrolysate, a cotton seed hydrolysate, a pea hydrolysate, a corn hydrolysate, a potato hydrolysate, BBL Phytone Peptone, HyPep 1510, SE50 MAF-UF, UF Soy Hydrolysate, Wheat Peptone E1, HyPep 4601 and Proyield WGE80M Wheat.

10. The process of claim 9, wherein the yeast hydrolysate is present in the media at a concentration of between 2 g/L to 11 g/L and/or wherein the plant hydrolysate is present in the media at a concentration of between 2 g/L to 15 g/L.

11. A process for producing a recombinantly-expressed immunoglobulin comprising a heavy chain variable region comprising the sequence of SEQ ID NO:2 and a light chain variable region comprising the sequence of SEQ ID NO: 7, comprising culturing a mammalian cell which recombinantly expresses the immunoglobulin in a cell culture media comprising asparagine and at least 1 g/L of glutamine, thereby producing the recombinantly-expressed immunoglobulin, and assessing the oligosaccharide distribution of the produced immunoglobulin, wherein the level of agalactosyl fucosylated biantennary oligosaccharides (sum of NGA2F and NGA2F-GlcNac) present on the produced immunoglobulin is increased as compared to the level of agalactosyl fucosylated biantennary oligosaccharides (sum of NGA2F and NGA2F-GlcNac) of immunoglobulin produced in cell culture media which does not comprise said asparagine and glutamine; and/or wherein the level of galactose containing fucosylated biantennary oligossacharides (sum of NA1F and NA2F) present on the produced immunoglobulin is decreased as compared to the level of galactose containing fucosylated biantennary oligossacharides (sum of NA1F and NA2F) of immunoglobulin produced in cell culture media which does not comprise said asparagine and glutamine.

12. The process of claim 11, wherein the immunoglobulin is adalimumab.

13. The process of claim 11, wherein the cell which expresses the immunoglobulin is a CHO cell.

14. The process of claim 11, wherein the cell culture media comprises asparagine at a concentration of at least 0.2 g/L or between 0.1 g/L to 4 g/L.

15. The process of claim 11, wherein the cell culture media comprises at least 2 g/L of glutamine.

16. The process of claim 11, wherein the cell culture media is a chemically defined cell culture media.

17. The process of claim 11, wherein the level of agalactosyl fucosylated biantennary oligosaccharides (sum of NGA2F and NGA2F-GlcNAc) present on the produced immunoglobulin is 64%-88%, 70%-88% or 75%-85%; and/or wherein the level of fucosylated biantennary oligosaccharides (sum of NA1F and NA2F) present on the produced immunoglobulin is 1%-30%, 2%-25%, 5%-20%, 5%-15%, 10%-20% or 27%-31%.

18. The process of claim 11, wherein the process is a fed batch process.

19. The process of claim 11, wherein the culture media further comprises a yeast hydrolysate and/or a plant hydrolysate; optionally, wherein the yeast hydrolysate is selected from the group consisting of Bacto TC Yeastolate, HyPep Yeast Extract and UF Yeast Hydrolysate; and/or wherein the plant hydrolysate is selected from the group consisting of a soy hydrolysate, a wheat hydrolysate, a rice hydrolysate, a cotton seed hydrolysate, a pea hydrolysate, a corn hydrolysate, a potato hydrolysate, BBL Phytone Peptone, HyPep 1510, SE50 MAF-UF, UF Soy Hydrolysate, Wheat Peptone E1, HyPep 4601 and Proyield WGE80M Wheat.

20. The process of claim 19, wherein the yeast hydrolysate is present in the media at a concentration of between 2 g/L to 11 g/L and/or wherein the plant hydrolysate is present in the media at a concentration of between 2 g/L to 15 g/L.

21. A process for producing a recombinantly-expressed immunoglobulin comprising a heavy chain variable region comprising the sequence of SEQ ID NO:2 and a light chain variable region comprising the sequence of SEQ ID NO: 7, comprising culturing a mammalian cell which recombinantly expresses the immunoglobulin in a cell culture media comprising at least 0.6 g/L of asparagine, thereby producing the recombinantly-expressed immunoglobulin, wherein the level of agalactosyl fucosylated biantennary oligosaccharides (sum of NGA2F and NGA2F-GlcNac) present on the produced immunoglobulin is increased as compared to the level of agalactosyl fucosylated biantennary oligosaccharides (sum of NGA2F and NGA2F-GlcNac) of immunoglobulin produced in cell culture media which does not comprise said asparagine; and/or wherein the level of galactose containing fucosylated biantennary oligossacharides (sum of NA1F and NA2F) present on the produced immunoglobulin is decreased as compared to the level of galactose containing fucosylated biantennary oligosaccharides (sum of NA1F and NA2F) of immunoglobulin produced in cell culture media which does not comprise said asparagine.

22. The process of claim 21, wherein the immunoglobulin is adalimumab.

23. The process of claim 21, wherein the cell which expresses the immunoglobulin is a CHO cell.

24. The process of claim 21, wherein the cell culture media comprises asparagine at a concentration of at least 0.8 g/L, 1.0 g/L, 1.2 g/L, 1.4 g/L, 1.6 g/L, 1.8 g/L or 2.0 g/L.

25. The process of claim 21, wherein the cell culture media further comprises glutamine.

26. The process of claim 21, wherein the cell culture media comprises glutamine at a concentration of at least 0.2 g/L or between 0.1 g/L to 4 g/L.

27. The process of claim 21, wherein the level of agalactosyl fucosylated biantennary oligosaccharides (sum of NGA2F and NGA2F-GlcNAc) present on the produced immunoglobulin is 64%-88%, 70%-88% or 75%-85%; and/or wherein the level of fucosylated biantennary oligosaccharides (sum of NA1F and NA2F) present on the produced immunoglobulin is 1%-30%, 2%-25%, 5%-20%, 5%-15%, 10%-20% or 27%-31%.

28. The process of claim 21, wherein the process is a fed batch process.

29. The process of claim 21, wherein the culture media further comprises a yeast hydrolysate and/or a plant hydrolysate; optionally, wherein the yeast hydrolysate is selected from the group consisting of Bacto TC Yeastolate, HyPep Yeast Extract and UF Yeast Hydrolysate; and/or wherein the plant hydrolysate is selected from the group consisting of a soy hydrolysate, a wheat hydrolysate, a rice hydrolysate, a cotton seed hydrolysate, a pea hydrolysate, a corn hydrolysate, a potato hydrolysate, BBL Phytone Peptone, HyPep 1510, SE50 MAF-UF, UF Soy Hydrolysate, Wheat Peptone E1, HyPep 4601 and Proyield WGE80M Wheat.

30. The process of claim 29, wherein the yeast hydrolysate is present in the media at a concentration of between 2 g/L to 11 g/L and/or wherein the plant hydrolysate is present in the media at a concentration of between 2 g/L to 15 g/L.

* * * * *

UNITED STATES PATENT AND TRADEMARK OFFICE
CERTIFICATE OF CORRECTION

| | | |
|---|---|---|
| PATENT NO. | : 9,290,568 B2 | Page 1 of 1 |
| APPLICATION NO. | : 14/632572 | |
| DATED | : March 22, 2016 | |
| INVENTOR(S) | : Lisa M. Rives et al. | |

It is certified that error appears in the above-identified patent and that said Letters Patent is hereby corrected as shown below:

On the Title Page:

In the Related U.S. Application Data, item (63), please change "Continuation of application No. 14/194,305, filed on Feb. 28, 2014, which is a continuation of application" to --Continuation of application No.: 14/194,305, filed on Feb. 28, 2014, which is a continuation in part of application--;

In the Claims:

In claim 1 (column 73, lines 7-8), delete "oligossacharides" and replace with --oligosaccharides--;

In claim 1 (column 73, line 11), delete "oligossacharides" and replace with --oligosaccharides--;

In claim 11 (column 74, line 3), delete "oligossacharides" and replace with --oligosaccharides--;

In claim 11 (column 74, lines 6-7), delete "oligossacharides" and replace with --oligosaccharides--;

In claim 21 (column 74, line 62), delete "oligossacharides" and replace with --oligosaccharides--; and In claim 21 (column 74, line 65), delete "oligossacharides" and replace with --oligosaccharides--.

Signed and Sealed this
Thirty-first Day of May, 2016

Michelle K. Lee
*Director of the United States Patent and Trademark Office*

SEQUENCE LISTING

```
<160> NUMBER OF SEQ ID NOS: 12

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2
```

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
             100                 105                 110

Gln Gly Thr Leu Val Thr Val Ser Ser
         115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
  1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: VARIANT
<222> LOCATION: 12
<223> OTHER INFORMATION: Xaa = Tyr or Asn

<400> SEQUENCE: 4

Val Ser Tyr Leu Ser Thr Ala Ser Ser Leu Asp Xaa
  1               5                  10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
  1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2
```

```
<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
 1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                                321

<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
gcggactctg tggagggccg attcaccatc tccagagaca cgccaagaa ctccctgtat      240 ctgcaaatga acagtctgag agctgaggat acggccgtat attactgtgc gaaagtctcg     300
taccttagca ccgcgtcctc ccttgactat tggggccaag taccctggt caccgtctcg      360 agt                                                                    363
```

```
<210> SEQ ID NO 11
<211> LENGTH: 214
<212> TYPE: PRT
<213> ORGANISM: Artificial Sequence
<220> FEATURE:
<223> OTHER INFORMATION: adalimumab light chain

<400> SEQUENCE: 11
```

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 12
<211> LENGTH: 451
<212> TYPE: PRT
<213> ORGANISM: Artificial Sequence
<220> FEATURE:
<223> OTHER INFORMATION: adalimumab heavy chain

<400> SEQUENCE: 12
```

Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
                    85                  90                  95
Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                    325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450
```